United States Patent
Gibson et al.

(10) Patent No.: US 11,541,177 B2
(45) Date of Patent: Jan. 3, 2023

(54) INJECTION SPRING FOR AGED PREFILLED SYRINGE AND AUTO INJECTOR

(71) Applicant: Teva Pharmaceuticals International GmbH, Jona (CH)

(72) Inventors: Paul Andrew Christopher Gibson, Chester (GB); Edward Andrew Cummings, Oswestry (GB)

(73) Assignee: Teva Pharmaceuticals International GmbH, Jona (CH)

( * ) Notice: Subject to any disclaimer, the term of this patent is extended or adjusted under 35 U.S.C. 154(b) by 241 days.

(21) Appl. No.: 16/576,670

(22) Filed: Sep. 19, 2019

(65) Prior Publication Data

US 2020/0093992 A1    Mar. 26, 2020

Related U.S. Application Data

(60) Provisional application No. 62/734,209, filed on Sep. 20, 2018.

(51) Int. Cl.
*A61M 5/20* (2006.01)
*A61M 5/315* (2006.01)

(52) U.S. Cl.
CPC ........ *A61M 5/2033* (2013.01); *A61M 5/3158* (2013.01); *A61M 5/31513* (2013.01); *A61M 2205/0222* (2013.01)

(58) Field of Classification Search
CPC .................................................. A61M 5/2033
USPC ......................................................... 604/134
See application file for complete search history.

(56) References Cited

U.S. PATENT DOCUMENTS

| 8,007,794 B2 | 8/2011 | Zeller et al. | |
| 2013/0303985 A1* | 11/2013 | Wotton | A61M 5/3153 604/218 |
| 2014/0010969 A1* | 1/2014 | Bicker | H01J 37/32394 427/535 |
| 2015/0018800 A1* | 1/2015 | Reb | A61B 17/12186 604/230 |

(Continued)

FOREIGN PATENT DOCUMENTS

| EP | 2170435 A2 | 4/2010 |
| WO | 2007054809 A2 | 5/2007 |

(Continued)

OTHER PUBLICATIONS

Strassman et al., "Fremanezumab—A Humanized Monoclonal Anti-CGRP Antibody—Inhibits Thinly Myelinated (Aδ) But Not Unmyelinated (C) Meningeal Nociceptors", The Journal of Neuroscience (2017), 37(44):10587-10596 (Year: 2017).*

(Continued)

*Primary Examiner* — Bhisma Mehta
*Assistant Examiner* — Nidah Hussain
(74) *Attorney, Agent, or Firm* — Blank Rome LLP

(57) ABSTRACT

A method of adapting an auto injector configured to actuate a prefilled syringe, the auto injector having a biasing member having a spring constant, the prefilled syringe being filled with a volume of therapeutic fluid, the prefilled syringe including a barrel, stopper, and a needle, the stopper having a path of travel, the biasing member arranged to move the stopper along the path of travel. An auto injector having an injection spring adapted to an aged prefilled syringe.

19 Claims, 22 Drawing Sheets

Specification includes a Sequence Listing.

(56) References Cited

U.S. PATENT DOCUMENTS

| | | | |
|---|---|---|---|
| 2015/0165129 A1* | 6/2015 | Row | A61M 5/31501 604/189 |
| 2015/0322142 A1* | 11/2015 | Bigal | A61K 45/06 424/152.1 |
| 2016/0008541 A1 | 1/2016 | Hirschel et al. | |
| 2018/0127490 A1* | 5/2018 | Bigal | C07K 16/18 |
| 2018/0243508 A1* | 8/2018 | Berg | A61M 5/31573 |

FOREIGN PATENT DOCUMENTS

| | | |
|---|---|---|
| WO | WO 2009/010591 A2 | 1/2009 |
| WO | WO 2017/089260 A1 | 6/2017 |
| WO | WO 2017/139003 A1 | 8/2017 |
| WO | WO 2017/191306 A1 | 11/2017 |

OTHER PUBLICATIONS

International Search Report and Written Opinion for PCT/IB2019/001050 dated Mar. 27, 2020, 25 pages.

Patricia Y. Love: "Guidance for Industry and FDA Staff: Glass Syringes for Delivering Drug and Biological Products: Technical Information to Supplement International Organization for Standardization (ISO) Standard 11040-4", pp. 1-14. retrieved from the Internet: URL: https://www.fda.gov/media/85748/download, Apr. 1, 2013.

Patricia Y. Love: "Guidance for Industry and FDA Staff: Technical Considerations for Pen, Jet, and Related Injectors Intended for Use with Drugs and Biological Products", pp. 1-29, retrieved from the Internet: URL: https://www.fda.gov/media/76403/download, Jun. 1, 2013.

Geoffrey S. Clark: "Shelf life of Medical Devices", pp. 1-27, retrieved from the Internet: URL: https://www.fda.gov/media/72487/download, Apr. 1991.

Food and Drug Administration: "Guidance for Industry and FDA Staff: Current Good Manufacturing Practice Requirements for Combination Products", pp. 1-59, retrieved from the Internet: URL: https://www.fda.gov/media/90425/download, Jan. 1, 2017.

Jian Liu: "Shelf Life Determination for Combination Medical Device Products", Pharmaceutical Outsourcing, pp. 1-4, Aug. 22, 2018.

Bruno Reuter et al: "Syringe Siliconization: Trends, methods, analysis procedures", TechnoPharm 2, No. 4, pp. 238-244, 2012.

Partial International Search Report for PCT/IB2019/001050 dated Jan. 31, 2020.

Proposed INN: List 115, WHO Drug Information, vol. 30, No. 2, 2016, pp. 280-281.

\* cited by examiner

FIG. 2

SEQ ID NO: 1-- Heavy Chain Variable Region of Humanized Antibody

Glu Val Gln Leu Val Glu Ser Gly Gly Gly Leu Val Gln Pro Gly Gly

Ser Leu Arg Leu Ser Cys Ala Ala Ser Gly Phe Thr Phe Ser Asn Tyr

Trp Ile Ser Trp Val Arg Gln Ala Pro Gly Lys Gly Leu Glu Trp Val

Ala Glu Ile Arg Ser Glu Ser Asp Ala Ser Ala Thr His Tyr Ala Glu

Ala Val Lys Gly Arg Phe Thr Ile Ser Arg Asp Asn Ala Lys Asn Ser

Leu Tyr Leu Gln Met Asn Ser Leu Arg Ala Glu Asp Thr Ala Val Tyr

Tyr Cys Leu Ala Tyr Phe Asp Tyr Gly Leu Ala Ile Gln Asn Tyr Trp

Gly Gln Gly Thr Leu Val Thr Val Ser Ser

SEQ ID NO: 2--Light Chain Variable Region of Humanized Antibody

Glu Ile Val Leu Thr Gln Ser Pro Ala Thr Leu Ser Leu Ser Pro Gly

Glu Arg Ala Thr Leu Ser Cys Lys Ala Ser Lys Arg Val Thr Thr Tyr

Val Ser Trp Tyr Gln Gln Lys Pro Gly Gln Ala Pro Arg Leu Leu Ile

Tyr Gly Ala Ser Asn Arg Tyr Leu Gly Ile Pro Ala Arg Phe Ser Gly

Ser Gly Ser Gly Thr Asp Phe Thr Leu Thr Ile Ser Ser Leu Glu Pro

Glu Asp Phe Ala Val Tyr Tyr Cys Ser Gln Ser Tyr Asn Tyr Pro Tyr

Thr Phe Gly Gln Gly Thr Lys Leu Glu Ile Lys

SEQ ID NO: 3--CDR H1 of Humanized Antibody

Gly Phe Thr Phe Ser Asn Tyr Trp Ile Ser

SEQ ID NO: 4--CDR H2 of Humanized Antibody

Glu Ile Arg Ser Glu Ser Asp Ala Ser Ala Thr His Tyr Ala Glu Ala

SEQ ID NO: 5--CDR H3 of Humanized Antibody

Tyr Phe Asp Tyr Gly Leu Ala Ile Gln Asn Tyr

SEQ ID NO: 6--CDR L1 of Humanized Antibody

Lys Ala Ser Lys Arg Val Thr Thr Tyr Val Ser

SEQ ID NO: 7--CDR L2 of Humanized Antibody

Gly Ala Ser Asn Arg Tyr Leu

SEQ ID NO: 8--CDR L3 of Humanized Antibody

Ser Gln Ser Tyr Asn Tyr Pro Tyr Thr

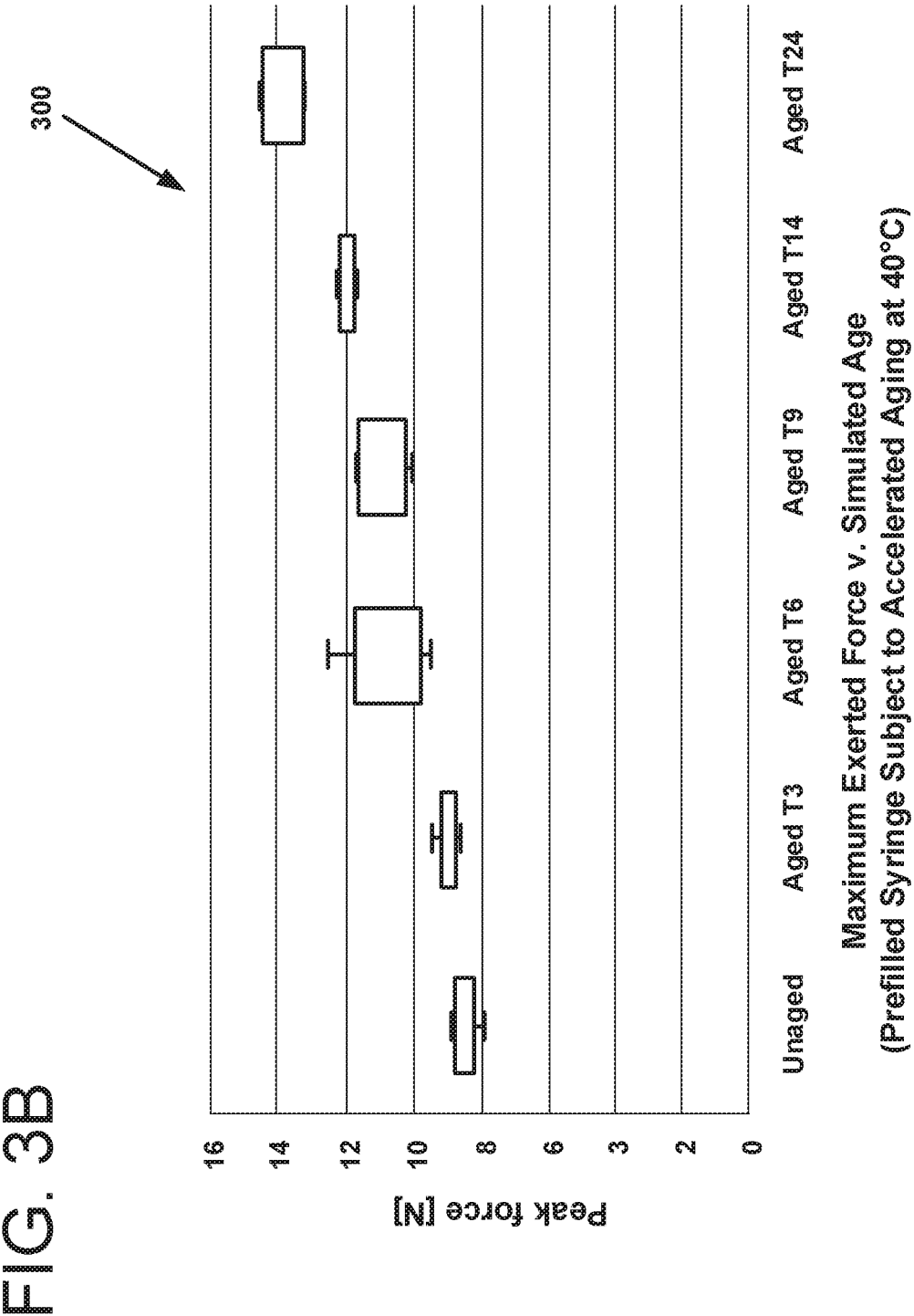

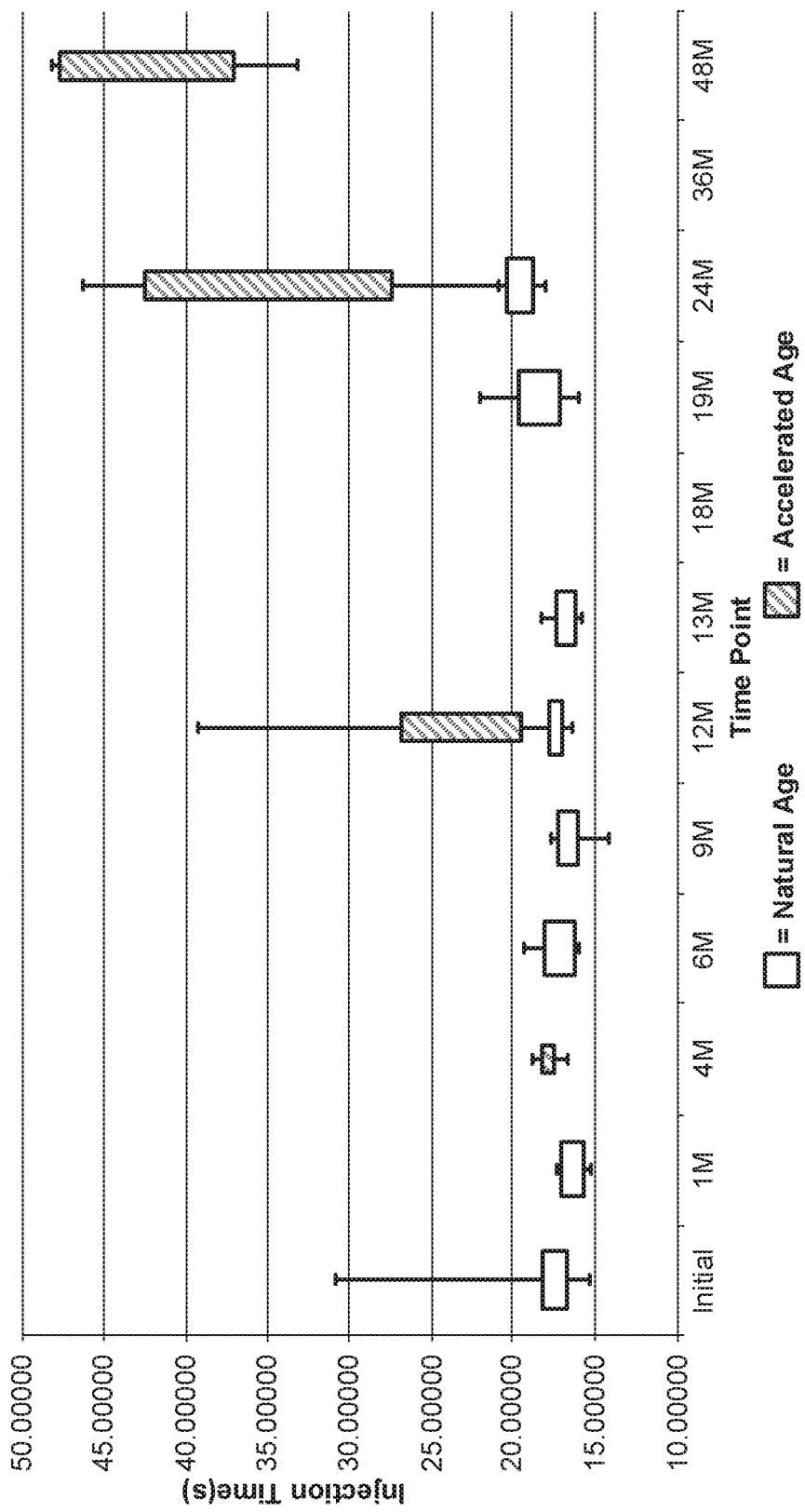

```
                        SEQUENCE LISTING

<160> NUMBER OF SEQ ID NOS: 8

<210> SEQ ID NO 1
<211> LENGTH: 122
<212> TYPE: PRT
<213> ORGANISM: Artificial Sequence
<220> FEATURE:
<223> OTHER INFORMATION: Heavy chain variable region of humanized
      antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95
```

```
Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
        115                 120
```

<210> SEQ ID NO 2
<211> LENGTH: 107
<212> TYPE: PRT
<213> ORGANISM: Artificial Sequence
<220> FEATURE:
<223> OTHER INFORMATION: Light chain variable region of humanized
     antibody

<400> SEQUENCE: 2

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105
```

<210> SEQ ID NO 3
<211> LENGTH: 10
<212> TYPE: PRT
<213> ORGANISM: Artificial Sequence
<220> FEATURE:
<223> OTHER INFORMATION: CDR H1 of humanized antibody

<400> SEQUENCE: 3

```
Gly Phe Thr Phe Ser Asn Tyr Trp Ile Ser
1               5                   10
```

<210> SEQ ID NO 4
<211> LENGTH: 19
<212> TYPE: PRT
<213> ORGANISM: Artificial Sequence
<220> FEATURE:
<223> OTHER INFORMATION: CDR H2 of humanized antibody

<400> SEQUENCE: 4

```
Glu Ile Arg Ser Glu Ser Asp Ala Ser Ala Thr His Tyr Ala Glu Ala
1               5                   10                  15

Val Lys Gly
```

<210> SEQ ID NO 5
<211> LENGTH: 11
<212> TYPE: PRT
<213> ORGANISM: Artificial Sequence
<220> FEATURE:
<223> OTHER INFORMATION: CDR H3 of humanized antibody

<400> SEQUENCE: 5

```
Tyr Phe Asp Tyr Gly Leu Ala Ile Gln Asn Tyr
1               5                   10
```

```
<210> SEQ ID NO 6
<211> LENGTH: 11
<212> TYPE: PRT
<213> ORGANISM: Artificial Sequence
<220> FEATURE:
<223> OTHER INFORMATION: CDR L1 of humanized antibody

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR L2 of humanized antibody

<400> SEQUENCE: 7

Gly Ala Ser Asn Arg Tyr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: CDR L3 of humanized antibody

<400> SEQUENCE: 8

Ser Gln Ser Tyr Asn Tyr Pro Tyr Thr
1               5
```

INJECTION SPRING FOR AGED PREFILLED SYRINGE AND AUTO INJECTOR

CROSS-REFERENCE TO RELATED APPLICATIONS

This application claims priority to U.S. Provisional Application Ser. No. 62/734,209 filed on Sep. 20, 2018, the entire disclosure of which is hereby expressly incorporated herein by reference.

BACKGROUND

An auto injector is a device for automatically injecting therapeutic fluid into a patient. Auto injectors have had rapidly increasing popularity over recent years due to a variety of factors. For example, auto injectors are convenient for both caregivers and for patients who self-administer therapeutic fluids. They decrease the number of steps required to administer therapeutic fluid. Moreover, because auto injectors are labeled and the syringes are prefilled by suppliers of the medications, there is no need to manually fill the syringe using vials of therapeutic fluid. The use of prefilled syringes reduces the risk of errors in dosage, misidentification of the medication, and contamination.

In use, an auto injector is typically loaded with a prefilled syringe and has a compressed spring or other biasing member for pushing a stopper to eject the therapeutic fluid. A button or other actuator is connected to a mechanism for releasing the compressed spring so that it extends. As the spring extends, it drives a piston rod or plunger, which in turn pushes the stopper within the syringe. The stopper then expels the therapeutic fluid from the syringe barrel, through the needle, and into the patient's tissue at the site of administration.

Before bringing a pharmaceutical product such as a prefilled syringe and auto injector on the market, a company typically must gain approval from a government regulatory agency such as the United States Food and Drug Administration or similar agency in foreign countries. For drugs contained in prefilled syringes and delivered through auto injector systems, a pharmaceutical company typically needs to provide the agency with stability testing reports, which may include a variety of information that demonstrates proper performance throughout the product shelf life. Some of the performance characteristics that must be provided might include dose accuracy within an expected injection time throughout the product shelf life.

Typically, a prefilled syringe containing the therapeutic fluid is defined early in the development process. An auto injector is later selected and an injection time of the prefilled syringe in the auto injector has to meet an expected injection time. In order to meet the expected injection time, injection time simulations are generally used. Injection time simulations are generally mathematical in nature and based on the geometry of the prefilled syringe. The geometry of the prefilled syringe notably comprises the following parameters of needle length, needle diameter, and barrel diameter. Such simulations are also generally based on parameters of the drug such as viscosity. These parameters enable simulation of the hydrodynamic forces that the fluid applies against the stopper. The Hagen-Poiseuille equation is an example of a formula that models hydrodynamic forces. Friction forces during delivery are generally approximated using step-wise functions to simulate a constant break loose force in a start of injection period and a constant gliding force in the rest of injection period.

In practice, friction forces between the prefilled syringe's stopper and barrel typically are considered as constant in injection time simulations. The constant force is typically extrapolated from a measured extrusion force on an empty prefilled syringe when the stopper is moved at a speed comparable with the speed corresponding to the expected injection time. Some more complex simulations may estimate friction forces using the formula:

$$F_{friction} = ((2\pi \mu_{oil} r_b l_{stopper})/d_{oil})\bar{v} \qquad (1)$$

where $\mu_{oil}$ is the viscosity of the lubricant, $r_b$ is the internal radius of the syringe barrel, $l_{stopper}$ is the length of the stopper in contact with the syringe barrel, $d_{oil}$ is the thickness of the lubrication, and $\bar{v}$ is the injection speed (linear piston speed with dimensions of length over time).

In general, for Newtonian fluids, neglecting the pressure drop across the syringe barrel, the hydrodynamic force can be estimated at a given temperature using the Hagen-Poiseuille equation:

$$F_{hydrodyamic} = ((8\pi \mu L_n r_b^4)/r_n^4)\bar{v} \qquad (2)$$

where $\mu$ is the viscosity of the fluid, $L_n$ is the length of the needle channel, $r_b$ is the internal radius of the syringe barrel, and $r_n$ is the internal radius of the needle channel.

Injection time simulations also are generally based on features of the auto injector, such as a dispensing force applied by the auto injector on the stopper of the prefilled syringe barrel. The dispensing force is based on the parameters and configuration of the auto injector's injection spring or other structure that powers movement of the auto injector's injection mechanism. Potential resistive forces internal to the auto injector may also be taken into account.

By calculating the forces applied to the stopper using these various mathematical models, an injection time to fulfill injection can be simulated. The simulated injection time then can be used to confirm whether the parameters and configuration of the injection spring will provide enough dispensing force against the stopper to satisfy the expected injection time.

SUMMARY

In general terms, this patent document is directed to determining a spring for an auto injector. Another aspect is directed to determining an auto injector having a determined spring.

One aspect of this patent document is a method of making an auto injector. The method comprising aging a prefilled syringe, the prefilled syringe having a stopper, measuring a force required to move the stopper within the aged prefilled syringe a determined distance within a determined time, and selecting a spring having a determined spring force, the determined spring force moving the stopper the determined distance within the determined time.

One aspect of this patent document is a method of making an auto injector to dispense a therapeutic fluid contained in an operative prefilled syringe, the operative prefilled syringe including an operative barrel and an operative stopper movably positioned within the operative barrel, the operative stopper movable along an operative path of travel from a first operative position to a second operative position, the auto injector to comprise an injection spring having a spring force, the injection spring configured to apply a dispensing force to the operative stopper by driving a piston rod toward the operative stopper upon actuation of the auto injector, the dispensing force being at least a portion of the spring force. The method comprises aging a prefilled syringe at an accelerated rate to form a reference prefilled syringe, the reference prefilled syringe including a reference barrel and a reference stopper positioned in the reference barrel; moving the reference stopper of the reference prefilled syringe along a reference path of travel from at least a first reference position to at least a second reference position; as the reference stopper moves within the reference barrel along the reference path of travel, measuring a plurality of exertion forces applied to the reference stopper and measuring a plurality of reference stopper positions; generating an exertion force profile, the exertion force profile including at least some of the exertion forces and reference stopper positions measured while the reference stopper was moving between the first and second reference positions, at least one of the measured exertion forces correlating to at least one of the measured reference stopper positions; and selecting the injection spring so that the dispensing force applied to the operative stopper at each position of the operative stopper as it moves along the operative path of travel between the first and second operative positions is greater than the measured exertion force at a corresponding one of the measured reference stopper positions.

Another aspect of this patent document also relates to an auto injector having an aged prefilled syringe, a stopper within the prefilled syringe, and an injection spring. The injection spring having a spring force with a magnitude great enough to move the stopper a determined distance.

Another aspect of this patent document is an auto injector arrangement comprising a prefilled syringe including a barrel extending along a longitudinal axis between a distal end and a proximal end, an inner diameter of the barrel being of about 8.65 mm, a needle disposed at the distal end of the barrel, the needle having an inner diameter of about 0.27 mm and a length of about 19.5 mm or less, a volume in the range from about 1.51 mL to about 1.66 mL of therapeutic fluid held within the barrel, the therapeutic fluid comprising fremanezumab, a viscosity of the therapeutic fluid being about 8.8 cSt at 22° C., and a stopper disposed within the barrel to retain the therapeutic fluid within the barrel, the barrel defining a path of travel for the stopper, the path of travel having a first initial position for the stopper and a second initial position for the stopper, the first position being an initial position of the stopper before delivery of the therapeutic fluid, the second position being a final position of the stopper upon delivery of a full dose of the therapeutic fluid. An auto injector holds the prefilled syringe. The auto injector comprises an injection spring arranged to apply a dispensing force to the stopper by driving a piston rod toward the stopper. When the auto injector is actuated, the injection spring is configured to provide an initial dispensing force to the stopper of at least about 20 N when the stopper is positioned at the first initial position and a final dispensing force of at least 12 N to the stopper when the stopper is positioned at the second final position, the dispensing force being at least a portion of a spring force for the injection spring.

Another aspect of this patent document also relates to an auto injector having an aged prefilled syringe, a stopper within the prefilled syringe, and an injection spring. The injection spring having a spring force with a magnitude great enough to move the stopper a determined distance within a determined time.

Another aspect of this patent document is an auto injector arrangement comprising a prefilled syringe. The prefilled syringe comprises a barrel formed at least in part by glass, a needle in fluid communication with the barrel, and a stopper positioned in the barrel, the barrel defining an inner surface, the barrel having an inner diameter, the barrel diameter being about 8.65 mm, the barrel defining a path of travel for the stopper, the path of travel having a first position for the stopper and a second position for the stopper, the needle having an inner diameter of about 0.27 mm and a length of about 19.5 mm or less, a therapeutic fluid held within the barrel, a viscosity of the therapeutic fluid being about 10 cP or less at 22° C. About 0.35 mg to about 1.1 mg of silicone oil lubricates the inner surface of the barrel, the silicone oil having a viscosity in a range from about 500 cSt at 25° C. to about 1500 cSt at 25° C. before the prefilled syringe is aged. An auto injector holds the prefilled syringe. The auto injector comprises a plunger and an injection spring. The plunger engages the stopper, and the injection spring biases the plunger towards the stopper. The injection spring, when in the first position, has a force determined according to the actions recited in claim 1; has a spring force in the range from about 20 N to about 30 N; has a stored spring energy in the range from about 0.9 J to about 2 J; has a spring constant in the range from about 0.2 N/mm to about 0.4 N/mm; a compressed length in the range from about 50 mm to about 100 mm; has a stored energy about 25% greater than a minimum spring energy required to move the stopper from the first position to the second position without stalling before the prefilled syringe is aged; and has a force sufficient to move the stopper along the path of travel from the first position to the second position within about 5 seconds to about 25 seconds.

Another aspect of this patent document also relates to an auto injector having an aged syringe prefilled with fremanezumab, a stopper within the prefilled syringe, and an injection spring. The injection spring having a spring force with a magnitude great enough to move the stopper a determined distance.

Another aspect of this patent document is a prefilled syringe comprising a stopper and a therapeutic fluid including fremanezumab; and an auto injector having an injection spring and a piston rod arranged to move the stopper from a first position to a second position with a force of about 30 N or less and in about 19 seconds or less, the distance between the first and second positions corresponding to one dose of the therapeutic fluid.

BRIEF DESCRIPTION OF THE DRAWINGS

FIG. 2 shows sequence listings for fremanezumab, which can be loaded in the prefilled syringe shown in FIG. 1;

FIG. 3B is a chart showing maximum exertion force measured for prefilled syringes of various artificial ages;

FIG. 3D is a chart showing injection times observed for prefilled syringes of various natural and artificial ages;

DETAILED DESCRIPTION

Figure 1:
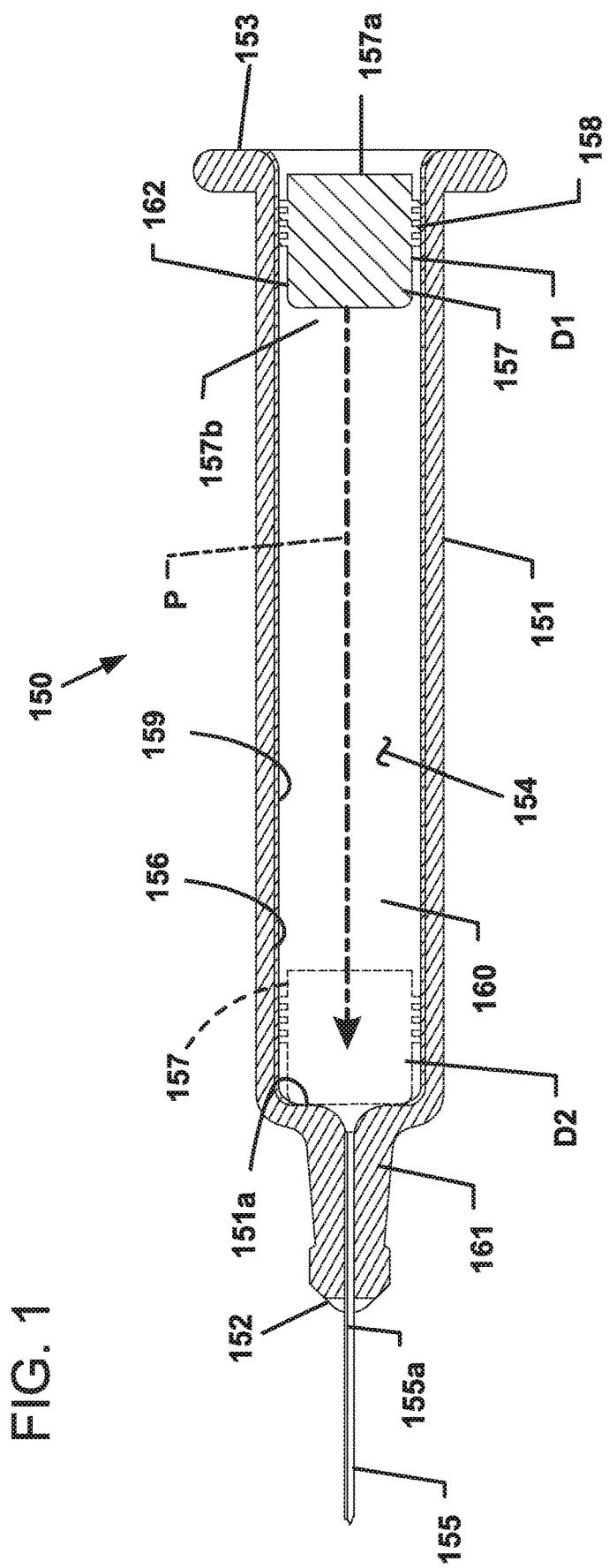
FIG. 1 is a schematic diagram of an example syringe prefilled with a fluid in accordance with the principles of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

For purposes of this patent document, the terms "or" and "and" shall mean "and/or" unless stated otherwise or clearly intended otherwise by the context of their use. Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," "including," "having," and "has" are interchangeable and not intended to be limiting. The term "such as" also is not intended to be limiting. For example, the term "including" shall mean "including, but not limited to."

All ranges provided herein include the upper and lower values of the range unless explicitly noted. Although values are disclosed herein when disclosing certain exemplary embodiments, other embodiments within the scope of the pending claims can have values other than the specific values disclosed herein or values that are outside the ranges disclosed herein.

Terms such as "substantially" or "about" when used with values or structural elements provide a tolerance that is ordinarily found during testing and production due to variations and inexact tolerances in factor such as material and equipment. These terms also provide a tolerance for variations found in nature and environmental conditions due to factors such as changes in temperature, humidity.

As used herein, the term "fremanezumab" is used interchangeably to refer to an anti-CGRP antagonist antibody produced by expression vectors having deposit numbers of ATCC PTA-6867 and ATCC PTA-6866. The amino acid sequence of the heavy chain and light chain variable regions are shown in SEQ ID NOs: 1 and 2, respectively. The CDR amino acid sequences of the G1 heavy chain variable region are shown in SEQ ID NOs: 7-9 (Kabat and Chothia CDRs are indicated). The CDR amino acid sequences of the G1 light chain variable region are shown in SEQ ID NOs: 10-12. Exemplary polynucleotides encoding the G1 heavy and light chain variable regions are shown in SEQ ID NO: 5 and SEQ ID NO: 6, respectively. The G1 heavy chain full length amino acid sequence is shown in SEQ ID NO: 3. The G1 light chain full length amino acid sequence is shown in SEQ ID NO: 4. Exemplary polynucleotides encoding the G1 full length heavy chain and light chains are shown in SEQ ID NO: 3 and SEQ ID NO: 4, respectively. The characterization of G1 is described in PCT Publication No. WO 2007/054809 and WHO Drug Information 30(2): 280-1 (2016), which are hereby incorporated by reference in its entirety.

FIG. 1 illustrates an example embodiment of a prefilled syringe 150 suitable for holding a therapeutic fluid 160 for injection. The prefilled syringe 150 includes a barrel 151, a needle 155, and a stopper 157. The barrel 151 defines an interior 154 sized to hold a predetermined amount of the fluid 160 (e.g., at least one dose of the therapeutic fluid). The fluid 160 is held within the interior 154 of the barrel 151 between the stopper 157 and the needle 155. An example of a syringe that can be used for the prefilled syringe 150 is a 2.25 mL EZ-Fill syringe supplied by Ompi (Piombino Dese, Italy). Other types of syringes can be used and syringes from other manufacturers also can be used.

The barrel 151 extends between a distal end 152 and an open proximal end 153. The prefilled syringe 150 also has a tip 161 at the distal end 152. The barrel 151 defines a proximally facing shoulder 151a at the distal end 152 of the interior 154 that extends between the barrel 151 and the tip 161.

The syringe barrel 151 is configured to hold about 2.25 mL of fluid. However, other barrel sizes can be utilized. For example, the barrel 151 can be sized to hold about 1 mL of fluid. In other embodiments, the barrel 151 is sized to a volume of therapeutic fluid 160 in the range from about 1 mL to about 3 mL, about 1 mL to about 2.5 mL, or about 2 mL to about 2.5 mL. Other embodiments of the prefilled syringe 150 can hold other volumes of therapeutic fluid 160.

Additionally, the syringe barrel 151 has an inner diameter or other inner cross-dimension of about 8.65 mm. In alternative embodiments, however, the barrel 151 can have an inner diameter in the range from about 6 mm to about 10 mm, or from about 8.5 mm to about 8.8 mm. Yet other possible embodiments can have an inner diameter other than in these ranges.

In certain examples, the syringe barrel 151 is formed from Borosilicate glass. In certain examples, the syringe barrel 151 is formed from clear, type I Borosilicate glass. For example, the syringe barrel 151 can be composed of a mixture of $SiO_2$, $B_2O_3$, $Al_2O_3$, $Na_2O$, and CaO. In a more specific example, the syringe barrel 151 is formed with 75% $SiO_2$, 10.5% $B_2O_3$, 5% $Al_2O_3$, 7% $Na_2O$, and 1.5% CaO. Alternative embodiments with other mixtures of these materials can be used to form the glass for the syringe barrel 151.

Other embodiments can use other types of glass or even materials other than glass to form the syringe barrel 151. For example, the syringe barrel 151 can be formed with plastic. In at least some embodiments, the syringe barrel 151 is a Borosilicate glass barrel supplied by Schott Corporation of Elmsford, N.Y. Syringe barrels 151 from other manufacturers can be used.

The stopper 157 is axially moveable within the interior 154 of the barrel 151 along a path of travel, P, in a distal direction. The stopper 157 has a main body that is substantially cylindrical or otherwise has a cross-section shape similar to a cross-section of the inner surface 156 for the barrel 151. The stopper 157 has one or more flanges or ribs 158 that extend radially from the main body. Additionally, the stopper 157 has a compressed state and an uncompressed state, the stopper 157 is in the compressed state when it is inserted into the syringe barrel 151.

The main body of the stopper 157 has a first engagement surface 157a facing an exterior of the prefilled syringe 150 in a proximal direction and a second engagement surface 157b facing the fluid 160 contained within the barrel 151. The first engagement surface 157a is flat and the end of a piston rod (e.g., 107 of FIGS. 14-17) abuts the engagement surface 157a during use. In alternative embodiments, the first engagement surface 157a may include a threaded hole (not shown) or other connection structure (not shown) so that the stopper 157 can be threaded onto or otherwise connected to the end of a piston rod in the auto injector. To move the stopper 157 distally within the syringe barrel 151, a dispensing force can be applied to the first engagement surface 157a of the stopper 157 to push the stopper 157 along the path of travel, P. The main body of the stopper 157 has a length of about 7.7 mm. In alternative embodiments, the stopper 157 may have a length in the range from about 7.3 mm to about 8.1 mm, or from about 7 mm to about 9 mm. Alternative embodiments of the stopper 157 can have a length that is longer or shorter than these ranges. Additionally, the outer diameter of the main body for the stopper 157 when it is in the compressed state is about 8.95 mm. In some alternative embodiments, the outer diameter of the main body is in the range from about 8.85 mm to about 9.05 mm, or from about 5.5 mm to about 9.5 mm. Alternative embodiments can have a main body with an outer diameter that is outside of these ranges. Additionally, the outer diameter is measured from the base of a flange 158, across the main body to the base of the flange 158 on the opposite side of the main body.

The plurality of annular flanges 158 engage the inner surface 156 of the syringe barrel 151. The flanges 158 create a substantially air-tight seal against the inner surface 156 of the syringe barrel 151 and holds the therapeutic fluid 160 within the interior 154. The stopper 157 includes four flanges 158. In alternative embodiments, the stopper 157 may have a greater or lesser number of flanges 158. For example, the stopper 157 could have one flange, two flanges, three flanges, or more than four flanges. Alternative embodiments might also include no flanges so that the entire outer surface 162 between the first and second engagement surfaces 157a, 157b engages the inner surface 156 of the syringe barrel 151. In the compressed state, the stopper 157 has an outer diameter or cross-dimension of about 8.95 mm. In alternative embodiments, the outer diameter of the stopper 157 in the compressed state may be in the range from about 6 mm to about 10 mm, or from about 6.5 mm to about 9.5 mm. In some examples, the outer diameter of the stopper 157 is the outer diameter across the largest portion of the stopper 157 (e.g., across at least one of the flanges 158), and it is at least slightly larger than the inner diameter or inner cross-dimension of the syringe barrel 151 to ensure a seal between the two. When in the uncompressed state, at least some possible embodiments of the stopper 157 have an outer diameter in the range from about 9.25 mm to about 9.45 mm.

The stopper 157 is formed from a rubber such as Bromobutyl rubber, although materials other than rubber or other than Bromobutyl can be used to form the stopper 157. An example formulation that can be used to form the Bromobutyl rubber, such as the formulation 4023/50/GREY from West Pharmaceutical Services, PA, USA. Other formulations are possible. In other embodiments, material other types of rubber or material other than rubber is used to form the stopper 157. Additionally, the stopper 157 can have a fluoropolymer coating on its outer surface 162 or have a laminated outer surface 162. In an example, the coating can cover the entire outer surface 162 of the stopper 157. In an alternative example, the coating can cover some or all of the second engagement surface 157b, some or all of the flanges 158, some or all of the portions of the outer surface 162 that opposes the inner surface 156 of the syringe barrel 151, some or all of first engagement surface 157a, or combinations of these surfaces. An example of the fluoropolymer material that can be used to coat the stopper 157 is ethylene tetrafluoroethylene (ETFE). An advantage of coating the stopper 157 with fluoropolymer is that it prevents absorption or adsorption of the therapeutic fluid 160.

Material other than fluoropolymer can be used to coat or laminate the stopper 157. An example of an alternative material is silicone. Alternatively, the stopper 157 can be coated or laminated with two or more materials. For example, the stopper 157 can have fluoropolymer coating the portion of its surface that comes into contact with the therapeutic fluid 160, and silicone oil coating the portion of its surface that does not come into contact with the therapeutic fluid 160. The coatings on the stopper 157 can operate as a lubricant, provide increased biocompatibility with the therapeutic fluid 160, prevent absorption or adsorption of the therapeutic fluid 160 or its constituents, or a combination of the foregoing. In yet other embodiments, the stopper 157 does not have any type of coating or lamination.

In use, the second engagement surface 157b of the stopper 157 pushes the fluid 160 towards the needle 155 to expel the fluid 160 from the prefilled syringe 150. The stopper 157 is moved from a first position, D1, along a path of travel, P to a second position, D2, along the path of travel, P. In an example embodiment, the first position, D1, is a position adjacent to the fluid 160 before any amount of a dose of the therapeutic fluid 160 is delivered, and the second position, D2, is the location of the second engagement surface 157b upon completing delivery of a complete dose of the therapeutic fluid 160. When in the second position, D2, the stopper 157 is directly adjacent or even touching the shoulder 151a of the syringe barrel 151. In an alternative embodiment, there can be a gap or air bubble between the therapeutic fluid 160 and the stopper 157 when the stopper 157 is in the first position, D1, or the stopper 157 can be spaced from the shoulder 151a of the syringe barrel 151 when the stopper 157 is in the second position, D2.

The path of travel, P, can be about 29.6 mm, which is sometimes referred to as a "30 mm" path of travel. In alternative embodiments, the path of travel, P, can be in the range from about 25.7 mm to about 28.2 mm, from about 25 mm to about 29 mm, or from about 25 mm to about 40 mm. In some embodiments, the path of travel, P, can be 29.6 mm. In other embodiments, the length of the path of travel, P, can be a distance outside these ranges. A volume of therapeutic fluid 160 in the prefilled syringe 150 that is held in the prefilled syringe 150 between the first and second positions D1, D2 of the stopper 157 is about 1.585 mL, which corresponds directly to the interior volume of the syringe barrel 151 between the first and second positions D1, D2. In alternative embodiments, the volume of fluid 160 between the first and second stopper 157 positions D1, D2 is in the range from about 1.51 mL to about 1.66 mL. Alternative embodiments can have different volumes of fluid 160 between the first and second positions D1, D2 of the stopper 157. The volume of fluid 160 may correspond to one full dose of therapeutic fluid 160, multiple doses of the therapeutic fluid 160, or a partial dose of the therapeutic fluid 160.

The force applied to the stopper 157 by the auto injector 140 is the dispensing force. The amount of dispensing force required to push the stopper 157 in the prefilled syringe 150 can vary due to a variety of factors. Examples of such factors include the lubrication 159, the syringe geometry and material, the stopper geometry and material, the therapeutic fluid 160 in the prefilled syringe 150, desired injection time, and other resistive forces that oppose movement of the stopper 157. Additionally, because the stopper 157 is compressible, it can absorb some of the dispensing force applied to it by the piston rod of an auto injector 140. The selected injection spring would have to have enough force to overcome this absorption if absorption becomes significant enough to affect performance of the auto injector 140.

Lubrication 159 may be disposed along an inner surface 156 of the barrel 151 to facilitate movement of the stopper 157 within the barrel 151. The lubrication 159 is disposed between the inner surface 156 of the barrel 151 and an outer contact surface 162 of the stopper 157 as the stopper 157 moves along the path of travel P. The lubrication 159 reduces the friction between the outer contact surface 162 of the stopper 157 and the inner surface 156 of the barrel 151.

The lubricant used to form the layer of lubrication 159 is a silicone oil. An example of silicone oil that can be used is polydimethylsioxane. In alternative embodiments, a lubricant other than silicone oil, a silicone oil other than polydimethylsioxane, or any other suitable lubricant is used to lubricate the inner surface 156 of the barrel 151. The lubrication 159 can cover the entire inner surface 156 of the syringe barrel 151 including the wall of the barrel 151 and the shoulder 151a. In other examples, the lubrication 159 covers less than the entire inner surface 156 of the prefilled syringe 150 such as only along the wall of the barrel 151, or only along those portions of the wall of the barrel 151 that extend along the path of travel, P.

In at least some embodiments, the layer of lubrication 159 has a substantially uniform thickness along the path of travel P. Alternatively, the layer of lubrication 159 has a substantially uniform thickness along substantially the entire length of the syringe barrel 151. Additionally, in at least some embodiments, the layer of lubrication 159 has a substantially uniform thickness around the inner circumference of the syringe barrel 151. In other embodiments, the thickness of the layer of lubrication 159 varies over the length of the syringe barrel 151 or along the path of travel P. For example, the thickness of the lubrication 159 can gradually thin toward the distal end 152 of the prefilled syringe 150 compared to the proximal end 153 of the prefilled syringe 150. As discussed in more detail herein, the thickness of the lubrication 159 can have other variations and also can vary around the circumference of the syringe barrel 151.

In possible embodiments, the thickness of the lubrication layer 159 is about 0.5 μm. Other thicknesses are possible. For example, the lubrication layer 159 may have a thickness between about 0.1 μm and about 1 μm along the path of travel, P. In other examples, the lubrication layer 159 may have a thickness between about 0.1 μm and about 0.3 μm along the path of travel, P.

In at least some embodiments, the prefilled syringe 150 includes about 0.7 mg of silicone oil to form the lubricating layer 159. In other embodiments, the amount of silicone oil is in the range from about 0.4 mg to about 1.1 mg. In yet other embodiments, the amount of silicone oil is in the range from about 0.35 mg to about 1.0 mg.

In an example embodiment, the lubricant forming the lubrication layer 159 has a viscosity of about 1000 cSt at 25° C. In an alternative embodiment, the lubricant has a viscosity in the range from about 500 cSt to about 1000 cSt at 25° C., from about 100 cSt to about 1000 cSt at 25° C., or less than about 1250 cSt at 25° C. In yet other embodiments, the lubricant has a viscosity outside of these ranges.

The needle 155 is disposed at the distal end 152 of the barrel 151 and is connected to the tip 161. The needle 155 is secured to the tip 161 with an adhesive. In alternative embodiments, the needle 155 is connected to the tip 161 using a hub or other structure.

The needle 155 extends between a first end and a second end. The needle 155 is connected to the distal end 152 of the syringe barrel 151 at or adjacent to the first end of the needle 155. The second end of the needle 155 may be sufficiently sharp or pointed to assist in breaking skin 192 at an injection site 198 of a user 190 (see FIG. 19). The needle 155 defines a channel 155a that is in fluid communication with the interior 154 of the prefilled syringe 150. In operation, fluid 160 flows through the channel 155a to exit the syringe barrel 151. The channel 155a of the needle 155 has an internal diameter or cross-dimension, which is the distance from one point on the periphery to another point on the opposite side of the periphery. An internal diameter is an example of the cross-dimension when the channel 155a is circular in cross-section. In an example, the channel 155a has a constant internal diameter or cross-dimension along a length of the needle 155. In other embodiments, however, the internal diameter or cross-dimension can vary along the length of the channel 155a.

The needle 155 is a stainless steel needle such as a Grade AISI 304 stainless steel needle supplied by Chirana T. Injecta of Slovakia. Additionally, the needle 155 has an ISO-name 4301-304-00-1 and an ISO designation X5CrNi18-9. Other materials can be used to form the needle 155. Other embodiments can use needles 155 from other manufacturers, and needles 155 having alternative ISO certifications or no certification at all.

The needle 155 has a length of 19.5 mm. In alternative embodiments, the needle 155 can have a length in the range from about 15 mm to about 25 mm, from about 18.3 mm to about 20.7 mm, or less than 19.5 mm. Other embodiments can have a needle length that is longer or shorter than these ranges. Additionally, the needle channel 155a has an inner diameter or inner cross-dimension of 0.27 mm, from about 0.15 mm to about 0.3 mm, from about 0.25 mm to about 0.29 mm, from about 0.21 mm to about 0.3 mm, or less than 0.27 mm. In other embodiments, the needle 155 has an inner diameter of about 0.29 mm or less. Other embodiments have an inner diameter that is narrower or wider than these ranges.

The therapeutic fluid 160 can contain drugs having pharmacological or other active ingredients, biologics, biosimilars, or any other composition for treating a body. Depending on the composition of the therapeutic fluid 160 and prescribed treatment, the therapeutic fluid 160 can have one of a variety of different volumes and viscosities. In at least some possible embodiments, for example, the therapeutic fluid 160 has a volume of about 1.585 mL. In other embodiments, the volume of therapeutic fluid 160 is in the range from about 1.51 mL to about 1.66 mL. In other embodiments, the volume of therapeutic fluid 160 is in the range from about 1 mL to about 2.25 mL. Yet other embodiments have other volumes of therapeutic fluid 160 loaded in the prefilled syringe 150.

The therapeutic fluid 160 may be a liquid pharmaceutical composition comprising fremanezumab, disodium ethylenediaminetetraacetic acid dihydrate (EDTA), L-histidine, L-histidine hydrochloride monohydrate, polysorbate-80, sucrose, and water for injection. An example of a particular formula for the therapeutic fluid 160 is about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection at a pH of about 5.5. In an alternative embodiment, the therapeutic fluid 160 can be formulated at 150 mg/mL nominal concentration in 16 mM histidine, 6.6% sucrose, 0.136 mg/mL EDTA, 1.2 mg/mL P580, pH 5.5. In some embodiments, at least about 70% of the fremanezumab in the liquid pharmaceutical composition is of the IgG2-B disulfide isoform. In some embodiments of any of the compositions provided herein, about 72% of the antibody molecules in the composition are of the disulfide isoform B, wherein about 22% of the antibody molecules in the composition are of the IgG2-A/B, and wherein about 6% of the antibody molecules in the composition are of the IgG2-A disulfide isoform. Other embodiments of the therapeutic fluid 160, including those for fremanezumab, can have other formulations including other constituents. Additionally, the therapeutic fluid 160 can have drugs, biologics, or biosimilars other than fremanezumab.

The viscosity of the liquid pharmaceutical composition may be about 8.8 cSt at 22° C. Other viscosities are possible. For example, the therapeutic fluid 160 may have a viscosity ranging from about 4 cSt at 22° C. to about 14 cSt at 22° C. In certain examples, the therapeutic fluid 160 has a viscosity ranging from about 8 cP at 22° C. to about 10 cP at 22° C. In certain examples, the therapeutic fluid 160 has a viscosity less than about 10 cSt at 22° C.

The therapeutic fluid 160 can be used for the treatment or prevention of a variety of different temporary or chronic diseases, conditions, or other maladies. The therapeutic fluid 160 can be used for the treatment or prevention of any disease or disorder associated with CGRP (Calcitonin Gene-Related Peptide) activity or CGRP upregulation. In one possible embodiment, the therapeutic fluid 160 comprises a biologic such as for treating episodic or chronic migraine headaches. For example, the therapeutic fluid 160 can include a immunoglobulin $G_2$ (IgG2) monoclonal antibody. In another example, the therapeutic fluid 160 includes a humanized IgG2 monoclonal antibody. The antibody also may be expressed in CHO cells. In another example, the therapeutic fluid 160 includes an anti-CGRP protein.

In a more specific example, and with reference to FIG. 2, the therapeutic fluid 160 includes an antibody comprising a heavy chain variable region $V_H$ domain that is at least 90%, optionally 95%, 97%, 99%, or 100% identical in amino acid sequence to SEQ ID NO: 1 and a light chain variable region $V_L$ domain that is at least 90%, optionally 95%, 97%, 99%, or 100% identical in amino acid sequence to SEQ ID NO: 2. In certain examples, the therapeutic fluid 160 includes the antibody produced by the expression vectors with ATCC Accession Nos. PTA-6867 and PTA-6866. In another example, the therapeutic fluid 160 includes fremanezumab.

In other examples, the therapeutic fluid 160 includes an antibody comprising the following CDRs: CDR H1 as set forth in SEQ ID NO: 3; CDR H2 as set forth in SEQ ID NO: 4; CDR H3 as set forth in SEQ ID NO: 5; CDR L1 as set forth in SEQ ID NO: 6; CDR L2 as set forth in SEQ ID NO: 7; and CDR L3 as set forth in SEQ ID NO: 8.

The therapeutic effects of fremanezumab are long lasting and can be taken by injection relatively infrequently. In one embodiment, for example, fremanezumab can be administered about one time per month or less frequently. In another example, fremanezumab can be administered about once every two months or less frequently. In another example, fremanezumab can be administered about once every three months or less frequently. In another example, fremanezumab can be administered about once every four months or less frequently. Fremanezumab is disclosed in more detail in U.S. Pat. No. 8,007,794, which issued on Aug. 30, 2011, and is entitled "Antagonist Antibodies Directed Against Calcitonin Gene-Related Peptide and Methods Using the Same", the entire disclosure of which is hereby incorporated herein by reference.

The therapeutic fluid 160 also can be used for the treatment or prevention of other conditions such as cluster headaches, posttraumatic headaches, fibromyalgia, and Interstitial Cystitis/Bladder Pain Syndrome (ICBPS).

In certain implementations, the therapeutic fluid 160 is expected to have a shelf life of about 24 months when stored between 2° C. and 8° C. In an example, the therapeutic fluid 160 is expected to have a shelf life of about 2 years when stored at 5° C. In other embodiments, the therapeutic fluid 160 is expected to have a shelf life of at least 12 months when stored between 2° C. and 8° C. In certain examples, the therapeutic fluid 160 is expected to have a shelf life of at least 18 months when stored between 2° C. and 8° C. In certain examples, the therapeutic fluid 160 is expected to have a shelf life of at least 30 months when stored between 2° C. and 8° C. In certain examples, the therapeutic fluid 160 is expected to have a shelf life of at least 36 months when stored between 2° C. and 8° C. In certain examples, the therapeutic fluid 160 is expected to have a shelf life of at least 6 months when stored between 2° C. and 8° C. In certain examples, the therapeutic fluid 160 is expected to have a shelf life of at least 9 months when stored between 2° C. and 8° C.

It has been discovered that traditional injection time simulations for prefilled syringes 150 have several disadvantages. For example, several aspects of a prefilled syringe 150 change over time and, given enough time, some of the changes can cause significant problems with performance of the prefilled syringe 150 and an auto injector 140 in which the prefilled syringe 150 is mounted. Many of these changes are not commonly taken into account by current injection time simulations, and can include changes to the prefilled syringe 150 that increase resistive forces opposing movement of the stopper 157 within the syringe barrel 151.

The increase in resistive forces can be great enough to slow the speed of the syringe stopper 157 within the syringe barrel 151 compared to the prefilled syringe 150 before the changes occurred. Sometimes, the speed of injection due to these increased resistive forces may cause discomfort to the patient. The slow injection also could result in an impatient user 190, who is self-administering the therapeutic fluid 160, to pull the needle 155 out of their body prematurely, thereby resulting in an incomplete delivery of the fluid 160. In yet another embodiment, movement of the stopper 157 can even stall, resulting in delivery of only a partial dose.

Friction and hydrodynamic forces are examples of resistive forces that oppose movement of the stopper 157 and may affect the break-loose force and glide force, and thereby the injection time and dose accuracy. The break-loose force is the amount of force required to set the stopper 157 in motion, and the glide force is the amount of force required to sustain movement of the stopper 157. Friction can be between the stopper 157 and the syringe barrel 151. Other types of friction also can oppose movement of the stopper 157. Hydrodynamic force is the force required to push the fluid 160 through the barrel 151, into the needle 155, and then through the needle 155.

There are several changes that can occur over time and increase friction between the stopper 157 and syringe barrel 151. For example, the lubrication 159 in the syringe barrel 151 or on the stopper 157 can degrade or breakdown, whether due to time or interaction with the constituents of the therapeutic fluid 160. The degradation of the lubrication 159 can cause the viscosity of the lubrication 159 to increase. The degradation also can cause the layer of lubrication 159 on the barrel wall 156 to thin over time. Furthermore, the lubrication 159 is a fluid and flows along the barrel wall 156 over time, which can cause variations in the thickness of the lubrication 159 resulting in areas of increased friction along the stopper's path of travel, P, because the layer of lubrication 159 thins or is gone entirely.

There also are several examples of changes that can increase hydrodynamic forces. For example, some therapeutic fluids 160 can change over time. The therapeutic fluid 160 can aggregate or crystalize over time forming larger clumps that can become stuck in the channel 155a of the hypodermic needle 155. The blockage created by these clumps may increase the hydrodynamic force required to move the fluid 160 through the needle 155. The result is greater resistance against movement of the stopper 157.

If a developer of therapeutic fluids or prefilled syringes wants to use actual, real world data to design an auto injector or to use for regulatory approval, they may choose to test a prefilled syringe that has been aged at least as long as its desired shelf life. A problem with using actual, real world data is that many therapeutic fluids and prefilled syringes are expected to have a long shelf life, some as long as 24 months or even longer.

Waiting this long to submit an application for regulatory approval of a drug delivered by an auto injector until after the natural shelf life of the therapeutic fluid lapses can significantly delay the approval process for the medication and the time at which the pharmaceutical company can put the therapeutic fluid on the market. As a result, potentially life-altering or even life-saving medications are delayed in reaching patients. In addition, this delay makes it more difficult for the pharmaceutical company to recover the huge investment required to research and find a successful medication. To speed up the regulatory approval process, the pharmaceutical companies may use simulated or accelerated aging to replicate the effects of time. For example, the pharmaceutical company can use mathematical modeling to approximate the performance of a prefilled syringe after a certain period of time. In another example, the pharmaceutical companies heat the prefilled syringe at a determined temperature and for a determined period of time to simulate aging. The relationship between the length of time heating the prefilled syringe and the actual, non-accelerated length of time can be defined according to the Arrhenius calculation:

$$K = Ae^{-EA/(RT)} \quad (3)$$

where "K" is the rate constant, "T" is the absolute temperature (in Kelvin), "$Ae^{-EA}$" are constants for a given reaction, and "R" is a universal gas constant.

It was discovered that artificial aging of the prefilled syringes 150 or the therapeutic fluid 160 can lead to complications during stability testing. For example, during stability testing using artificial aging, it was discovered that the combination of an aged prefilled syringe 150 and an auto injector (e.g., the auto injector 140 shown in FIGS. 13-17) could result in various operation failures, including failure to inject within the intended injection time. It was further discovered that artificial aging of the prefilled syringe 150 led to higher than expected resistive forces on the stopper 157. For example, the resistive force exerted on the stopper 157 towards the end of an injection stroke along the path of travel, P, was higher than expected. Accordingly, the injection spring 109 used in a standard auto injector device was not able to consistently successfully operate the auto injector with the artificially aged prefilled syringe 150 as the simulated aging increased.

In particular, it was discovered that heating the prefilled syringe 150 exaggerates certain changes that occur over time. For example, heating causes changes to the prefilled syringe 150 to occur faster than they would during an equivalent amount of time for natural aging. For example, when compared to a prefilled syringe 150 that is naturally aged at a non-accelerated rate for 24 months, a prefilled syringe 150 subject to accelerated aging by heating for a simulated 24-month period will show changes of a greater magnitude or even more types of changes, such as changes to the thickness of the lubricating layer 159, greater decreases to the viscosity of the lubricant, greater variations in the thickness of the lubricating layer 159, more interaction between the therapeutic fluid 160 and the lubricant, and the like.

All of these exaggerated changes that occur during artificial or accelerated aging unnaturally increase friction and hydrodynamic forces as compared to a prefilled syringe 150 that ages naturally. When an artificially aged prefilled syringe 150 having increased resistance to movement of the stopper 157 is combined with an auto injector (e.g., the auto injector 140 described in more detail herein), there can be operational failures including failure to inject the therapeutic fluid 160 within the intended injection time or even injection stalls. Yet the pharmaceutical company must show data that the auto injector 140 can move the stopper 157 to deliver a full dose of the therapeutic fluid 160 within a reasonable period of time and not stall. To enable an effective regulatory path by allowing artificial aging and meeting stability requirements, it is herein proposed to adapt the auto injector 140. An injection spring 109 for the auto injector 140 that has enough spring force to meet acceptable delivery specifications for an artificially aged prefilled syringe 150 is used. However, it is noted that the prefilled syringes used in the auto injectors on the market will be naturally aged. Further, it is noted that increasing unnecessarily the spring force is generally not beneficial because it may lead to some discomfort, bruising of the patient, or breakage of the prefilled syringe.

An example of this problem with artificially aged prefilled syringes 150 is illustrated in the charts shown in FIGS. 3A-3D. To generate the data shown in FIGS. 3A-3D, the prefilled syringes 150 used were 2.25 mL EZ-Fill syringes with an internal barrel diameter of about 8.65 mm supplied by Ompi of Piombino Dese, Italy, the stopper 157 was a FluroTec plunger from West Pharmaceutical Services, PA of Exton, Pa., USA, and the needle 155 was a Grade AISI 304 stainless steel needle supplied by Chirana T. Injecta of Slovakia with an internal diameter of about 0.27 mm and a length of about 19.5 mm. The syringe barrels 151 were lubricated with 0.7 mg of silicone oil having a viscosity of about 1000 cSt at 25° C. The therapeutic fluid 160 loaded in the prefilled syringes 150 consisted of about 1.585 mL of a formulation of fremanezumab formulated at 150 mg/mL nominal concentration in 16 mM histidine, 6.6% sucrose, 0.136 mg/mL EDTA, and 1.2 mg/mL P580 at a pH of 5.5. The therapeutic fluid 160 had a viscosity of 8.8 cSt at 22° C. Multiple unaged prefilled syringes 150 were tested. The path of travel, P, of the stopper 157 in the barrel 151 corresponding to the extrusion of the therapeutic fluid 160 is of about 30 mm.

Figure 3A:
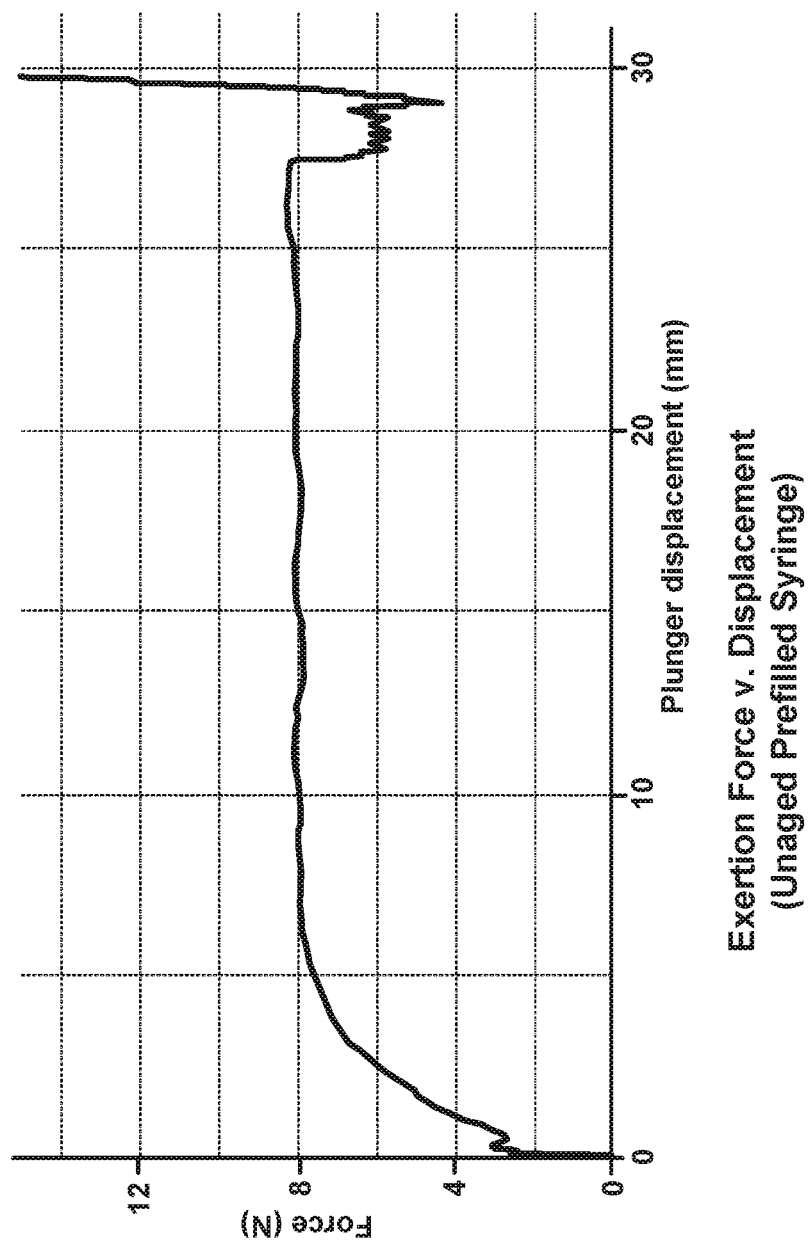
FIG. 3A is a graph plotting one set of measured exertion forces against displacement of the drive member acting on a stopper of an unaged prefilled syringe.

FIG. 3A is a graph plotting the force exerted against the syringe stopper 157 of an unaged prefilled syringe 150 versus displacement of the stopper 157 when the stopper 157 is moved at a constant speed. The graph may be obtained using the test equipment described with reference to FIGS. 4A and 5. The y-axis shows the force exerted against the stopper 157 measured in Newton, N. Because the stopper 157 is moved at a substantially constant speed, this exertion force is substantially equal to the resistive force that acts against movement of the stopper 157. The displacement is the displacement from a first (initial) position of the stopper 157 at the beginning of an injection and a second (final) position of the stopper 157. The chart in FIG. 3A shows the maximum resistance force during movement of the stopper 157 is about 8 N until just before the displacement reaches about 30 mm, which corresponds to the stopper 157 reaching and hitting the shoulder 151a in the syringe barrel 151.

FIG. 3B is a bar chart showing the maximum force exerted on the stopper 157 of a prefilled syringe 150 subjected to accelerated aging. The prefilled syringes 150 exposed to accelerated aging were heated at 40° C. for a period of time equivalent to simulate a desired natural age. For each prefilled syringe 150, the stopper 157 was pressed for extruding the therapeutic fluid 160 at a constant speed and the force exerted against the stopper 157 was measured. The force exerted against the stopper 157 is equivalent to or corresponds to the force resistive to movement of the stopper 157. The graph was obtained using the test equipment described with reference to FIGS. 4A and 5. The y-axis shows the maximum force exerted against the syringe stopper 157 in Newton while it is moved to deliver a dose of therapeutic fluid 160 at a constant speed. The x-axis shows the simulated age of the prefilled syringe 150 after it goes through accelerated aging. The first bar shows the maximum exertion force before accelerated aging. The second bar shows the maximum exertion force for a prefilled syringe 150 that has a simulated age of 3 months (T3). The third bar shows the maximum exertion force for a prefilled syringe 150 that has a simulated age of 6 months (T6). The fourth bar shows the maximum exertion force for a prefilled syringe 150 that has a simulated age of 9 months (T9). The fifth bar shows the maximum exertion force for a prefilled syringe 150 that has a simulated age of 14 months (T14). The sixth bar shows the maximum exertion force for a prefilled syringe 150 that has a simulated age of 24 months (T24).

As can be seen, the maximum force measured while moving the stopper 157 during testing gradually increases to about 14 N, which is much greater than the 8 N measured for an unaged prefilled syringe 150. Each bar on the chart represents a group of prefilled syringes 150 tested at each simulated age and shows the range of measured exertion forces for the group from the highest maximum exertion force measured to the lowest maximum exertion force measured for the group. Each bar also presents a box representing the middle two quartiles or the middle 50% of the measured exertion forces.

Figure 3C:
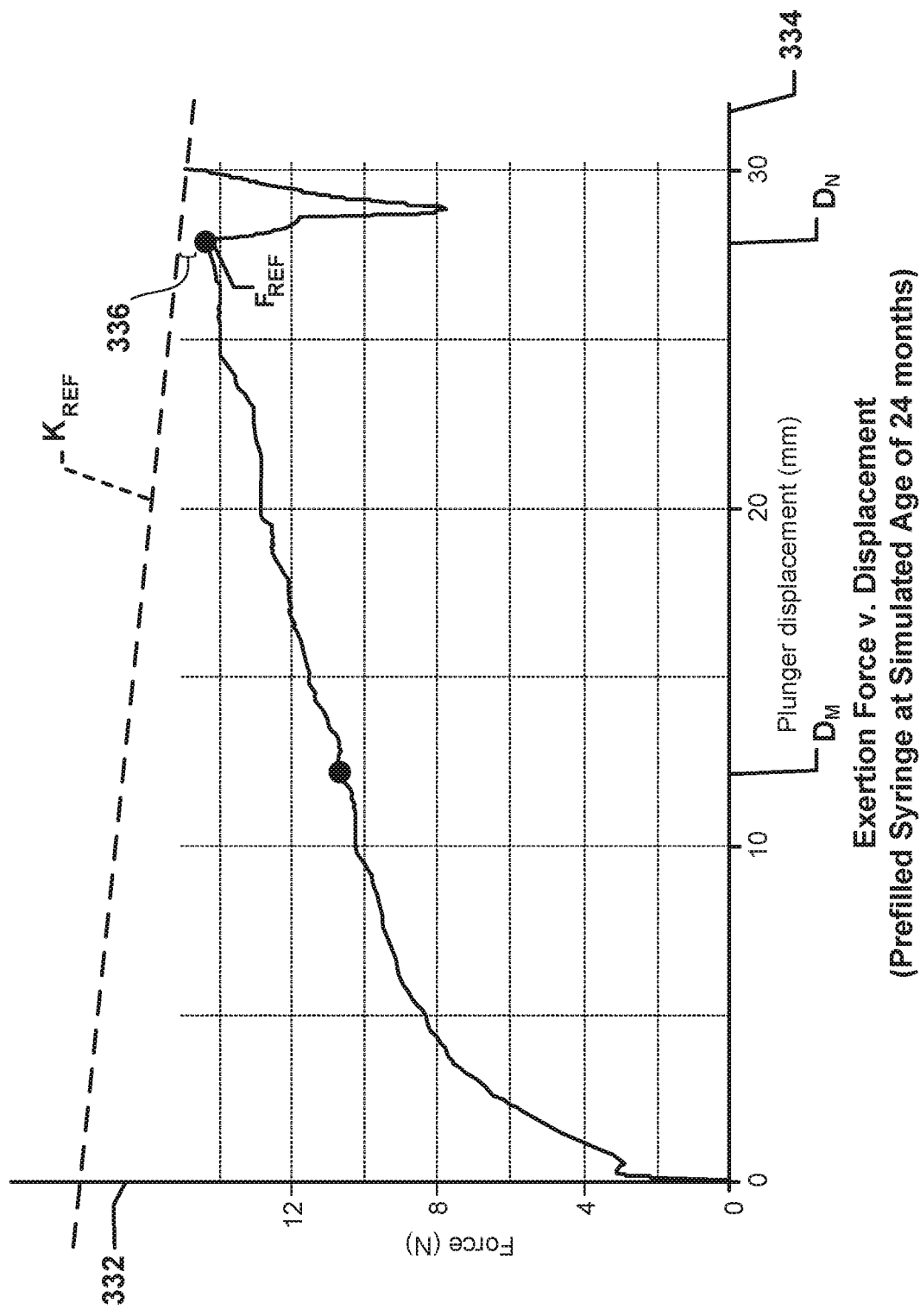
FIG. 3C is a graph plotting one set of measured exertion forces against displacement of the drive member acting on a stopper of a prefilled syringe artificially aged to 24 months.

FIG. 3C is a graph plotting the force exerted against the syringe stopper 157 of a prefilled syringe 150 having a simulated age of 24 months versus displacement of the stopper 157. The prefilled syringes 150 exposed to accelerated aging were heated at 40° C. for a period of time equivalent to simulate a desired natural age. For each prefilled syringe 150, the stopper 157 was pressed for extruding the therapeutic fluid 160 at a constant speed and the force exerted against the stopper 157 was measured. The force exerted against the stopper 157 is equivalent to or corresponds to the force resistive to movement of the stopper 157. The y-axis shows the force exerted against the stopper 157 measured in Newton, N. The graph was obtained using the test equipment described with reference to FIGS. 4A and 5. Because the stopper 157 moves at a substantially constant speed, this exertion force is substantially equal to the resistive force that acts against movement of the stopper 157. The displacement is the displacement from a first position of the stopper 157 at the beginning of an injection and the ending position of the stopper 157. The chart in FIG. 3C shows the maximum resistance force during movement of the stopper 157 is about 14 N until just before the displacement reaches 30 mm, which corresponds to the stopper 157 reaching and hitting the shoulder 151a in the syringe barrel 151.

As can be seen in FIGS. 3B and 3C, the peak or maximum force required to move the stopper 157 a distance of 30 mm for a prefilled syringe 150 that had a simulated or accelerated age of 24 months was in the range from about 13 N to about 14 N. The peak force for the accelerated aged prefilled syringe 150 is in sharp contrast to the only 8 N to 9 N peak force required to move the stopper 157 of the naturally aged prefilled syringe 150 as shown in FIG. 3A. These charts show a significant increase in the force required to move the stopper 157 for an artificially aged prefilled syringe 150 used in testing compared to a naturally aged prefilled syringe 150.

FIG. 3D is a bar chart showing injection time or how long it takes to move the stopper 157 from the first position, D1, to the second position, D2, for prefilled syringes 150 subject to natural aging and prefilled syringes 150 subject to accelerated aging. The y-axis shows the injection time in seconds, and the x-axis shows the age of the prefilled syringe 150. Data for naturally aged prefilled syringes 150 is shown with bars without a cross hatch, and data for accelerated aged prefilled syringes 150 is shown with bars with a cross hatch. To generate the data in FIG. 3D, an auto injector 140 with a prefilled syringe 150 was mounted in a fixture, which held the auto injector 140 upright with the needle 155 pointed down. A container was placed under the auto injector 140 to collect fluid 160 as it was dispensed. The auto injector 140 was actuated. A stopwatch was manually started simultaneously with actuating the auto injector 140 and stopped immediately when therapeutic fluid 160 stopped flowing from the needle 155. A digital stop clock having an accuracy of within 100th of a second was used. Eight samples of naturally aged prefilled syringes 150 were tested at zero months, 1 month, 6 months, 9 months, 13 months, 19 months, and 24 months. Four samples of accelerated aged prefilled syringes 150 were tested at 12 months, 24 months, and 48 months. Each bar on the chart represents a group of prefilled syringes 150 tested at a natural age or a simulated age as labelled on the chart and shows the range of injection time for each group from the longest injection time to the shortest injection time. Each bar also presents a box representing the middle two quartiles or the middle 50% of the injection times.

At 12 months, the naturally aged prefilled syringes 150 had an injection time in the range from about 18.6 s to about 20.8 s, whereas the accelerated aged prefilled syringes 150 had an injection time in the range from about 16.4 s to about 39.3 s. At 24 months, the naturally aged prefilled syringes 150 had an injection time in the range from about 18 s to about 21 s, whereas the accelerated aged prefilled syringes 150 had an injection time in the range from about 19.4 s to about 46.3 s. As can be seen, the delivery time for a naturally aged prefilled syringe 150 remains relatively steady throughout the life of the prefilled syringe 150. The delivery time for an artificially aged prefilled syringe 150 is comparable to the delivery time for a naturally aged prefilled syringe 150 until the prefilled syringe 150 is about 9 months old. After that age, the time for delivery of a full dose starts to rapidly increase for the artificially aged prefilled syringes 150. At 24 months of simulated aging, the delivery time can reach more than 45 seconds, which exceeds a target delivery time.

The above-described tests and results show that artificial aging of a prefilled syringe 150 can result in an increase in the force required to complete an injection. In certain cases, artificial aging of a prefilled syringe 150 can result in an increase in the force required to complete an injection within a desired or determined period of time (e.g., from about 5 seconds to about 19 seconds).

As a solution to these operation failures, the auto injector 140 may be manufactured with an injection spring 109 that is sufficiently strong to accommodate the higher extrusion forces on the stopper 157 of an artificially aged prefilled syringe 150. That is, the injection spring 109 may need a sufficiently high spring constant K and compression to overcome the increased resistive forces generated by an artificially aged prefilled syringe 150, especially at the end of injection as the stopper 157 approaches the second position, D2, and the resistive force is significantly greater than the resistive force at the beginning of injection, as can be seen in FIG. 3B. However, increasing the strength of the injection spring 109 can lead to discomfort or even bruising of the patient. It also can lead to breakage of the syringe 150. Accordingly, using an injection spring 109 having more power than necessary is undesirable.

The tests described below can be used in determining suitable spring parameters for the injection spring 109 of an auto injector 140 used to inject therapeutic fluid 160 from an artificially aged prefilled syringe 150. For example, the tests can determine a dispensing force that is sufficiently strong to displace the syringe stopper 157 fully along the entire path of travel, P, within a predetermined time. The artificially aged prefilled syringe 150 used in these tests forms a reference prefilled syringe 150 having a reference barrel 151, a reference stopper 157, and a reference needle 155. The prefilled syringe 150 that is actually used in an auto injector 140 to deliver the therapeutic fluid 160 to a patient is an operative prefilled syringe 150 having an operative barrel 151, an operative stopper 157, and an operative needle 155. The reference prefilled syringe 150 is substantially similar to the operating prefilled syringe 150. To ensure proper performance of the operative prefilled syringes 150, the reference prefilled syringes 150 and the operative prefilled syringes 150 have substantially the same dimensions and are made from the same materials or materials that provide the same performance characteristics. In an alternative embodiment, the reference prefilled syringes 150 and operative prefilled syringes 150 can have different parameters. For example, the reference prefilled syringe 150 can have parameters that provide more resistive force against movement of the stopper 157, which ensures that the designed injection spring 109 will still provide a suitable amount of dispensing force throughout the entire range of spring compression so that the auto injector 140 will inject a full dose of therapeutic fluid 160 within the determined time.

Figure 4A:
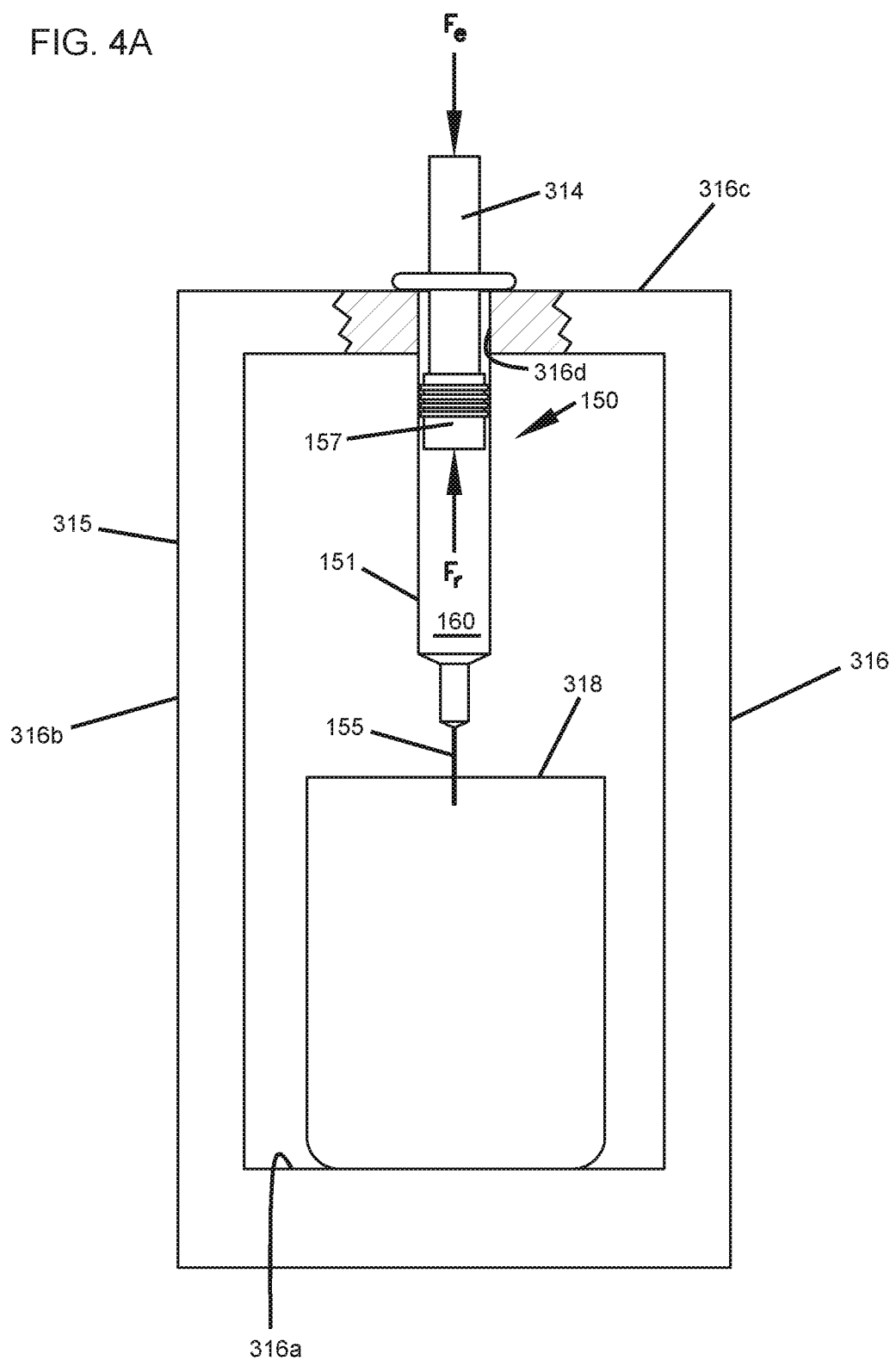
FIG. 4A is a side elevational view in partial cross-section showing a fixture for testing a prefilled syringe.
Figure 4B:
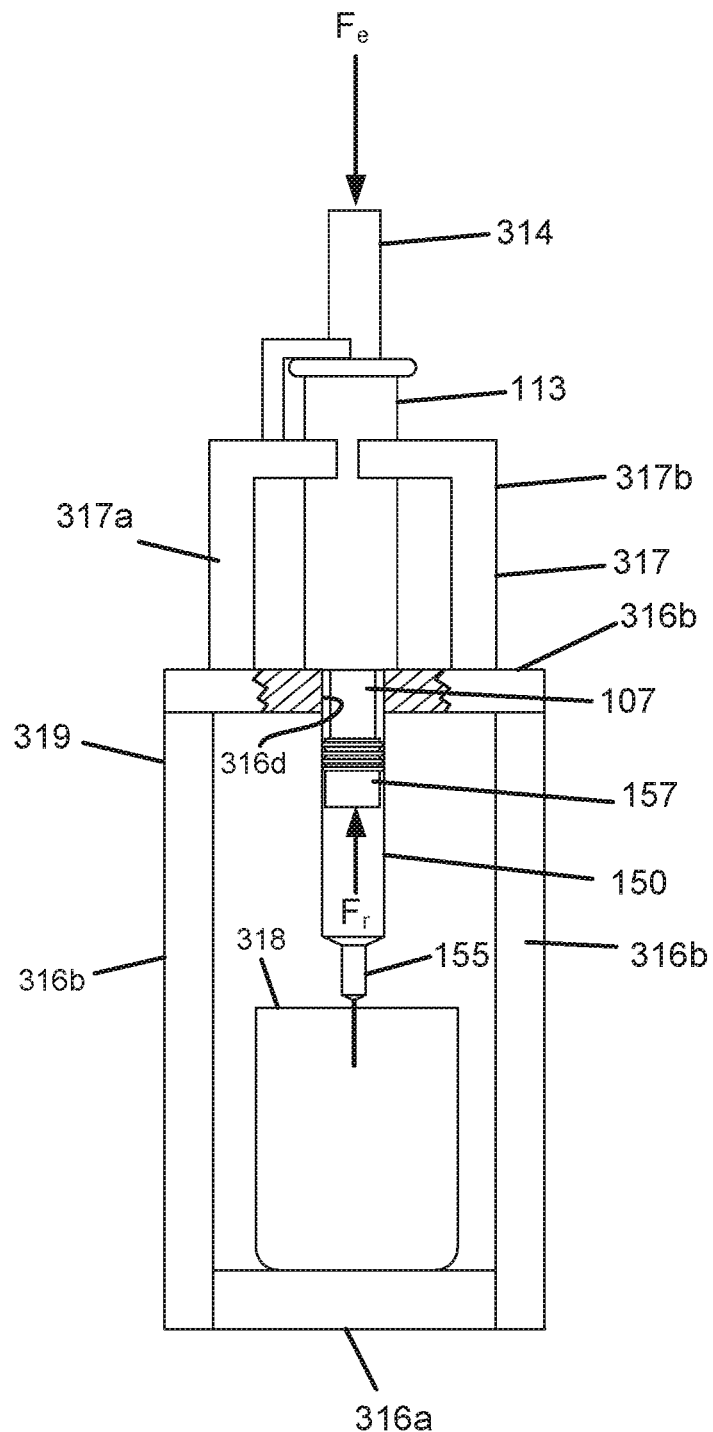
FIG. 4B is a side elevational view in partial cross-section showing an alternative fixture for testing a prefilled syringe and auto injector mechanism.

FIGS. 4A and 4B illustrate a fixture for testing injection of prefilled syringes 150 to determine an injection spring 109 having sufficient force to meet performance criteria for regulatory approval of prefilled syringes 150 and auto injectors 140. FIG. 4A illustrates a fixture 315 for holding a prefilled syringe 150 and also illustrates the principles of the test. The fixture 315 includes a syringe support frame 316 having a bottom support 316a, side supports 316b, and a top plate 316c. The syringe support frame 316 is of sufficient thickness and rigidity so that it does not flex or compress under application of the forces used in testing. The top plate 316c defines a hole 316d that is large enough so the syringe barrel 151 will pass through the hole 316d, but not so large that the syringe flange 158 at the proximal end 153 of the prefilled syringe 150 will fit through the hole 316d. In this way, the prefilled syringe 150 is supported by the top plate 316c with the needle 155 pointed down. A drive rod 314 is aligned with and has an end that engages the first engagement surface 157a of the syringe stopper 157. A second, opposite end of the drive rod 314 is coupled to testing equipment configured to move the drive rod 314 at a substantially constant speed. The drive rod 314 also is attached to measuring equipment such as a load cell 315 (see, e.g., FIG. 5) that is positioned to measure a force applied to the drive rod 314 as it moves.

The needle 155 is positioned in or above a collection container 318 to collect the therapeutic fluid 160 as it is ejected from the prefilled syringe 150. Collecting the therapeutic fluid 160 allows a comparison of the amount of fluid 160 loaded in the prefilled syringe 150 before testing to the amount of fluid 160 ejected from the prefilled syringe 150 after testing to ensure a full dose is ejected during testing. Alternatively, the tip 161 of the needle 155 can be inserted into a mass to simulate injection into a patient. Inserting the tip 161 of the needle 155 into a mass enables the test apparatus to include the resistance to flow in its measurements of total resistance acting against movement of the syringe stopper 157. Examples of a mass that can simulate an injection include cadaver tissue, animal tissue such as pig, and synthetic tissue.

During the test, the drive rod 314 is advanced or pushed against the stopper 157 to push the stopper 157 for a consistent speed and for a determined distance. In at least some possible embodiments, the determined distance corresponds to the stopper 157 moving from the first position, D1, to the second position, D2, to deliver a full dose of therapeutic fluid 160. The speed at which the drive rod 314 is pushed downward is selected to simulate a desired timing for injection of the prefilled syringe 150 within an auto injector 140. In some embodiments, the drive rod 314 is advanced from the first position, D1, to the second position, D2, at a time in the range from about 5 s to about 12 S.

As the drive rod 314 is advanced against the syringe stopper 157, the load cell 315 measures the force applied to the drive rod 314 and the relative position of the drive rod 314 is measured. The displacement of the drive rod 314 will substantially equal the displacement of the syringe stopper 157. The force measurements and the displacement of the drive rod 314 at the time of each force measurement are recorded.

During testing, the force applied to the drive rod 314 to advance or push the syringe stopper 157 is an exertion force, Fe. Forces that oppose movement of the stopper 157 due to friction, hydrodynamics, and any force that resists movement of the stopper 157 is a resistive force, Fr. Because the stopper 157 moves at a substantially constant speed during the test, the exertion force will substantially equal a resistive force. The exertion force may vary during advancement of the stopper 157 due to changing resistive forces acting against movement of the stopper 157.

FIG. 4B illustrates an alternative fixture 319 for testing prefilled syringes 150 in combination with an auto injector 140. This embodiment is substantially similar to the fixture in FIG. 4A, and includes the syringe support frame 316, which is supporting the prefilled syringe 150. Additionally, a clamp 317 is mounted on the top plate 316c of the syringe frame 316 and includes first and second opposing jaws 317a, 317b. Each of the first and second jaws 317a, 317b defines opposing contours such as semicircular cutouts, which are shaped to receive and securely hold a portion of the auto injector 140 when the jaws 317a, 317b are closed. In operation, an auto injector 140 has its injection spring 109 removed and is mounted in the clamp 317 and is positioned so the piston rod 107 from the auto injector 140 is axially aligned with the syringe barrel 151. The piston rod 107 is inserted into the syringe barrel 151 so that the end of the piston rod 107 for the auto injector 140 engages the first engagement surface 157a of the stopper 157.

As described in more detail herein, the auto injector 140 includes a subassembly that moves in response to decompression of the injection spring 109. The subassembly will include a structure for advancing the piston rod 107. The subassembly also may include additional moving structures and secondary spring mechanisms that also are moved or driven by the injection spring 109 as it decompresses. In example embodiments, the entire auto injector 140, minus the injection spring 109, can be mounted in the clamp 317 provided there is access to insert the drive rod 314 into the auto injector 140 so that it can engage and move the piston rod 107 and other auto injector components that operate in response to movement of the piston rod 107. Alternatively, the subassembly can be removed from the auto injector 140 or otherwise exposed and mounted in the clamp 317 without components of the auto injector 140 that are not operated by the injection spring 109.

The drive rod 314 connected to the test equipment engages and moves the piston rod 107 at a constant speed for a determined distance. In at least some embodiments, the determined distance corresponds to the distance the stopper 157 is moving from the first position, D1, to the second position, D2, to deliver a full dose of the therapeutic fluid 160. The exertion forces applied to the drive rod 314 and the displacement of the drive rod 314 are recorded. In this test setup, the measured exertion force may correspond to the total resistance force including friction in the prefilled syringe 150, hydrodynamic forces, friction in the subassembly, any force required to compress secondary springs in the subassembly, and any other resistive force that acts against movement of the stopper 157 and movement of the subassembly.

Figure 4C:
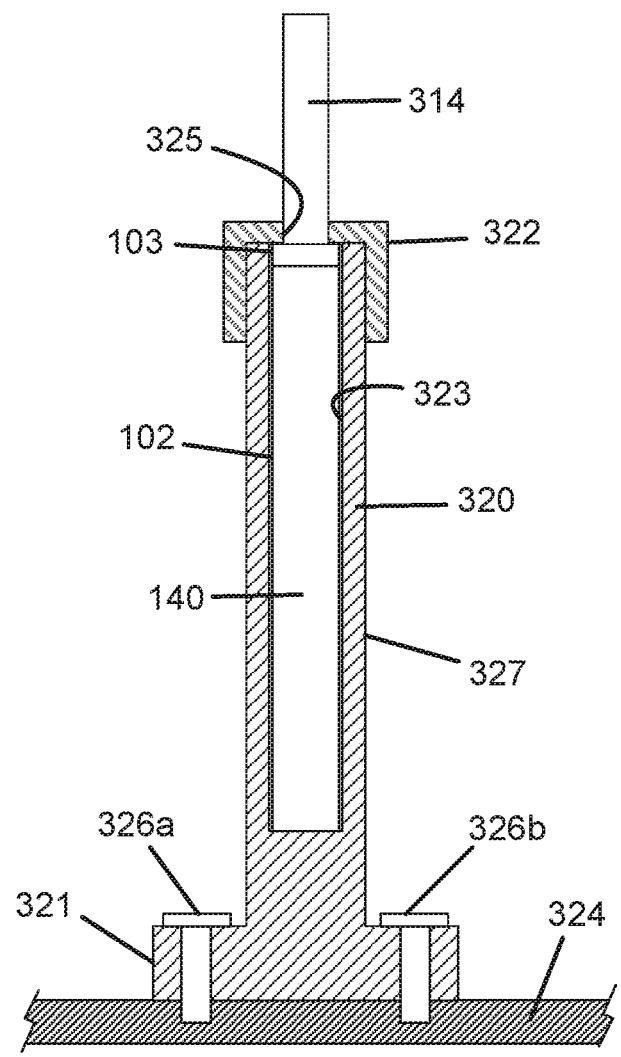
FIG. 4C is a side cross-sectional view of a fixture for testing spring forces in an auto injector.

FIG. 4C illustrates a fixture 320 for testing an auto injector 140 to determine the spring strength for the injection spring 109. It is used to simulate operation of the auto injector 140 and measure the dispensing force of the piston rod 107 as the injection spring 109 decompresses. It is useful to verify proper operation of an auto injector 140 after an injection spring 109 is selected as described in more detail herein.

The fixture 320 includes a base 321 that can be secured to a workbench 324 for stability during testing. The base 321 is secured to the workbench 324 using bolts 326a, 326b. A tube 327 extends upward from the base 321 and defines a cavity 323 that is sized to receive an auto injector 140. The length of the cavity 323 is about the same length of the housing 104 for the auto injector 140, although in various embodiments it can be longer or shorter. The cross-sectional shape and area of the cavity 323 is sized to allow the auto injector 140 to slide into the cavity 323, but still hold the auto injector 140 securely without twisting or wobbling. A cap 322 is secured over the top end of the tube 327 to enclose and secure the auto injector 140 within the cavity 323. The cap 322 defines a hole 325 that is axially aligned with the cavity 323 and sized to receive the drive rod 314.

As explained in more detail herein, the auto injector 140 has a housing 102 and cover sleeve 103 that telescopes into the housing 102 (see, e.g., FIGS. 13-17). Sliding the cover sleeve 103 into the housing 102 cocks the auto injector 140 so that the internal piston rod 107 is free to move. To test the auto injector 140 in fixture 320, the prefilled syringe 150 is removed from the auto injector 140 so that the piston rod 107 is exposed. The auto injector 140 is then inserted in the cavity 323 and orientated so that the cover sleeve 103 points upward and extends from the top of the tube 327. The cap 322 is placed over the end of the tube 327. The drive rod 314 is then inserted through the hole 325 and into the auto injector 140 so that the end of the drive rod 314 engages the end of the piston rod 107. A second, opposite end of the drive rod 314 is coupled to testing equipment configured to move the drive rod 314 at a substantially constant speed. The drive rod 314 also is attached to measuring equipment such as a load cell 315 (see, e.g., FIG. 5) that is positioned to measure a force applied to the drive rod 314 as it moves.

The cap 322 is then pushed down until the cover sleeve 103 telescopes into the housing 102, which cocks the auto injector 140 and frees the injection spring 109 to decompress and the piston rod 107 to move. The cap 322 is locked onto the end of the tube 327 so it stays in place. Any suitable mechanism can be used to secure the cap 322 in place. For example, the cap 322 can be threaded onto the end of the tube 327. Alternatively, the tube 327 can include a key that projects form the side of the fixture 320 and the cap 322 can include an L-shaped slot that receives the key and holds the cap 322 in place. The methods and testing apparatuses disclosed herein also can be used to test alternative embodiments of spring-driven auto injectors.

At the start of the test, the injection spring 109 is compressed and the piston rod 107 is in a position that corresponds to the stopper 157 being in its first position. The drive rod 314 is then raised at a constant speed and for a determined distance. In at least some possible embodiments, the determined distance corresponds to the stopper 157 moving from the first position, D1, to the second position, D2, to deliver a full dose of therapeutic fluid 160. For example, the drive rod 314 can be raised about 30 mm. Additionally, the speed at which the drive rod 314 is raised is selected to simulate a desired timing for injection of the prefilled syringe 150 within an auto injector 140. As the drive rod 314 is raised and the piston rod 107 advances, the load cell 315 measures the force applied to the drive rod 314 and the relative position of the drive rod 314. The displacement of the drive rod 314 will substantially equal the displacement of the syringe stopper 157. The force measurements and the displacement of the drive rod 314 at the time of each force measurement are recorded to form a dispensing force profile. Such force measurements can be used to verify the injection spring 109 causes the piston rod 107 to exert a desired dispensing force as it advances between positions corresponding to the first and second positions D1, D2 of the stopper 157.

Although the fixture 320 is illustrated as holding an auto injector 140 having a telescoping sleeve 103 to cock the auto injector 140 and free the piston rod 107 to move, it can be adapted to hold and cock auto injectors 140 having alternative mechanisms such as push buttons, knobs, levers, and sliding buttons.

Figure 5:
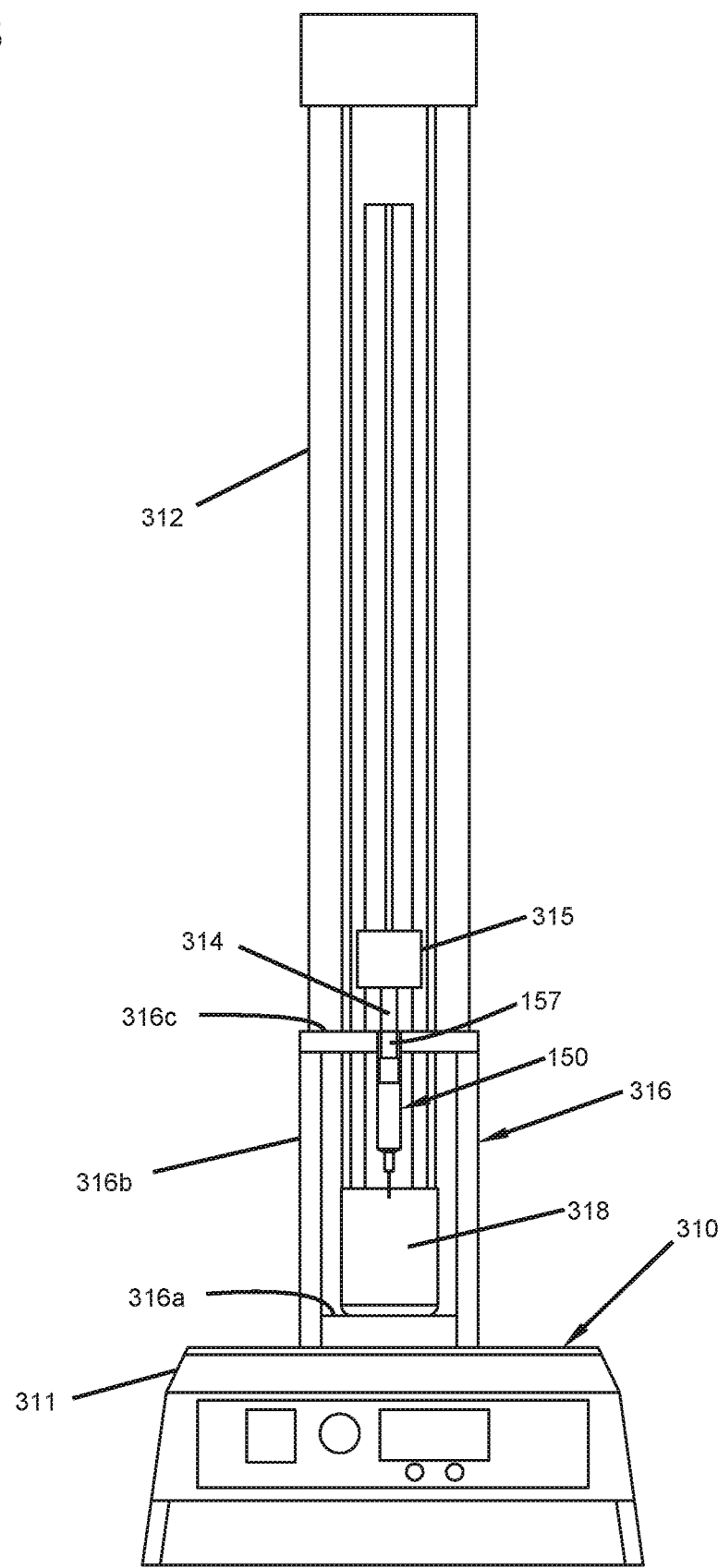
FIG. 5 is a side elevational view of an instrument for measuring performance of prefilled syringes and auto injectors for use with the fixtures illustrated in FIGS. 4A-4C.

FIG. 5 illustrates the fixture 315 shown in FIG. 4A in a test setup for operating the drive rod 314 and measuring performance of the prefilled syringe 150. In this set up, a universal testing machine 310 has a cross head 312 that moves up and down and can be moved a constant and determined speed. The fixture 316 is mounted in the universal testing machine 310 and positioned so that the drive rod 314 is axially aligned with cross head 312. A load cell 315 is positioned between the drive rod 314 and the cross head 312 and measures the force exerted against the drive rod 314 as the cross head 312 moves downward or otherwise advances toward the stopper 157. Additionally, a gauge for measuring displacement of the cross head 312 or drive rod 314 is positioned and configured to measure movement of the cross head 312. As noted herein, linear movement of the cross head 312 and drive rod 314 will be substantially equal to linear movement of the syringe stopper 157. Although the fixture 316 is illustrated being used with the universal testing machine 310, it should be appreciated that the fixture 319 illustrated in FIG. 4B and the fixture 320 illustrated in FIG. 4C can be used with the universal testing machine 310 and drive rod 314 in a substantially similar manner.

The load cell 315, gauge, and universal testing machine 310 are operated by a programmable controller 311 such as a computer that controls movement of the cross head 312 and records output from the load cell 315 an instrument for measuring distance. Measurements from the load cell 315 and the gauge are synchronized so that the recorded exertion force is correlated to the displacement of the drive rod 314/stopper 157 at the time a force measurement is made. The force and displacement measurements form an exertion force profile correlating the measured force to displacement of the drive rod 314 and stopper 157. This data can be used to generate graphs and charts similar to those illustrated in FIGS. 3A-3C. The computer controller 311 also can record the time intervals for each measurement made and the total time it takes to fully displace the stopper 157 for delivery of a full dose of therapeutic fluid 160.

The load cell 315 can be any type of instrument or sensor that measures force such as a strain gauge or piezo electric cell. The gauge can be any type of instrument for measuring distance including light-, laser-, and magnetic-based measuring instruments. The gauge also could be virtual in that the motor driving the cross head 312 is a stepper motor and distance is determined by the number of steps during rotation of the armature on the motor. An example of a universal testing machine 310 that can be used is a MultiTest 2.5-I tensometer available from Mecmesin of the United Kingdom. An example of a load cell 315 may be of 25N or 200N. An example of control software may be Emperor v1.18. Other universal machines that can be adapted to measure force and displacement can be used. In operation, and as discussed herein, the programmable controller 311 controls the universal testing machine 310 to move the cross head 312 at a substantially constant speed. Alternative embodiments can apply acceleration or deceleration to movement of the cross head 312. In an alternative test setup, the fixture 320 holding both the prefilled syringe 150 and auto injector 140 can be used with the universal testing machine 310.

It is desirable to select an injection spring 109 for an auto injector 140 that has enough force to apply a dispensing force against the stopper 157 and to also operate the related subassemblies in the auto injector 140 within a determined time, such as about 19 seconds, when the prefilled syringe 150 is subjected to accelerated aging so that the spring 109 specifications can be used in the regulatory approval process. It is also desirable to select a spring 109 that is not too strong and deliver the therapeutic fluid 160 too fast for a commercialized auto injector 140 and prefilled syringe 150 combination, especially because the effects of natural aging are not as significant as they are for artificial aging. The dispensing force is that portion of the spring force that is applied to the stopper 157 during operation of the auto injector 140, the remaining portion of the spring force operates any subassembly that is also driven by the injection spring 109.

FIGS. 6-11 illustrate various methods to determine an injection spring 109 having enough stored energy to: (i) move the syringe stopper 157 a desired distance along the path of travel, P, within a determined time; (ii) have enough stored energy to maintain a relatively steady speed movement as the stopper 157 approaches the second position, D2, to prevent the stopper 157 from stalling; and (iii) operate components in the auto injector 140 other than the piston rod 107 that also are powered by the injection spring 109. Examples of components in the auto injector 140 that are powered by the injection spring 109 include the piston rod 107, the holding pin 106, and the holding sleeve 108, which the spring 109 holds distally against the bias of the cover sleeve spring 110. In yet other alternative embodiments, the only structure moved by decompression of the injection spring 109 is the syringe stopper 157 itself. The portion of the syringe force that is applied to the stopper 157 through the piston rod 107 is a dispensing force. The remaining portion of the spring force that is used to operate mechanisms in the auto injector 140 other than the piston rod 107 is an operation force.

Figure 6:
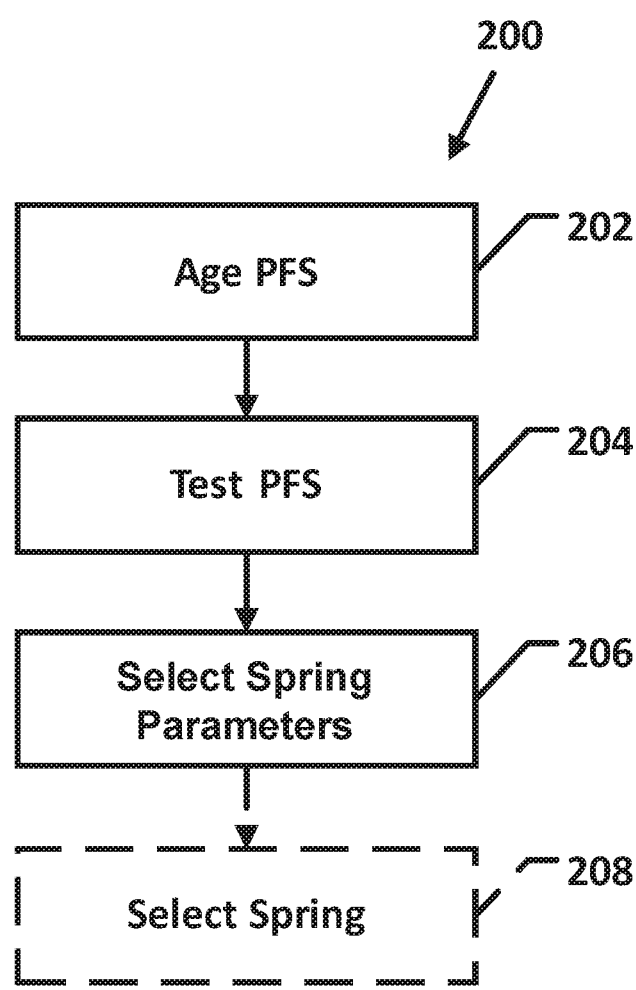
FIG. 6 is a flowchart illustrating a determination process by which a spring constant can be selected for the injection spring of an auto injector.

FIG. 6 is a flowchart illustrating a determination process 200 by which parameters can be selected for the injection spring 109 of an auto injector 140. Examples of parameters for the injection spring 109 include the spring constant, uncompressed spring length, and compressed spring length. The determination process 200 includes an age operation 202, a test operation 204, and a select operation 206. The determination process 200 optionally may include a second select operation 208.

Figure 7:
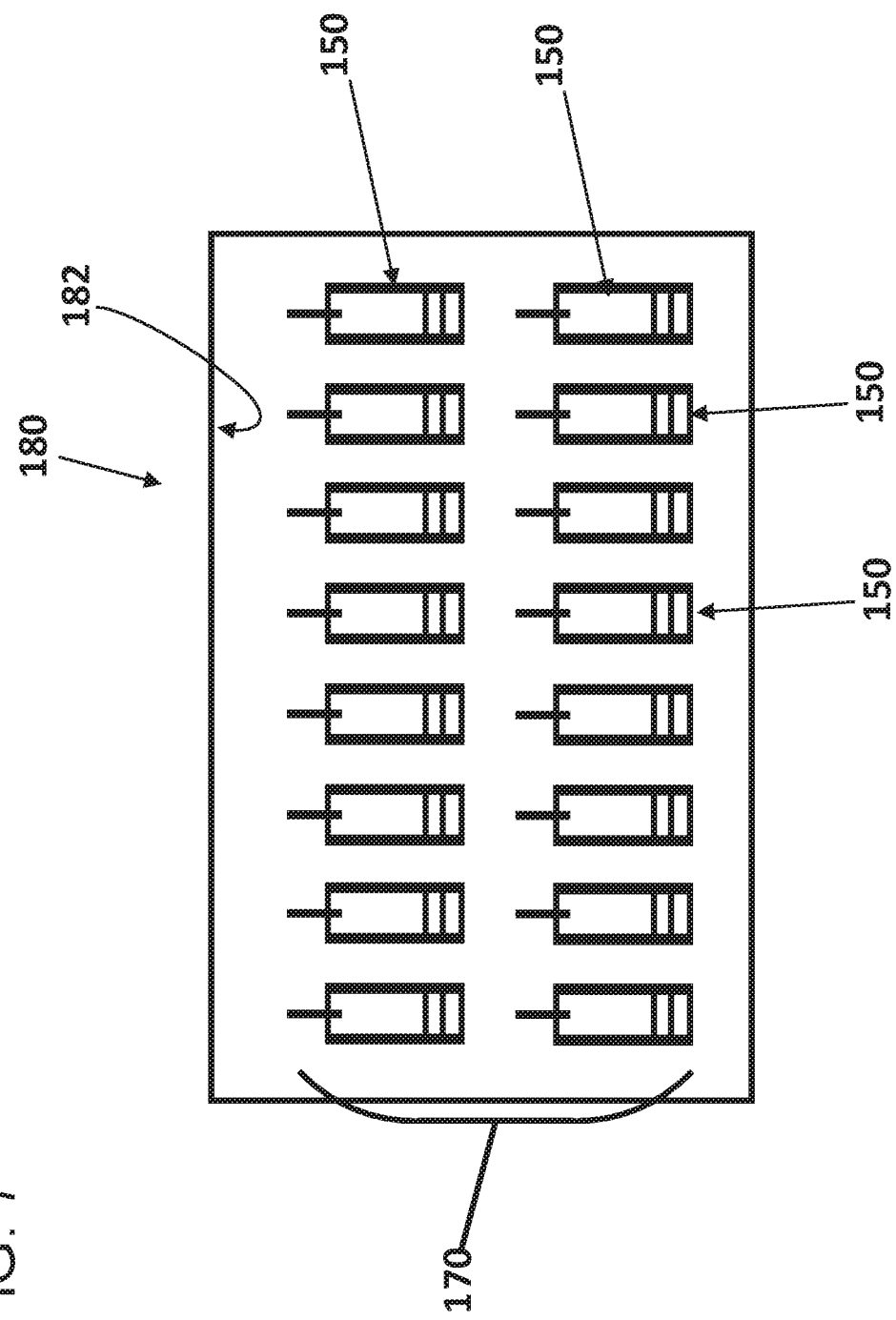
FIG. 7 is a schematic diagram of an example oven used in artificially aging one or more prefilled syringes.

At the age operation 202, one or more prefilled syringes 150, such as the prefilled syringes 150 shown in FIG. 1, can be aged to at least a simulated age that is at least equal to the desired shelf life for the therapeutic fluid 160 and the prefilled syringe 150. As shown in FIG. 7, in certain implementations, the prefilled syringes 150 or therapeutic fluid 160 are artificially aged using a heat source. For example, one or more syringes 150 prefilled with a therapeutic fluid 160 can be disposed within an interior 182 of an oven 180. In some implementations, humidity is not controlled during the artificial aging process. In other implementations, humidity is controlled during the artificial aging process.

To accelerate aging for the prefilled syringe 150, one or more prefilled syringes 150 are in an oven 180 at a predetermined temperature. The greater the temperature the faster the prefilled syringes 150 age to a simulated age. In some embodiments, the prefilled syringes 150 are heated at a temperature in the range from about 20° C. to about 60° C. For example, the prefilled syringes 150 can be heated at temperatures of about 5° C., about 25° C., or about 40° C. Each of the sample sets 170 is kept at the predetermined temperature for a different period of time (e.g., minutes, days, weeks, months, years). The temperature and length of time for heating the prefilled syringes 150 can be determined according to the Arrhenius calculation of Equation (1). The number of prefilled syringes 150 that are heated to accelerate aging depends on the number of samples to be tested for selection of an injection spring 109. The more samples that are tested, the more data will be available to select a spring 109. Additionally, sets of prefilled syringes 150 can be heated at different temperatures or tested for different lengths of time. Heating different sets of prefilled syringes 150 in this manner allows data simulating different shelf lives and different circumstances to be used in the spring 109 selection process.

At the test operation 204, one or more force tests can be performed on the aged prefilled syringes 150 using any suitable testing techniques including the testing techniques illustrated herein in more detail (see, e.g., FIGS. 4A, 4B, and 5). In general, the test or tests include measuring one or more exertion forces Fe applied to the stopper 157 of each prefilled syringe 150 as it moves from the first position, D1, to the second position, D2, and as therapeutic fluid 160 is dispensed. The exertion force measurements are associated with the corresponding position (i.e., displacement) of the stopper 157 along the path of travel P.

In some embodiments, the exertion force is measured for moving only the stopper 157 of the prefilled syringe 150 (see, e.g., FIGS. 4A and 5). In other examples, the exertion force is measured for moving the stopper 157 via the piston rod simultaneously operating other components of the auto injector that are powered by the injection spring (see, e.g., FIGS. 4B and 5).

At the select operation 206, the measured exertion forces are analyzed to determine an injection spring 109 that has enough energy to deliver a suitable amount of force and that also has suitable parameters for operating within the auto injector. The spring force is determined according to Hooke's law:

$$F_{spring}=K(l_0-x) \quad (4)$$

where $F_{spring}$ is the force of the spring, "K" is the spring constant for the particular injection spring, $l_0$ is the uncompressed spring length, and x is the current spring length.

In the following, the term compression of the spring or spring compression in a determined state is used to refer to the difference between the uncompressed length of the spring and the length of the spring in said determined state. In least some embodiment such as auto injector 140, there is a gap between the piston rod 107 and the stopper 157 at the start of operation. At the start of operation, the injection spring 109 must decompress slightly to engage the piston rod 107 against the stopper 157. In these embodiments, the spring length, at the start of operation—before actuation of the auto injector 140—is shorter than an initial spring length, $l_i$, when the piston rod 107 is against the stopper 157 and begins to push the stopper 157 from its first position, D1. In these embodiments, the dispensing force also can be modeled as:

$$F_d=K(C_i-x_{stopper}), \text{ wherein } C_i=l_o-l_i \quad (5)$$

where $C_i$ is the initial compression of the spring, $l_i$ is the length of the spring when the piston rod engages the stopper and the stopper is in the initial position, and $x_{stopper}$ is the displacement of the stopper with reference to the first initial position of the stopper. In addition, the stored energy available for dispensing the drug in the auto injector may be modeled as:

$$E=\tfrac{1}{2}KC_i^2 \quad (6)$$

Using these equations, a spring constant and uncompressed spring length for the injection spring 109 can be selected to provide a sufficient dispensing force to the stopper 157 to successfully move the stopper 157 along the path of travel, P for a displacement that is at least long enough to deliver a full dose of the therapeutic fluid 160 and within a desired time. It is noted that the initial spring length depends on the geometry of the auto injector 140 such as the spring length at the start of operation (i.e., the assembled spring length or cocked length) and the gap between the plunger rod 107 and the stopper 157 in the initial position.

Because equations (4) and (5) are linear, a spring force for the injection spring 109 can be represented in the graph shown in FIG. 3C by a line plotting a decreasing force over increasing displacement. In a possible embodiment, a measured exertion force may be used to determine the suitable spring 109. In this embodiment, the reference force, $F_{ref}$, used to calculate the spring force can be the maximum exertion force measured as the drive rod 314 of the test equipment 310 moves the stopper 157 from the first position, D1, to the second position, D2. For accelerated aged prefilled syringes 150 as disclosed herein, that maximum exertion force can be a glide force measured as the stopper 157 approaches the second position, D2, as illustrated in FIG. 3C. In other embodiments or circumstances, the maximum exertion force can be a glide force as the stopper 157 moves along an intermediate portion of the path of travel, P. In yet other embodiments or circumstances, the maximum exertion force can be the break-loose force as the stopper 157 begins movement from the first position, D1.

An additional condition that may be used for determining the spring parameters (e.g., spring constant, compressed length, uncompressed length) may be that the final spring force should be no less than 50% of the initial spring force, which is the spring force for the injection spring 109 when the piston rod 107 first engages the stopper 157 at the first position, D1. In other embodiments, the final spring force should be no less than 60%, 70%, 80%, or 90% of the initial spring force. These design specifications and parameters for the injection spring 109 may lead to several alternatives for a suitable spring 109. Other conditions such as market availability and price may then be considered when selecting an injection spring 109. In some embodiments, selecting a suitable spring 109 may involve maximizing a utility function including one or several of the conditions mentioned herein. In some embodiments, the injection spring 109 has a spring force when the stopper 157 is at the first position, D1, and is engaged by the piston rod 107 in the range from about 20 N to about 40 N. In some embodiments, the injection spring 109 has a spring force when the stopper 157 is at the first position, D1 and is engaged by the piston rod 107 in the range from about 20 N to about 30 N. Additionally, in some embodiments, the injection spring 109 can have a spring force when the stopper 157 is at the second position, D2, in the range from about 14 N to about 20 N. Additionally, in some embodiments, the injection spring 109 can have a spring force when the stopper 157 is at the second position, D2, in the range from about 15 N to about 18 N.

In some embodiments, several measured exertion forces may be used to determine the suitable spring 109. For example, an initial exertion force (break loose force) may be used to determine the suitable spring 109 together with exertion force(s) at the end of travel path, P. In another example, a reference energy for moving the stopper 157 in a prefilled syringe 150 may be calculated based on a measured force profile acquired by moving a stopper 157 using equipment as described in FIGS. 4-5. The reference energy may be calculated for a stopper 157 moving in one or more aged reference prefilled syringes 150 or one or more unaged prefilled syringes 150. In at least some embodiments, the selected spring 109 will have a stored energy when the stopper 157 is at the first position, D1 and engaged by the piston rod 107 that is about 25% or more than the reference stored energy. In other possible embodiments, the stored energy is about 20%, 30%, 40%, 50%, or 60% greater than the reference stored energy. Therefore, a possible design parameter for some embodiments is that injection spring 109 has about 25% more stored energy when the stopper 157 is at the first position, D1, and is engaged by the piston rod 107 than is actually required to move the stopper 157 in an unaged prefilled syringe 150 from the first position, D1, to the second position, D2, without stalling. In some embodiments, the stored energy in the injection spring 109 when the stopper 157 is in the first position, D1, and is engaged by the piston rod 107 is in the range from about 0.9 J to about 2 J.

Furthermore, it has been found that to ensure proper stopper 157 movement, it is beneficial that the dispensing force when the stopper 157 reaches the second position, D2, be as high as possible. Having this high dispensing force at the second position, D2, lowers the risk of stalling at the end of the dose delivery. Further, it has been found that it is beneficial that the initial dispensing force be as low as possible to avoid high initial impact. As a result, some possible embodiments have injection springs 109 that have a longer initial spring compression length over an injection spring 109 having a high spring constant. In some embodiments, the spring parameters may be selected to maximize the initial spring compression length of the injection spring 109 and minimize the spring constant. In other words, when several spring parameters would provide a suitable spring 109, the spring 109 having the lowest spring constant and the highest initial compression is preferred.

In some embodiments, the initial spring compression length is in the range from about 50 mm to about 100 mm with a spring constant in the range from about 0.2 N/mm to about 0.4 N/mm. In alternative embodiments, the initial spring compression length is in the range from about 75 mm to about 95 mm with a spring constant in the range from about 0.28 N/mm to about 0.32 N/mm. In another example, the spring constant is about 0.3 N/mm.

Once the spring parameters are determined, an injection spring 109 is selected that will cause the piston rod 107 of the auto injector 140 to exert a dispensing force against the syringe stopper 157 that is greater than the maximum measured exertion force so that the injection spring 109 will overcome all resistive forces acting against movement of the stopper 157 and have enough force to move the stopper 157 to the second position, D2, within a determined time.

Additionally, in some embodiments, parameters for the injection spring 109 are selected based on a maximum exertion force measured during testing of prefilled syringes 150 exposed to accelerated aging. In other examples, the parameters for the injection spring 109 are selected based on multiple exertion forces measured during the testing. For example, spring constants, uncompressed spring lengths, and compressed spring lengths can be calculated based on or for the multiple exertion forces, which can provide a more favorable slope of the spring force as the spring 109 decompresses.

Additionally, the embodiment shown herein used a helical spring for the injection spring 109. A helical spring is a linear rate spring. Other embodiments can use other types of springs 109 such as conical springs, constant force springs, variable force springs, torsion springs, gas springs, or hydraulic springs. Hooke's law for springs such as gas and hydraulic springs is not linear. However, it is substantially linear over the first part of the gas or hydraulic spring's displacement and the spring forces can still be approximated using equation (4) or a similar linear relationship. In alternative embodiments, suitable mathematical relationships and models other than Hooke's law can be used to determine forces for springs including linear and non-linear springs.

Figures 8, 9:
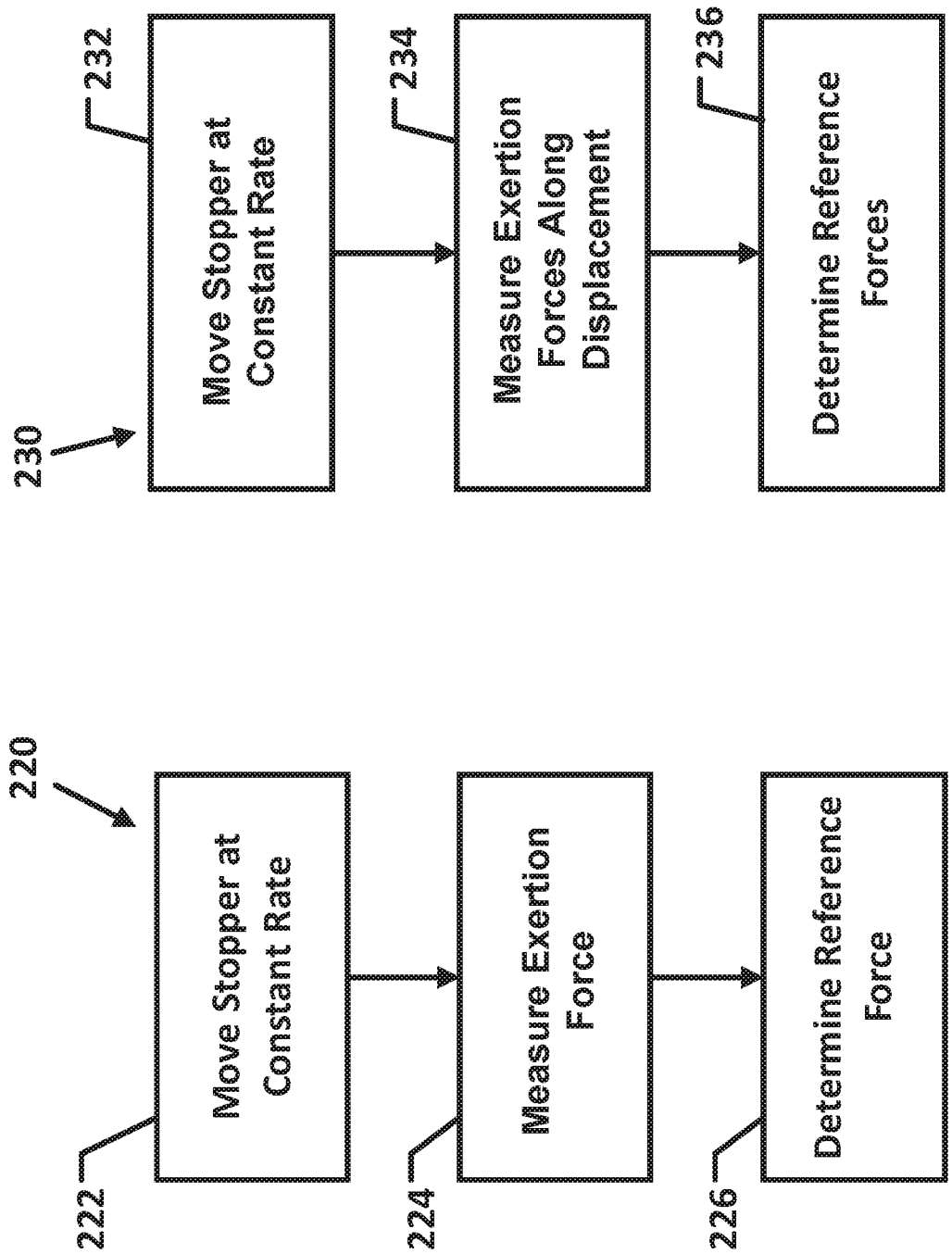
FIGS. 8-10 illustrate various testing processes that are each suitable for implementing the test operation of the determination process of FIG. 6.
Figures 10, 11:
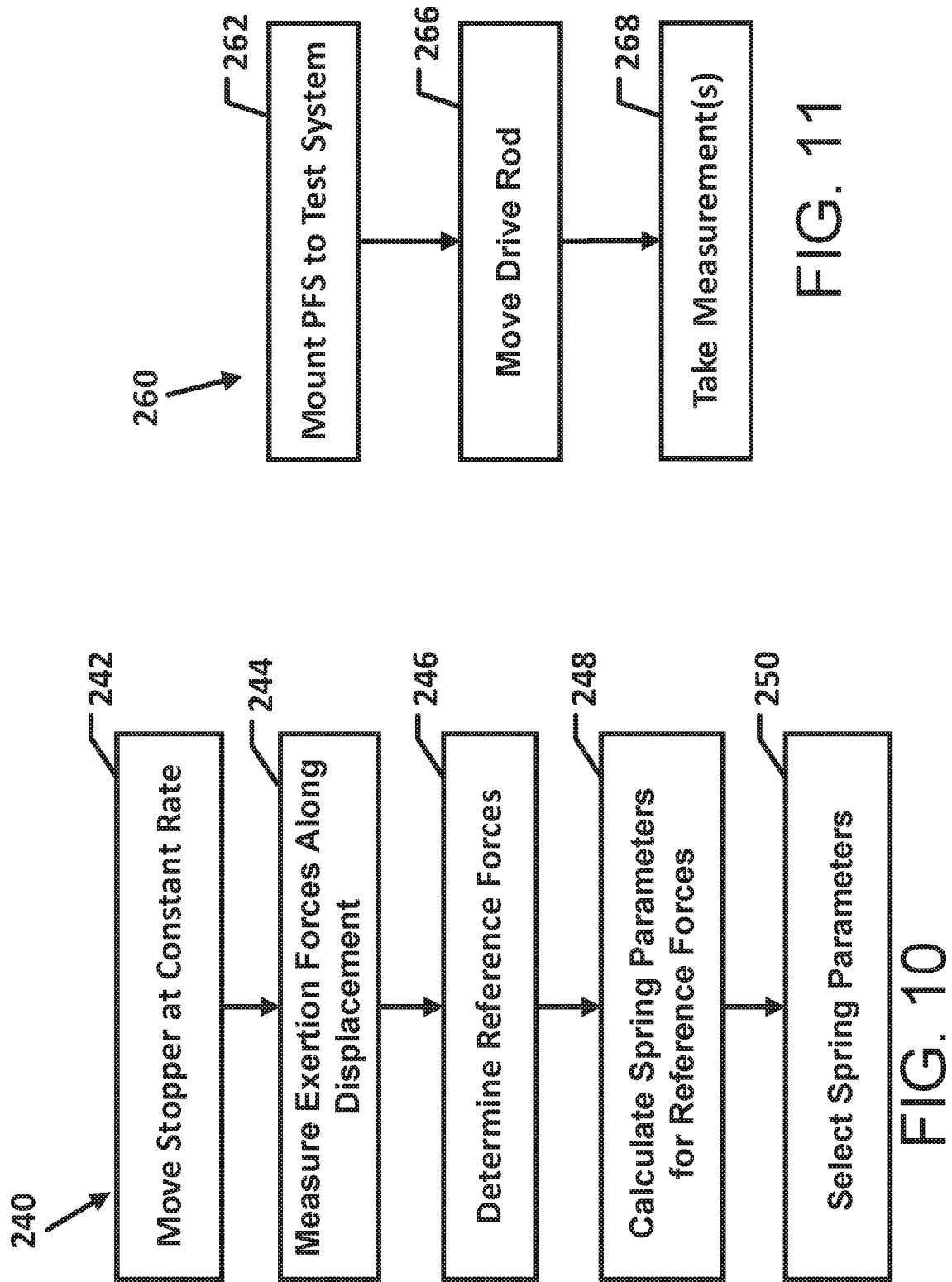
FIG. 11 is a flowchart illustrating a method for performing at least the move operations and the measure operations of the testing processes of FIGS. 8-10 using the testing equipment of FIG. 5.

FIGS. 8-10 illustrate various testing processes 220, 230, 240 that are each suitable for implementing the test operation 204 of the determination process 200. In certain implementations, the testing processes 220, 230, 240 are implemented using automated or semi-automated testing equipment, such as the testing equipment 310 described herein with relation to FIGS. 4A, 4B, and 5. Suitable processes for using the testing equipment 310 will be described in more detail herein with reference to FIG. 11.

Each of the testing processes 220, 230, 240 can be performed on a prefilled syringe 150, either alone or in combination with an auto injector 140 or components thereof. In some examples, the testing equipment 310 directly acts on the stopper 157 of a prefilled syringe 150. In other examples, the testing equipment 310 acts on a drive member 314 (e.g., piston rod 107) of the auto injector 140, which is operationally coupled to the syringe stopper 157.

The prefilled syringe 150 may be naturally aged or artificially aged. Each of the testing processes 220, 230, 240 also can be performed on unaged prefilled syringes 150. In some examples, the testing processes 220, 230, 240 are performed on prefilled syringes 150 prefilled with a therapeutic fluid 160. In other examples, the testing processes 220, 230, 240 are performed on syringes 150 prefilled with other types of fluid (e.g., saline or water).

FIG. 8 is a flowchart illustrating a first testing process 220 suitable for implementing the test operation 204 of the determination process 200. The first testing process 220 includes a move operation 222, a measure operation 224, and a determine operation 226.

At the move operation 222, the stopper 157 of a prefilled syringe 150 is moved distally within the syringe barrel 151 along the path of travel, P, at a constant speed. For example, the stopper 157 may be moved along the path of travel, P, from a first position (e.g., a proximal position, an initial position) D1 to a second position (e.g., a distal position, a bottomed-out position) D2.

In certain implementations, the constant speed is selected to match a displacement speed of the stopper 157 during an actual injection using the auto injector 140 in which the stopper 157 is moved from a first position, D1, to a second position, D2, and a full dose of fluid 160 is held in the syringe barrel 151 between the first and second positions D1, D2. For example, the constant speed may be selected to simulate a desired injection time in the range from about 5 seconds to about 19 seconds. Another embodiment may select a constant speed to simulate an injection time in the range from about 5 seconds to about 12 seconds. Another embodiment may select a constant speed to simulate an injection time in the range from about 6 seconds to about 20 seconds. Another embodiment may select a constant speed to simulate an injection time in the range from about 8 seconds to about 15 seconds. Another embodiment may select a constant speed to simulate an injection time in the range from about 15 seconds to about 25 seconds. In certain examples, the constant speed may be selected to simulate an injection time in the range from about 17 seconds to about 22 seconds. In an example, the constant speed may be selected to simulate an injection time of about 12 seconds. In an example, the constant speed may be selected to simulate an injection time of about 8 seconds. In an example, the constant speed may be selected to simulate an injection time of about 18 seconds. In an example, the constant speed may be selected to simulate an injection time of about 19 seconds. In an example, the constant speed may be selected to simulate an injection time of about 20 seconds. In certain examples, the constant speed is selected to be in the range from about 60 mm/min to about 360 mm/min. In other embodiments, the constant speed is selected to be between about 150 mm/min and about 200 mm/min. In certain examples, the constant speed may be selected to be between about 80 mm/min and about 90 mm/min. In an example, the constant speed is selected to be about 150 mm/min. In an example, the constant speed is selected to be about 86 mm/min. In an example, the constant speed is selected to be about 175 mm/min.

The measure operation 224 measures one or more exertion forces applied to the stopper 157 to move the stopper 157 distally along the path of travel, P, at the constant speed. In certain embodiments, the exertion force utilized to initiate movement of the stopper 157 relative to the syringe barrel 151 (i.e., the break-loose force) is measured. In other embodiments, the exertion force utilized to maintain movement of the stopper 157 along the path of travel, P, within the syringe barrel 151 (i.e., the glide force) is measured. For example, a maximum exertion force applied during movement of the stopper 157 along the path of travel, P, (i.e., a maximum glide force) may be measured. In certain examples, the displacement of the stopper 157 is measured at the same time as the exertion force is measured.

At the determine operation 226, a reference force for use in calculating a suitable spring 109 is determined. In certain embodiments of the select operation 206, the reference force is used to select a spring constant, uncompressed spring length, or compressed spring length.

In some implementations, the reference force is the maximum or peak force the injection spring 109 needs to overcome to move the stopper 157 along the path of travel, P, between the first and second positions D1, D2. Accordingly, the reference force is no less than the measured exertion force being applied to the stopper 157 to overcome any resistive forces that oppose the distal movement of the stopper 157 along the path of travel, P. In certain embodiments, the reference force is equal to the maximum measured exertion force and can be used to determine parameters for the injection spring 109. In other embodiments, the reference force can be greater than the maximum measured exertion force. In yet other embodiments, the reference force can be lower than the maximum measured exertion force. For example, the maximum measured exertion force could be measured at a displacement outside the range of the first and second positions D1, D2 for the stopper 157.

In other implementations, the reference force is also determined based on resistance forces generated by components of the auto injector 140. For example, the reference force also may account for one or more friction forces generated by movement between two or more components (e.g., the piston rod 107, the support member 105, the indicator sleeve 111, and the holding sleeve 108 shown in FIGS. 13-17) of the auto injector 140. In an example, the reference force also may include the force needed to move or operate one or more components (e.g., the holding pin 106, the holding sleeve 108) of the auto injector 140 against the bias of another spring 109 (e.g., cover sleeve spring 110 of FIGS. 13-17). The resistive forces generated by the auto injector 140 may be separately measured, calculated or otherwise estimated.

FIG. 9 is a flowchart illustrating a second possible testing process 230 suitable for implementing the test operation 204 of the determination process 200. The second testing process 230 includes a move operation 232, a measure operation 234, and a determine operation 236. The move operation 232 of the second testing process 230 is the same or substantially the same as the move operation 222 of the first testing process 220.

The measure operation 234 is substantially the same as the measure operation 224 of the first testing process 220, except that multiple exertion force measurements are taken along the path of travel, P. Each exertion force measurement is associated with the corresponding displacement of the stopper 157 along the path of travel, P. In some implementations, two exertion force measurements are taken along the path of travel, P, (e.g., at the first position D1 and the second position D2). In other implementations, three or more exertion force measurements are taken along the path of travel, P. In certain examples, the exertion force is measured at constant intervals along the path of travel, P. In certain examples, the exertion force is continuously measured along the path of travel, P.

In certain embodiments, the displacement of the drive rod 314, which corresponds to displacement of the plunger 157 also is measured. The displacement can be measured at the same time as each measurement is made of the exertion forces. In certain embodiments, the displacement and exertion force measurements can be correlated to form a force profile.

The determine operation 236 is the same or substantially the same as the determine operation 226 of the first testing process 220, except that two or more reference forces are determined. For example, one determined reference force can correspond to the break-loose force, and another determined reference force can correspond to the maximum measured glide force. In other embodiments, two or more determined reference forces can correspond to different measured glide forces. In other embodiments, one determined reference force can correspond to a glide or break-loose force, and another determined reference can correspond to a displacement of the piston rod 107 for the auto injector 140 that is outside the range of displacement for the stopper 157. For example, a determined reference force can correspond to the force needed to begin movement of the piston rod 107 before it engages the stopper 157.

In some embodiments, at least one reference force is determined based on an exertion force measured for pushing the stopper 157 from the first to the second positions D1, D2 in the syringe barrel 151, and at least another reference force is determined based on the measured force or friction related to moving or operating internal components of the auto injector 140. And in yet another possible embodiment, at least one reference force is determined that corresponds to the exertion force measured for operating internal components of the auto injector 140 and pushing the stopper 157.

FIG. 10 is a flowchart illustrating a third testing process 240 suitable for implementing the test operation 204 of the determination process 200. The third testing process 240 determines spring parameters such that an injection spring 109 having the determined spring parameters can successfully drive the stopper 157 along the path of travel, P. The third testing process 240 includes a move operation 242, a measure operation 244, a determine operation 246, a calculate operation 248, and a select operation 250.

The move operation 242 of the third testing process 240 is the same or substantially the same as the move operation 222 of the first testing process 220.

In some implementations, the measure operation 244 is the same or substantially the same as the measure operation 224 of the first testing process 220. In other implementations, the measure operation 244 is the same or substantially the same as the measure operation 234 of the second testing process 230.

In some implementations, the determine operation 246 is the same or substantially the same as the determine operation 226 of the first testing process 220. In other implementations, the determine operation 246 is the same or substantially the same as the determine operation 236 of the second testing process 230.

The calculate operation 248 determines a corresponding spring constant, uncompressed spring length, or compressed spring length for each of the one or more reference forces determined in the determine operation 246. These spring parameters are calculated based on the determined reference force (which equals or otherwise corresponds to a measured exertion force) and the corresponding displacement of the stopper 157. The calculated spring parameters are "reference spring parameters."

In some embodiments, assuming an uncompressed spring length and an auto injector geometry, the calculate operation 248 determines a minimum spring constant needed to generate an exertion force at a corresponding displacement position of the stopper 157 sufficient to drive the stopper 157 along the path of travel, P. In other embodiments, the calculate operation 248 determines a minimum spring constant needed to generate the required exertion force and to overcome resistance forces generated by the auto injector 140. In some embodiments, the uncompressed spring length also is determined by the calculate operation 248. In some embodiments, the calculate operation 248 determines the minimum spring constant and the maximum uncompressed spring length. In other embodiments, the calculate operation 248 may determine the maximum spring constant.

The second determine operation 250 compares the reference spring parameters determined in the calculate operation 248 to determine optimal spring parameters. The optimal spring parameters can be chosen based on a variety of different criteria such as desired injection time, desired spring forces, spring cost, and geometry of the auto injector 140.

FIG. 11 is a flowchart 260 illustrating a method for performing at least the move operations 222, 232, 242 and the measure operations 224, 234, 244 of the testing processes 220, 230, 240 using the testing equipment 310 of FIGS. 4A, 4B, and 5. In certain implementations, the testing equipment 310 includes a tensometer or other mechanism for measuring an exertion force on the syringe stopper 157.

As described above, the testing equipment 310 may include a frame 316 to hold the prefilled syringe 150.

In some examples, the operations of flowchart 260, and the other flowcharts and operations discussed herein, are performed on a single prefilled syringe 150. In other examples, however, the operations of the flowchart 260 are performed on multiple prefilled syringes 150. In certain examples, the operations can be performed on prefilled syringes 150 of various ages (e.g., natural ages or artificial ages). In certain examples, the operations can be performed on unaged prefilled syringes 150. In some examples, the operations of the flowchart 260 are implemented using a prefilled syringe 150 by itself. In other examples, the operations can be implemented using a prefilled syringe 150 in combination with one or more parts of an auto injector 140.

In certain examples, portions of the auto injector 140 (e.g., portions of the drive assembly) also can be mounted to the testing equipment 310 as shown in FIG. 4B. In such examples, the frame 316 can be adapted to hold the auto injector 140 components. For example, an additional clamp 317 can be mounted to the frame 316 to hold a drive member 314 (e.g., piston rod 107) of the auto injector 140, the entire auto injector 140, or a portion thereof. In such examples, the drive rod 314 of the testing equipment 310 is operably coupled to the stopper 157 via the drive member 314 of the auto injector 140.

At the actuate operation 266, the testing equipment 310 generates an exertion force on the syringe stopper 157. In certain examples, the actuate operation 266 includes advancing (e.g., lowering) the drive rod 314 of the testing equipment 310 towards the stopper 157. In some examples, the drive rod 314 is moved automatically. In other examples, the drive rod 314 is moved manually. In certain examples, the drive rod 314 is moved at a constant speed.

In an example, the drive rod 314 is attached to a 25 N load cell. In other embodiments, the drive rod 314 is attached to a 200 N load cell. Other load cells are possible that have a sufficient range of sensitivity to measure the forces that can be applied to the drive rod 314.

The measure operation 268 takes one or more measurements of the exertion force being applied by the drive rod 314 to the stopper 157 as the stopper 157 moves along the path of travel, P. For example, the testing equipment 310 may automatically take measurements of the exertion force applied by the drive rod 314. The testing equipment 310 also tracks the displacement of the drive rod 314, which directly relates to the displacement of the syringe stopper 157. Accordingly, the measure operation 268 results in one or more exertion force readings that are each correlated with a determined displacement of the stopper 157.

In an example, an exertion force measurement may be taken when the stopper 157 initially moves relative to the syringe barrel 151. In another example, an exertion force measurement may be taken when the stopper 157 approaches or arrives at an end of the path of travel, P. In another example, multiple exertion force measurements may be taken at periodic intervals or distances along the path of travel, P. In another example, exertion force measurements are continuously taken along the path of travel, P.

Figure 12:
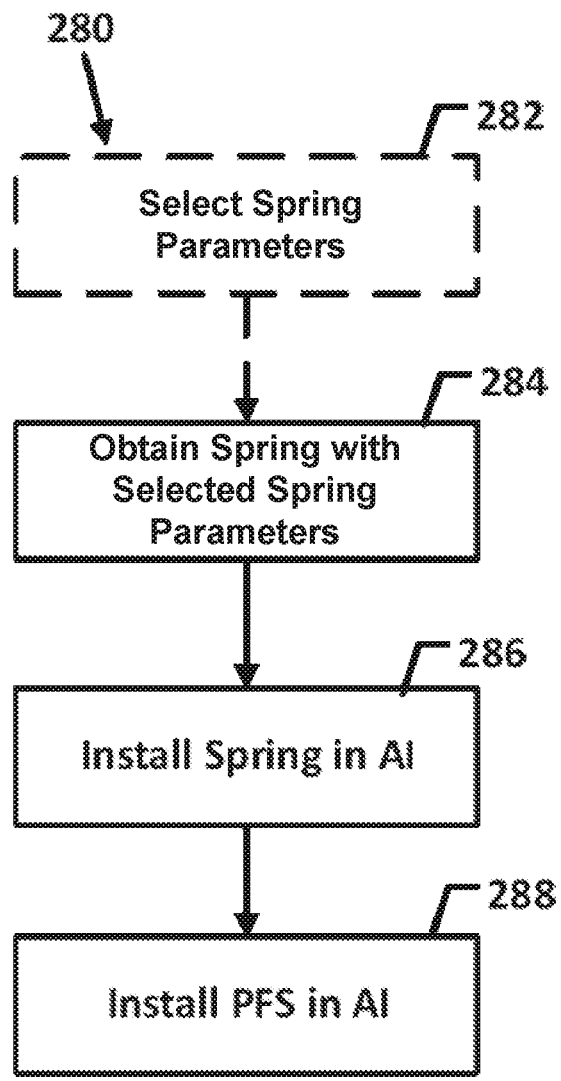
FIG. 12 is a flowchart illustrating an assembly process for assembling an auto injector.

FIG. 12 is a flowchart illustrating an assembly process 280 for assembling an auto injector, such as an auto injector 140 of FIGS. 13-17, with a prefilled syringe, such as prefilled syringe 150 of FIG. 1, and the selected injection spring 109. The assembly process 280 includes at least an obtain operation 284, a first install operation 286, and a second install operation 288. The assembly process 280 may optionally include a select operation 282.

At the select operation 282, the user 190 selects a spring constant for an injection spring 109 to be installed in the auto injector 140 to drive injection of the prefilled syringe 150. The spring constant is selected to be sufficient to drive injection of the prefilled syringe 150 even if the prefilled syringe 150 has artificially aged. The user 190 can select the spring constant using any of the determination processes 200 or testing processes 220, 230, 240 described herein.

At the obtain operation 284, the user 190 selects an injection spring 109 having the selected spring parameters. The selected injection spring 109 produces a biasing force at least sufficient to drive the syringe stopper 157 within the syringe barrel 151 fully along the path of travel, P. In certain examples, the selected injection spring 109 produces a biasing force sufficient to drive the stopper 157 fully along the path of travel, P, and to perform other operations within the auto injector 140. For example, the selected injection spring 109 is sufficiently strong to bias the holding pin 106 and holding sleeve 108 to a proximal position, to charge the cover sleeve spring 110, and to drive the stopper 157 along the path of travel, P.

In some implementations, the selected injection spring 109 is a compression spring. In some examples, the selected injection spring 109 is a linear rate spring. In other examples, the selected injection spring 109 is a variable rate spring. In still other examples, the selected injection spring 109 is a constant force spring. In other implementations, the selected injection spring 109 is a mechanical gas spring, a pneumatic spring, or a hydraulic spring.

At the first install operation 286, the selected injection spring 109 is installed in the auto injector 140. For example, the selected injection spring 109 can be disposed within the outer body 102 of the auto injector 140 as part of the drive assembly. In certain examples, the selected injection spring 109 is aligned with the piston rod 107 (e.g., see FIG. 14). In an example, the selected injection spring 109 is compressed between the piston rod 107 and the holding pin 106 (e.g., see FIG. 14).

At the second install operation 288, the prefilled syringe 150 is installed in the auto injector 140. For example, a prefilled syringe 150 can be mounted at the syringe holder 101 within the outer body 102.

Figure 13:
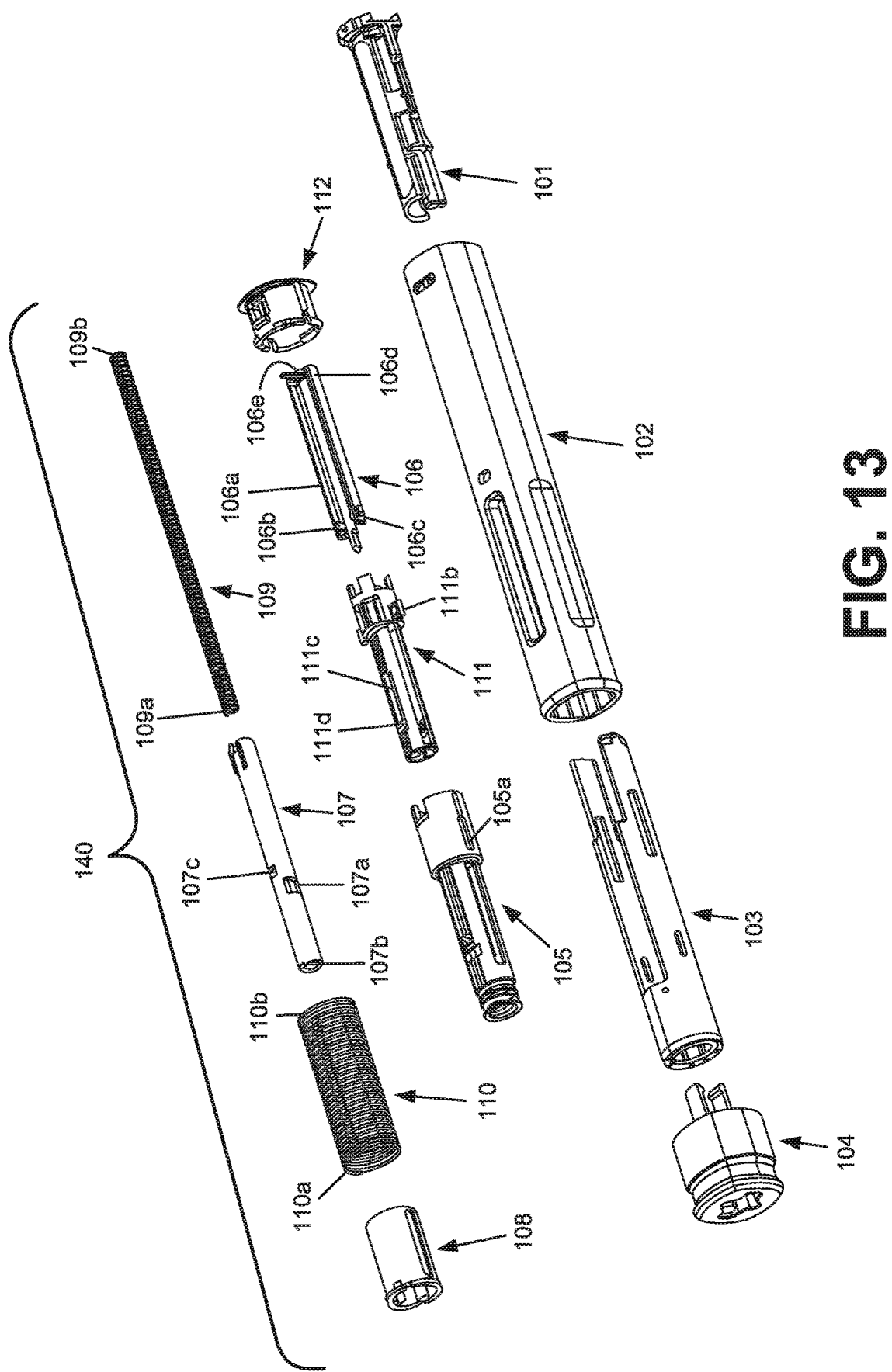
FIG. 13 illustrates the components of the auto injector exploded from each other for ease in viewing.
Figure 14:
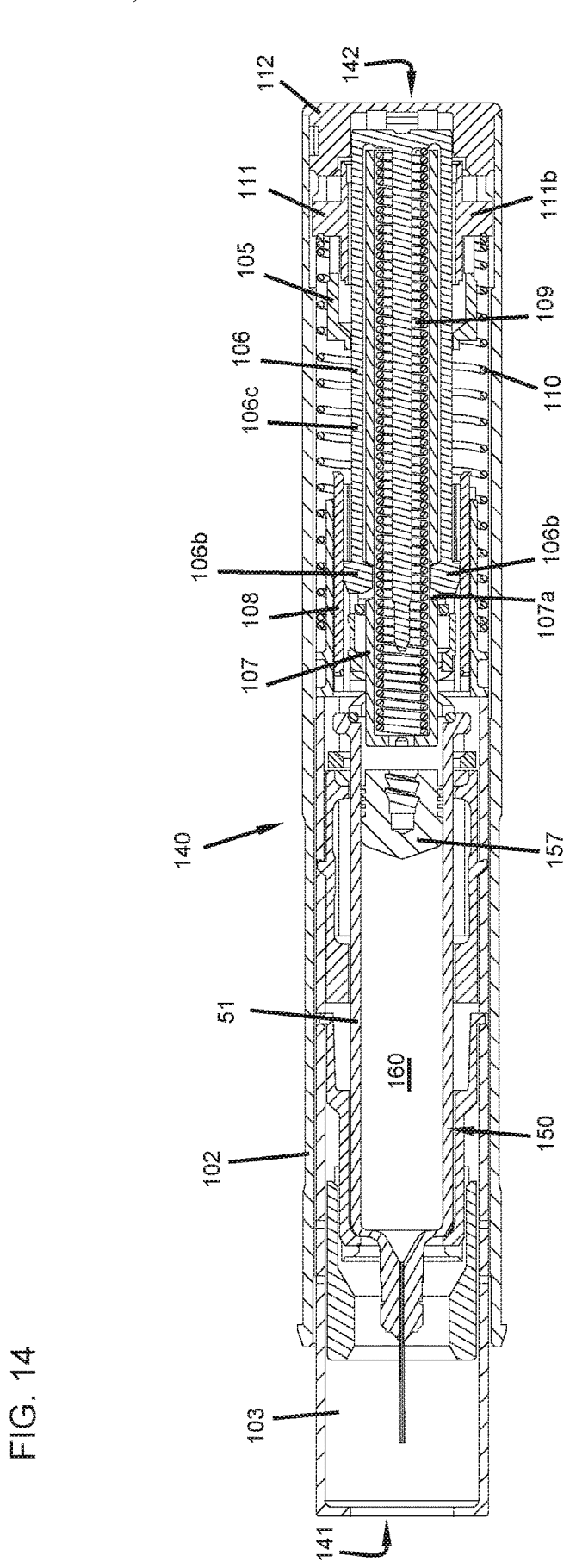
FIG. 14 is a cross-section of the auto injector of FIG. 13, the auto injector being disposed in a pre-injection configuration.
Figure 15:
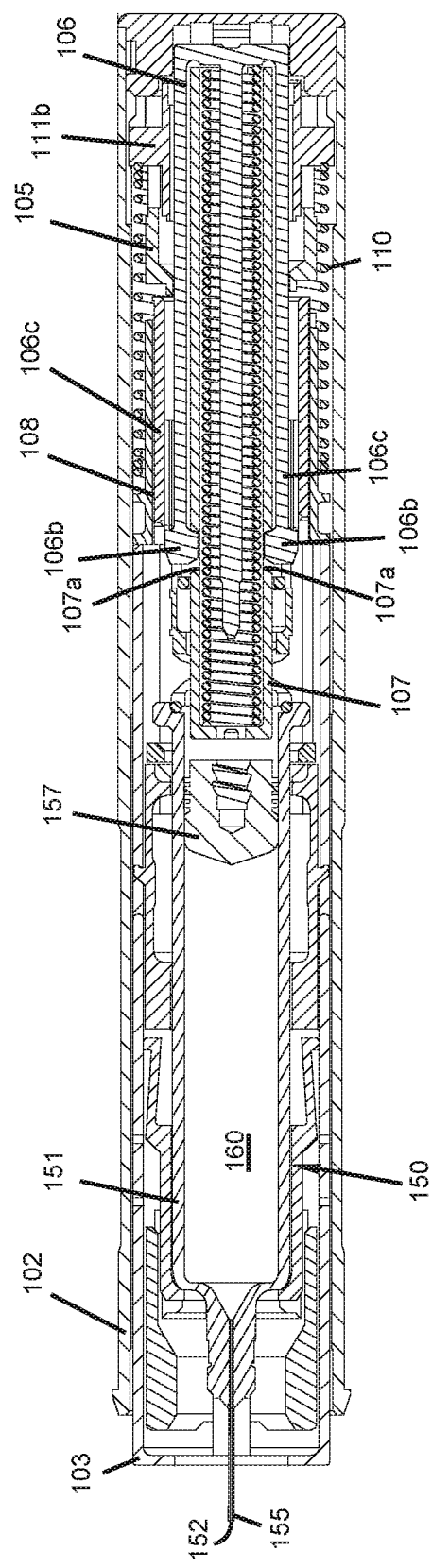
FIG. 15 shows the auto injector of FIG. 14 in a mid-injection configuration.
Figure 16:
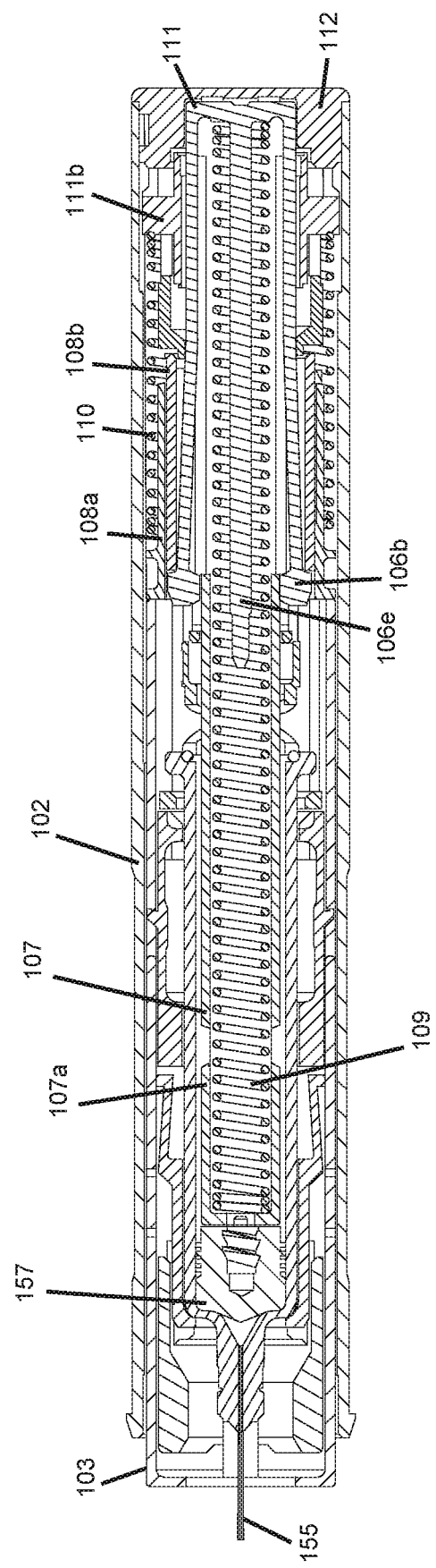
FIG. 16 shows the auto injector of FIG. 14 in an end of injection configuration.
Figure 17:
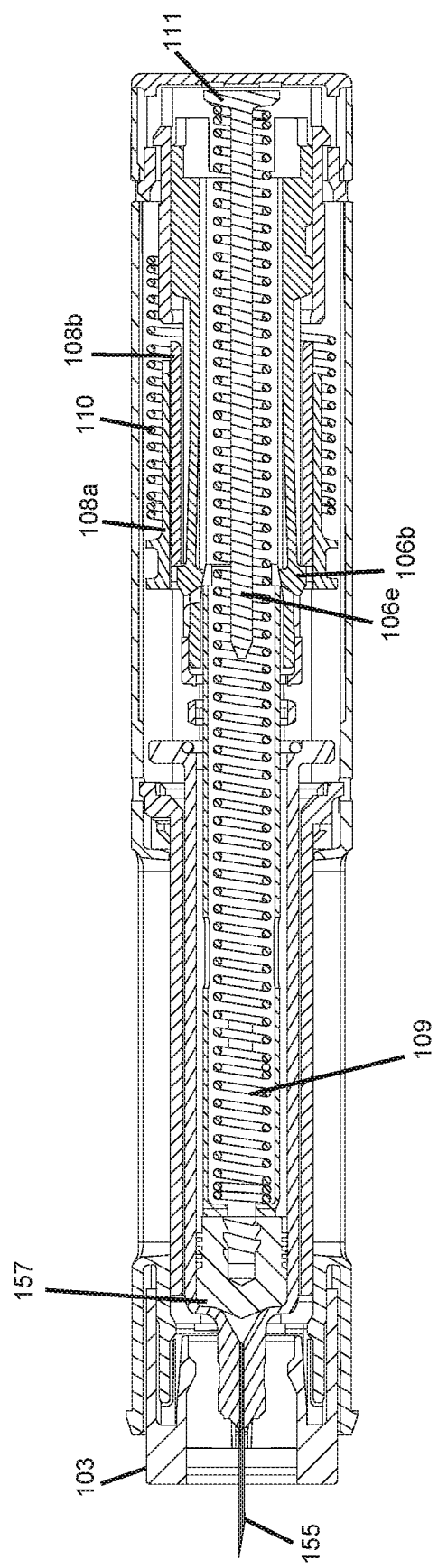
FIG. 17 shows the auto injector of FIG. 16 rotated 90°.

FIGS. 13-17 illustrate an example auto injector 140 suitable for injecting the prefilled syringe 150 of FIG. 1. FIG. 13 illustrates the components of the auto injector 140 exploded from each other for ease in viewing. FIG. 14 is a cross-section of the auto injector 140 of FIG. 13, the auto injector 140 being disposed in a pre-injection configuration. FIG. 15 shows the auto injector 140 of FIG. 14 in a mid-injection configuration. FIG. 16 shows the auto injector 140 of FIG. 14 in an end of injection configuration. FIG. 17 shows the auto injector 140 of FIG. 16 rotated 90°. Although an example embodiment of an auto injector 140 is disclosed and illustrated herein, any suitable spring-driven auto injector can be used with the apparatuses and methods disclosed herein.

The auto injector 140 has a distal end 141 and a proximal end 142 (see FIG. 14). The auto injector 140 is actuated by pushing the distal end 141 against the body of a patient 180 at an injection site 198. The auto injector 140 is held at the injection site 198 until a dosage of therapeutic fluid 160 has been expelled from the prefilled syringe 150.

The auto injector 140 includes an outer housing 102 and an end cap 112 mounted at the proximal end 142 of the outer housing 102. The auto injector 140 also includes a syringe holder 101 disposed within the outer housing 102. The syringe holder 101 and the end cap 112 are stationary with respect to the housing 102. The syringe holder 101 is configured to hold a prefilled syringe, such as the prefilled syringe 150 of FIG. 1.

A cover sleeve 103 is mounted at the distal end 141 of the outer housing 102. The cover sleeve 103 is telescopically slidable relative to the outer housing 102 between an extended position (FIG. 14) and a retracted position (FIG. 15). When in the extended position, the cover sleeve 103 surrounds the syringe needle 155 of the prefilled syringe 150. Moving the cover sleeve 103 to the retracted position exposes the syringe needle 155.

A cover sleeve spring 110 extends between a first end 110a and a second end 110b. The cover sleeve spring 110 extends over a first length between the first and second ends 110a, 110b when the cover sleeve 103 is extended. The cover sleeve spring 110 is compressed to a second length between the first and second ends 110a, 110b when the cover sleeve 103 is retracted. The second length is shorter than the first length. The cover sleeve spring 110 biases the cover sleeve 103 to the extended position. The cover sleeve 103 can be moved to the retracted position against the bias of the spring 110, thereby compressing the spring 110. In the example shown, the spring 110 is a helical coil spring. In other examples, however, the spring 110 can be a gas-powered spring, a pneumatic spring, a hydraulic spring, or any other type of spring.

A needle cap remover 104 is initially disposed over the cover sleeve 103 and engages the outer housing 102. The needle cap remover 104 inhibits movement of the cover sleeve 103 to the retracted position while the needle cap remover 104 engages the cover sleeve 103 and outer housing 102. The needle cap remover 104 grips a rigid needle shield that is initially disposed about the needle 155 of the prefilled syringe 150. When removed from the auto injector 140, the needle cap remover 104 entrains the rigid needle shield, thereby removing the rigid needle shield from the syringe needle 155.

A support member 105 is disposed within the outer housing 102 proximal of the syringe holder 101. The support member 105 is axially and rotationally fixed to the end cap 112. The distal end of the support member 105 abuts against a proximal end of the syringe holder 101.

A drive assembly is disposed within the outer housing 102 proximal of the syringe holder 101. The drive assembly includes an injection spring 109 and a subassembly biased by the injection spring 109. In the example shown, the injection spring 109 is a helical coil spring having a variable force. In other examples, however, the injection spring 109 can be a conical spring, a torsion spring, a gas-powered spring, a pneumatic spring, a hydraulic spring, or any other type of variable force or constant force spring. The injection spring 109 also can be any other injection spring 109 or structure that biases the piston rod 107 toward the distal end 141 of the auto injector 140.

The drive or subassembly includes at least a piston rod 107 aligned with the stopper 157 of the prefilled syringe 150. The piston rod 107 is axially movable within the outer body 102 along a travel distance between a cocked position and a bottomed-out position. When in the cocked position, the piston rod 107 is proximally spaced from the prefilled syringe stopper 157. When in the bottomed-out position, the piston rod 107 presses the stopper 157 against the proximally facing shoulder 151a within the interior 154 of the prefilled syringe 150.

Because the piston rod 107 is spaced from the stopper 157 when in the cocked position, the injection spring 109 will not apply a dispensing force against the stopper 157 immediately upon release and expansion of the spring 109. The injection spring 109 will decompress slightly and advance the piston rod 107 a short distance until the piston rod 107 engages the stopper 157. Once the piston rod 107 engages the stopper 157, the injection spring 109 will continue to decompress, but resistive forces from the prefilled syringe 150 such as resistance and hydrodynamic force will act against movement of the stopper 157 and hence against decompression of the injection spring 109.

The injection spring 109 extends between a first end 109a and a second end 109b. The injection spring 109 is compressed to a first cocked length between the first and second ends 109a, 109b when the piston rod 107 is disposed in the cocked position (see FIG. 14). The injection spring 109 is extended to a second length between the first and second ends 109a, 109b when the piston rod 107 is disposed in the bottomed-out position (see FIG. 16). The second length is longer than the first length.

The injection spring 109 applies an exertion force to bias the piston rod 107 distally towards the bottomed-out position. In an example, the injection spring 109 is disposed within a hollow interior of the piston rod 107. For example, the first end 109a of the injection spring 109 may push against an inner shoulder of the piston rod 107 to bias the piston rod 107 distally. The first length may be about 72 mm and the second length may be of about 106 mm. The injection spring 109 may have an uncompressed length of about 157 mm. A constant of the injection spring 109 may be of about 0.30 N/mm.

In certain examples, the subassembly also includes a holding pin 106. The injection spring 109 biases the holding pin 106 proximally towards the end cap 112. For example, the second end 109b of the injection spring 109 may push against an inner shoulder of the holding pin 106. In certain examples, the injection spring 109 is sandwiched between the piston rod 107 and the holding pin 106. In an example, the injection spring 109 biases the holding pin 106 proximally while biasing the piston rod 107 distally.

The holding pin 106 has a locking configuration and a releasing configuration. When in the locking configuration, the holding pin 106 engages the piston rod 107 to hold the piston rod 107 in an axially fixed position relative to the holding pin 106 against the bias of the injection spring 109. In certain examples, the holding pin 106 holds the piston rod 107 in the cocked position against the bias of the injection spring 109. When in the releasing configuration, the holding pin 106 releases the piston rod 107 to enable relative movement between the piston rod 107 and the holding pin 106.

In particular, the holding pin 106 of the drive assembly includes arms 106a extending from fixed ends 106d to free ends 106c. The fixed ends 106d are attached to a base portion 106e. The free ends 106c define stop members 106b, which move radially when the arms 106a are flexed. In certain examples, the base portion 106e is sized to extend into the piston rod 107. In certain examples, the base portion 106e is sized to extend through at least a portion of the injection spring 109 so that the injection spring 109 coils around the base portion 106e.

The piston rod 107 defines recesses 107a in which the stop members 106b of the holding pin 106 can seat. Accordingly, the holding pin 106 is disposed in the locking configuration when the arms 106a are flexed radially inwardly so that the stop members 106b engage the recesses 107a to retain the piston rod 107 in the cocked position. The holding pin 106 transitions to the releasing configuration when the arms 106a flex radially outwardly to move the stop members 106b away from the recesses 107a.

A holding sleeve 108 surrounds a portion of the holding pin 106. The holding sleeve 108 moves axially between a distal position and a proximal position. When in the distal position, the holding sleeve 108 retains the holding pin 106 in the locking configuration (see FIG. 14). In particular, the holding sleeve 108 radially aligns with the arms 106a and has a sufficiently small inner cross-dimension to inhibit outward radial flexing of the arms 106a. Accordingly, the holding sleeve 108 inhibits outward radial movement of the stop members 106b of the holding pin 106 from the recesses 107a of the piston rod 107. When in the proximal position, the holding sleeve 108 is axially offset from the stop members 106b, thereby allowing the holding pin 106 to transition to the releasing configuration.

Prior to injection, the holding sleeve 108 is biased to the distal position by the cover sleeve spring 110 extended to the second length. In certain examples, the cover sleeve spring 110 biases the cover sleeve 103 through the holding sleeve 108. For example, the first end 110a of the cover sleeve spring 110 abuts the holding sleeve 108, which abuts a proximal end of the cover sleeve 103. Movement of the cover sleeve 103 to the retracted position pushes the holding sleeve 108 to the proximal position and compresses the cover sleeve spring 110 to the second length.

In certain implementations, the holding sleeve 108 has a telescopic configuration. For example, the holding sleeve 108 may include an outer body 108a and an inner body 108b (see FIG. 16). The inner body 108b is disposed around the support member 105. The inner body 108b is rotationally fixed to, but axially movable relative to the support member 105. The outer body 108a is disposed around the inner body 108b. The first end 110a of the cover sleeve spring 103 abuts the outer body 108a to bias the holding sleeve 108 distally.

The outer body 108a and inner body 108b are rotationally fixed together. The outer body 108a and inner body 108b snap-fit to each other to move axially together as a unit from the distal position to the proximal position. For example, the inner body 108b has a ramped tooth and the outer body 108a defines a slot sized to receive the ramped tooth. The ramped tooth extends through the slot to be entrained by the outer body 108a in the proximal direction. The ramped tooth cams out of the slot as the outer body 108a is moved distal of the inner body 108b.

An indicator sleeve 111 is disposed within the outer housing 102 proximal of the syringe holder 101. As will be described in more detail herein, interaction between the indicator sleeve 111 and other components within the outer housing 102 generates noise (e.g., clicks) that audibly indicate stages of the injection (e.g., start of injection and end of injection).

The indicator sleeve 111 is axially movable relative to the outer housing 102 between a proximal position and a distal position. For example, the indicator sleeve 111 has wings 111b that slide in slots 105a defined in the support member 105 to limit axial movement between the indicator sleeve 111 and support member 105. The indicator sleeve 111 is biased to the proximal position by the cover sleeve spring 110. In an example, the second end 110b of the cover sleeve spring 110 abuts a portion of the indicator sleeve 111. Accordingly, the cover sleeve spring 110 is sandwiched between the holding sleeve 108 and the indicator sleeve 111. In an example, the cover sleeve spring 110 is sandwiched between the outer body 108a of the holding sleeve 108 and the wings 111b of the indicator sleeve 111.

The indicator sleeve 111 limits axial movement of the holding pin 106 relative to the outer body 102. For example, the indicator sleeve 111 defines grooves in which the stop members 106b of the holding pin 106 ride during axial movement of the holding pin 106 between the respective distal and proximal positions. Engagement between the stop members 106b and the grooves limits distal movement of the holding pin 106 relative to the indicator sleeve 111, which limits the distal movement of the holding pin 106 relative to the support member 105, which is axially fixed relative to the outer body 102.

The indicator sleeve 111 selectively engages the piston rod 107. For example, the indicator sleeve 111 may have one or more arms 111c with detents 111d at the free ends. The arms 111c flex to move the detents 111d radially relative to the piston rod 107. The detents 111d are sized to snap into corresponding slots 107c defined in the piston rod 107.

FIG. 14 illustrates the auto injector 140 in a pre-injection configuration. The needle cap remover 104 and rigid needle shield have been removed. The syringe stopper 157 is disposed at the first position, D1, along the path of travel, P, within the prefilled syringe 150. The piston rod 107 is held at a location spaced proximally from the syringe stopper 157 by the holding pin 106.

The holding pin 106 and piston rod 107 are positioned relative to each other such that the stop members 106b of the holding pin 106 radially align with the recesses 107a of the piston rod 107. The holding sleeve 108 is disposed in the distal position at which the holding sleeve 108 (e.g., the inner body 108b of the holding sleeve 108) radially aligns with the stop members 106b of the holding pin 106. Accordingly, the holding sleeve 108 presses the stop members 106b into the recesses 107a and inhibits radial movement of the stop members 106b out of the recesses 107a.

The indicator sleeve 111 also is disposed in the distal position. The detents 111d of the indicator sleeve 111 are disposed within the slots 107c of the piston rod 107. The holding sleeve 108 (e.g., the inner body 108b of the holding sleeve 108) radially aligns with the detents 111d. The inner cross-dimension of the inner body 108b of the holding sleeve 108 is sufficiently small to retain the detents 111d within the slots 107c when radially aligned with the detents 111d.

As shown in FIG. 15, injection is initiated by proximal movement of the cover sleeve 103 relative to the housing 102 to the retracted position. A proximal end of the cover sleeve 103 abuts the holding sleeve 108 (e.g., an outer body 108a of the holding sleeve 108) and pushes the holding sleeve 108 to its proximal position. When in the proximal position, the holding sleeve 108 is not radially aligned with the stop members 106b of the holding pin 106. Accordingly, the bias of the injection spring 109 acting on the piston rod 107 is sufficient to cam the stop members 106b out of the recesses 107a in the piston rod 107.

Accordingly, the piston rod 107 is free to move distally under the bias of the injection spring 109 towards the stopper 157 of the prefilled syringe 150. While moving distally, the piston rod 107 engages the stopper 157 of the prefilled syringe 150 and pushes the stopper 157 distally along the path of travel, P, within the syringe barrel 151. Distal movement of the stopper 157 pushes the fluid 160 through the needle 155 at the distal end 152 of the prefilled syringe 150.

Releasing the stop members 106b from the recesses 107a of the piston rod 107 also frees the holding pin 106 for movement relative to the piston rod 107. In certain implementations, the injection spring 109 biases the holding pin 106 proximally towards the end cap 112.

The stop members 106b of the holding pin 106 engage the distal end of the inner body 108b of the holding sleeve 108. The holding pin 106 entrains the inner body 108b of the holding sleeve 108 during this proximal movement until the inner body 108b abuts the support member 105. The impact between the inner body 108b of the holding sleeve 108 and the support member 105 creates a noise (e.g., a first click) that provides an audible indication that injection has started.

The stop members 106b inhibit movement of the inner body 108b of the holding sleeve 108 back to the distal position (see FIG. 16). The stop members 106b do not engage the outer body 108a of the holding sleeve 108. Accordingly, the outer body 108a can move distally over the stop members 106b (see FIG. 16).

When the piston rod 107 begins moving distally, the piston rod 107 entrains the indicator sleeve 111 via the engagement between the detents 111d and the slots 107c. Accordingly, the piston rod 107 moves the indicator sleeve 111 to the distal position against the bias of the cover sleeve spring 110. Engagement between the wings 111b of the indicator sleeve 111 and the support member 105 prohibits further distal movement of the indicator sleeve 111.

When the indicator sleeve 111 is disposed in the distal position, the detents 111d are axially offset from the holding sleeve 108 (see FIG. 17), which is disposed in the proximal position. Accordingly, the detents 111d are free to cam out of the slots 107c of the piston rod 107, thereby allowing the piston rod 107 to continue being moved distally by the injection spring 109. When moved radially outwardly, the detents 111d engage the distal end of the holding sleeve 108 (e.g., the inner body 108a), thereby preventing proximal movement of the indicator sleeve 111. The body of the piston rod 107 prevents radially inward deflection of the arms 111c and detents 111d during injection.

As shown in FIG. 16, the piston rod 107 moves the stopper 157 within the syringe barrel 151 until the stopper 157 bottoms out within the syringe barrel 151 (e.g., at the proximally facing shoulder 151a). The injection spring 109 continues to press the piston rod 107 against the stopper 157 when the stopper 157 is disposed in the bottomed-out position.

After injection is complete, the auto injector 140 is moved away from the injection site 198. The cover sleeve 103 is biased distally over the needle 155. In particular, the cover sleeve spring 110 biases the outer body 108a of the holding sleeve 108 distally. The stop members 106b of the holding pin 106 prevent distal movement of the inner body 108b of the holding sleeve 108. Accordingly, the outer body 108a moves distally relative to the inner body 108b until the inner body 108b and outer body 108a axially lock relative to each other. For example, a detent on the inner body 108b may snap into a recess defined by the outer body 108a.

Distal movement of the outer body 108a of the holding sleeve 108 pushes the cover sleeve 103 to the extended position. The outer body 108a is locked from proximal movement by the inner body 108b. The outer body 108a abuts the cover sleeve 103 to prevent proximal movement of the cover sleeve 103 back to the retracted position. Accordingly, the cover sleeve 103 is locked in the extended position covering the syringe needle 155.

As shown in FIG. 17, notches 107d defined at the proximal end of the piston rod 107 align with the detents 111d of the indicator sleeve 111 when the piston rod 107 reaches the bottomed-out position. The notches 107d allow the detents 111d to cam radially inwardly, thereby disengaging from the holding sleeve 108. Releasing the detents 111d from the holding sleeve 108 frees the indicator sleeve 111 for movement back to the proximal position under the bias of the cover sleeve spring 110. The cover sleeve spring 110 pushes the indicator sleeve 111 proximally against the end cap 112, which creates another noise (e.g., a second click) that provides an audible indication that injection has ended.

An example of an auto injector suitable for use with the apparatuses, methods, and uses disclosed herein include the YpsoMate® brand auto injector available from Yypsomed AG of Burgdof, Switzerland. Further details pertaining to example auto injectors suitable for use in actuating a prefilled syringe can be found in U.S. Publication No. 2016/0008541, the disclosure of which is hereby incorporated by reference in its entirety. The methods, apparatuses, and uses disclosed herein can be used with any type of auto injector that injects therapeutic fluid from a prefilled syringe.

The auto injectors and prefilled syringes disclosed herein, including those prefilled with the therapeutic fluids disclosed herein, are for use as a medicament to treat or prevent migraine headaches as well as other diseases, conditions, chronic illnesses and disabilities, and other therapeutic purposes. The prefilled syringes and auto injectors can be sold as a single unit with the prefilled syringe already inserted into the auto injector. Alternatively, the prefilled syringe and auto injector can be sold as a kit wherein the prefilled syringe and auto injector are either separate from one another but combined in the same packaging or sold together but in separate packages such that the prefilled syringe is in one package or box and the auto injector is in a different package or box.

Figure 18:
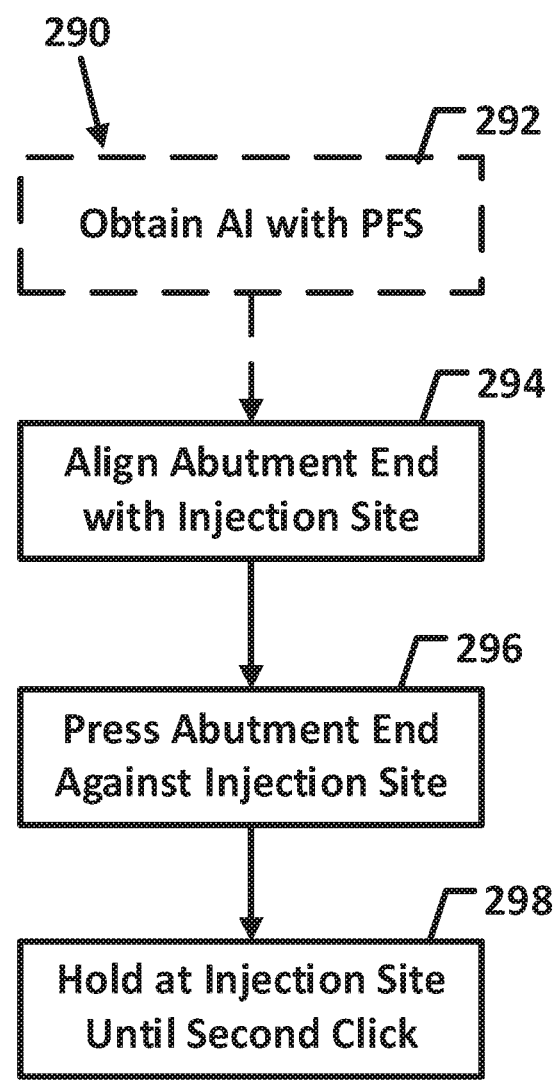
FIG. 18 is a flowchart illustrating a use process for using the auto injector with the prefilled syringe and the selected injection spring.
Figure 19:
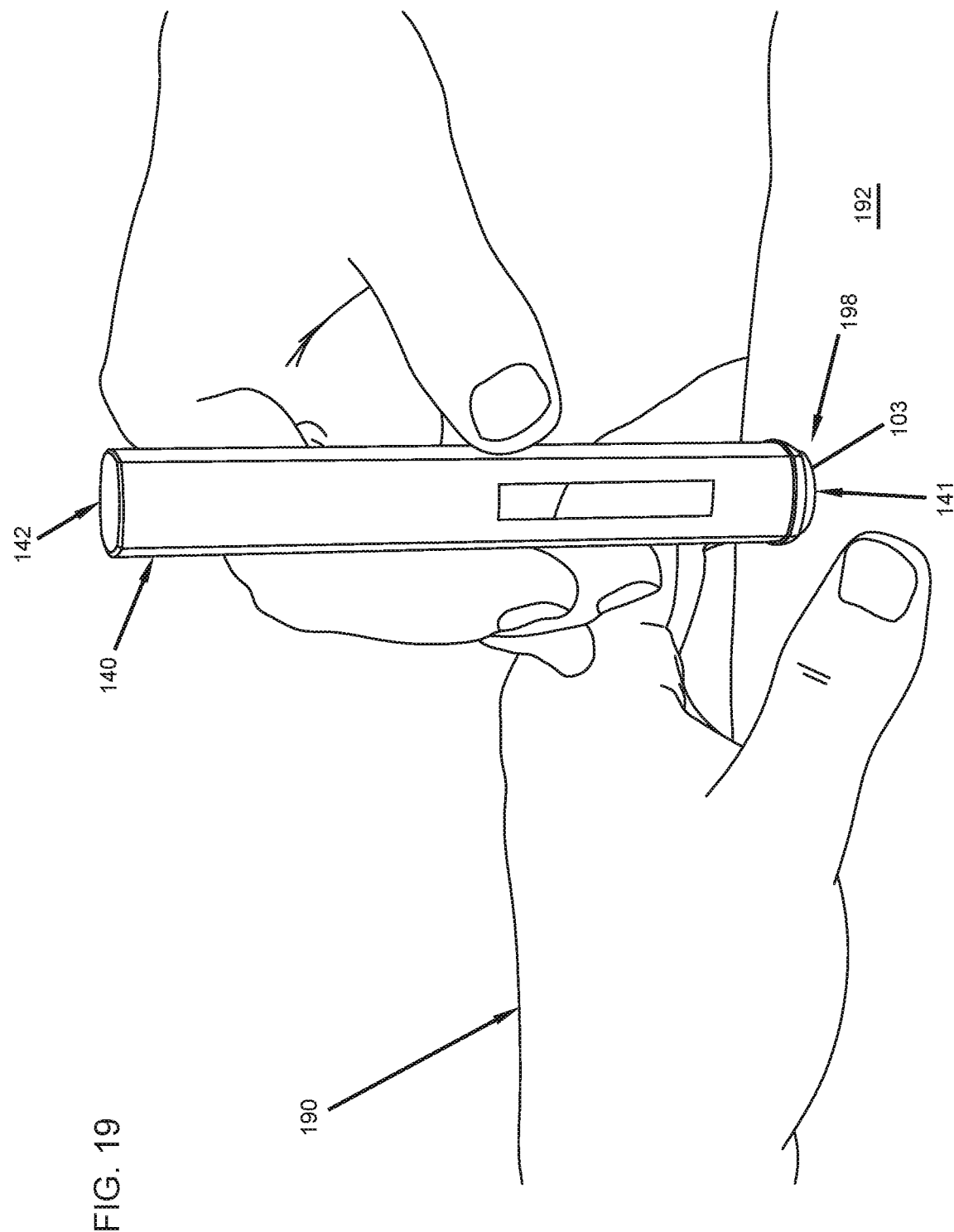
FIG. 19 illustrates the auto injector being actuated by a user.

FIG. 18 is a flowchart illustrating a use process 290 for using the auto injector 140 with prefilled syringe 150 and the selected injection spring 109. The disclosed methods and apparatuses can be used as needed, periodically or on a continuous schedule. For example, they can be used once a day, once a week, once a month, on a schedule of no more than once every month, no more than once every two months, no more than once every three months, or no more than once every four months. FIG. 19 illustrates the auto injector 140 being actuated by a user 190. The use process 290 includes at least an align operation 294, a press operation 296, and a hold operation 298. The use process 290 may optionally include an obtain operation 292.

At the obtain operation 292, the user 190 obtains an auto injector 140 containing a prefilled syringe 150. The auto injector 140 includes an injection spring 109 having a spring constant that is sufficient to drive injection of the prefilled syringe 150 even if the prefilled syringe 150 has aged. The injection spring 109 also is sufficiently strong to perform other operations within the auto injector 140 (e.g., charging the cover sleeve spring 110) in addition to biasing the stopper 157.

At the align operation 294, a distal end 141 of the auto injector 140 is aligned with the injection site 198 at the body 192 of a user 190.

At the press operation 296, the distal end 141 of the auto injector 140 is pressed against the injection site 198 (see FIG. 19). For example, the user 190 may push the outer body 102 of the auto injector 140 distally towards the injection site 198 as the cover sleeve 103 retracts into the outer body 102 to expose the needle 155. As described herein, retraction of the cover sleeve 103 within the body 102 automatically actuates the drive assembly to trigger injection of the prefilled syringe 150.

At the hold operation 298, the user 190 holds the auto injector 140 at the injection site 198 with the cover sleeve 103 retracted into the outer body 102 until the end of the injection. In certain examples, the end of the injection is indicated by an audible noise (e.g., a click) generated by the auto injector 140.

The methods, apparatuses, and uses disclosed herein have many aspects including the following.

One aspect is a method of adapting an auto injector configured to actuate a prefilled syringe, the auto injector having an injection spring having a spring constant, the prefilled syringe being filled with a volume of therapeutic fluid, the prefilled syringe including a barrel, stopper, and a needle, the stopper having a path of travel, the injection spring arranged to move the stopper along the path of travel the method comprising: aging the prefilled syringe at an accelerated rate to form an aged prefilled syringe; moving the stopper within the barrel of the aged prefilled syringe at a predetermined speed from at least a first position along the path of travel to at least a second position along the path of travel; measuring a plurality of exertion forces exerted on the stopper as the stopper moves within the barrel along the path of travel; determining a resistive force opposing movement of the stopper along the path of travel, the resistive force corresponding to the plurality of exertion forces; and selecting a spring constant for the injection spring, the act of selecting the spring constant comprising selecting the spring constant to correspond to the resistive force.

Another aspect is a method, alone or in any combination with the previous embodiments and aspects disclosed herein, wherein the operative prefilled syringe includes an operative barrel and an operative stopper movably positioned within the operative barrel, the operative stopper movable along an operative path of travel from a first operative position to a second operative position, the auto injector to comprise an injection spring having a spring force, the injection spring configured to apply a dispensing force to the operative stopper by driving a piston rod toward the operative stopper upon actuation of the auto injector, the dispensing force being at least a portion of the spring force, the method comprising: aging a prefilled syringe at an accelerated rate to form a reference prefilled syringe, the reference prefilled syringe including a reference barrel and a reference stopper positioned in the reference barrel; moving the reference stopper of the reference prefilled syringe along a reference path of travel from at least a first reference position to at least a second reference position; as the reference stopper moves within the reference barrel along the reference path of travel, measuring a plurality of exertion forces applied to the reference stopper and measuring a plurality of reference stopper positions; generating an exertion force profile, the exertion force profile including at least some of the exertion forces and reference stopper positions measured while the reference stopper was moving between the first and second reference positions, at least one of the measured exertion forces correlating to at least one of the measured reference stopper positions; and selecting the injection spring so that the dispensing force applied to the operative stopper at each position of the operative stopper as it moves along the operative path of travel between the first and second operative positions is greater than the measured exertion force at a corresponding one of the measured reference stopper positions.

Another aspect is a method, alone or in any combination with the previous embodiments and aspects disclosed herein, wherein selecting the injection spring comprises selecting a measured exertion force from the exertion force profile, and selecting at least one spring parameter, the selected at least one spring parameter corresponding to the selected exertion force.

Another aspect is a method, alone or in any combination with the previous embodiments and aspects disclosed herein, wherein selecting the at least one spring parameter comprises selecting a spring constant for the injection spring and an uncompressed length for the injection spring.

Another aspect is a method, alone or in any combination with the previous embodiments and aspects disclosed herein, wherein selecting at least one spring parameter comprises selecting a spring constant and a first compressed spring length corresponding to the reference stopper being at the first reference position along the reference path of travel.

Another aspect is a method, alone or in any combination with the previous embodiments and aspects disclosed herein, wherein selecting at least one spring parameter comprises selecting a spring constant and a second compressed spring length corresponding to the reference stopper being at a position along the reference path of travel corresponding to a maximum measured exertion force in the exertion force profile.

Another aspect is a method, alone or in any combination with the previous embodiments and aspects disclosed herein, wherein the selected spring has a dispensing force when the stopper is at the second final position that is greater than about 50% of the dispensing force when the stopper is at the first initial position.

Another aspect is a method, alone or in any combination with the previous embodiments and aspects disclosed herein, wherein the predetermined speed corresponds to a speed required to move the operative stopper along the operative path of travel from the first operative position to the second operative position in a range from about 5 seconds to about 19 seconds.

Another aspect is a method, alone or in any combination with the previous embodiments and aspects disclosed herein, wherein: a plunger is operably connected to the stopper and the act of moving the stopper comprises moving the plunger; and the act of measuring a plurality of exertion forces exerted on the stopper comprises measuring a plurality of exertion forces exerted on the plunger.

Another aspect is a method, alone or in any combination with the previous embodiments and aspects disclosed herein, wherein the act of determining the glide force includes determining the glide force required to move the stopper along the path of travel from the first position to the second position within a determined amount of time.

Another aspect is a method, alone or in any combination with the previous embodiments and aspects disclosed herein, wherein determining the first resistive force comprises determining the first resistive force when moving the stopper from the first position.

Another aspect is a method, alone or in any combination with the previous embodiments and aspects disclosed herein, wherein determining a resistive force comprises determining a resistive force selected from the group of: a break loose force, a maximum glide force, or combinations thereof.

Another aspect is a method, alone or in any combination with the previous embodiments and aspects disclosed herein, wherein determining a resistive force comprises determining a resistive force selected from the group consisting of: a break loose force, a maximum glide force, or combinations thereof.

Another aspect is a method, alone or in any combination with the previous embodiments and aspects disclosed herein, wherein determining a resistive force comprises determining at least first and second resistive forces, the first resistive force being a break loose force, and the second resistive force being a minimum glide force for moving the stopper along the path of travel from the first position at a beginning of the path of travel to the second position at an end of the path of travel without stalling.

Another aspect is a method, alone or in any combination with the previous embodiments and aspects disclosed herein, wherein the determined amount of time is in the range from about 5 s to about 25 s.

Another aspect is a method, alone or in any combination with the previous embodiments and aspects disclosed herein, wherein the act of determining the minimum glide force includes determining the minimum glide force required to move the stopper along the path of travel from the first position to the second position within about 5 seconds to about 25 seconds.

Another aspect is a method, alone or in any combination with the previous embodiments and aspects disclosed herein, wherein the aged prefilled syringe holds a determined volume of therapeutic fluid between the first position and the second position, and the act of determining a minimum glide force required to move the stopper along the path of travel from the first position to the second position without stalling comprises ejecting the determined volume of therapeutic fluid from the aged prefilled syringe.

Another aspect is a method, alone or in any combination with the previous embodiments and aspects disclosed herein, wherein the determined volume is in the range from about 1.51 mL to about 1.66 mL.

Another aspect is a method, alone or in any combination with the previous embodiments and aspects disclosed herein, wherein the auto injector comprises a subassembly, the subassembly movable in response to decompression of the injection spring, the subassembly arranged to selectively move the stopper, the act of selecting the spring constant comprising: selecting the spring constant to correspond to at least the first resistive force, the second resistive force, and a third resistive force, the third resistive force resistive to movement of the subassembly.

Another aspect is a method, alone or in any combination with the previous embodiments and aspects disclosed herein, wherein moving the stopper within the barrel of the aged prefilled syringe comprises moving the subassembly of the auto injector.

Another aspect is a method, alone or in any combination with the previous embodiments and aspects disclosed herein, wherein the auto injector comprises a subassembly, the subassembly operable in response to decompression of the injection spring, at least a portion of the subassembly arranged to selectively move the stopper, the act of selecting the spring constant comprising: selecting the spring constant to correspond to a force strong enough to operate the subassembly and to move the stopper from the first position to the second position without stalling.

Another aspect is a method, alone or in any combination with the previous embodiments and aspects disclosed herein, wherein moving the stopper within the barrel of the aged prefilled syringe comprises moving the subassembly of the auto injector.

Another aspect is a method, alone or in any combination with the previous embodiments and aspects disclosed herein, wherein the therapeutic fluid comprises an antibody.

Another aspect is a method, alone or in any combination with the previous embodiments and aspects disclosed herein, wherein the antibody comprises a humanized monoclonal antibody.

Another aspect is a method, alone or in any combination with the previous embodiments and aspects disclosed herein, wherein the humanized monoclonal antibody comprises an immunoglobulin $G_2$ (IgG2) antibody.

Another aspect is a method, alone or in any combination with the previous embodiments and aspects disclosed herein, wherein the humanized monoclonal antibody comprises an anti-calcitonin gene-related peptide antibody.

Another aspect is a method, alone or in any combination with the previous embodiments and aspects disclosed herein, wherein the therapeutic fluid has a viscosity in the range from about 4 cSt to about 14 cSt at 22° C.

Another aspect is a method, alone or in any combination with the previous embodiments and aspects disclosed herein, wherein the therapeutic fluid comprises fremanezumab and has a viscosity in the range from about 4 cSt to about 14 cSt at 22° C.

Another aspect is a method, alone or in any combination with the previous embodiments and aspects disclosed herein, wherein the barrel of the prefilled syringe comprises an inner surface, and the prefilled syringe further comprises a lubricant on the inner surface.

Another aspect is a method, alone or in any combination with the previous embodiments and aspects disclosed herein, wherein the lubricant comprises silicone oil.

Another aspect is a method, alone or in any combination with the previous embodiments and aspects disclosed herein, wherein the lubricant comprises polydimethylsiloxane.

Another aspect is a method, alone or in any combination with the previous embodiments and aspects disclosed herein, wherein the silicone oil coats the inner surface of the barrel and the thickness of the coating is between about 0.1 µm and about 0.3 µm before the prefilled syringe is aged.

Another aspect is a method, alone or in any combination with the previous embodiments and aspects disclosed herein, wherein the lubricant comprises between about 0.35 mg and about 1.1 mg of silicone oil before the prefilled syringe is aged.

Another aspect is a method, alone or in any combination with the previous embodiments and aspects disclosed herein, wherein the silicone oil has a viscosity between about 500 cSt and about 1500 cSt at 25° C. before the prefilled syringe is aged.

Another aspect is a method, alone or in any combination with the previous embodiments and aspects disclosed herein, wherein aging the prefilled syringe comprises heating the prefilled syringe for a determined period of time.

Another aspect is a method, alone or in any combination with the previous embodiments and aspects disclosed herein, wherein the determined period of time is calculated according to the Arrhenius equation.

Another aspect is a method, alone or in any combination with the previous embodiments and aspects disclosed herein, wherein: the determined period of time is calculated according to the Arrhenius equation; and heating the prefilled syringe for a determined period of time comprises heating the prefilled syringe at a temperature in the range from about 20° C. to about 60° C.

Another aspect is a method, alone or in any combination with the previous embodiments and aspects disclosed herein, wherein the barrel of the prefilled syringe has a volume selected from the group of about 1 mL to about 2.25 mL.

Another aspect is a method, alone or in any combination with the previous embodiments and aspects disclosed herein, wherein the barrel of the prefilled syringe has a volume selected from the group consisting of about 1 mL to about 2.25 mL.

Another aspect is a method, alone or in any combination with the previous embodiments and aspects disclosed herein, wherein the distance between the first reference position of the reference stopper and the second reference position of the reference stopper is in the range from about 25.7 mm to about 30 mm.

Another aspect is a method, alone or in any combination with the previous embodiments and aspects disclosed herein, wherein the distance between the first position of the stopper and the second position of the stopper is in the range from about 35 mm to about 55 mm.

Another aspect is a method, alone or in any combination with the previous embodiments and aspects disclosed herein, wherein the needle defines a channel and the channel has a diameter in the range from about 0.15 mm to about 0.3 mm.

Another aspect is a method, alone or in any combination with the previous embodiments and aspects disclosed herein, wherein the channel defined by the needle has a length in the range from about 15 mm to about 25 mm.

Another aspect is a method, alone or in any combination with the previous embodiments and aspects disclosed herein, wherein the barrel comprises glass.

Another aspect is a method, alone or in any combination with the previous embodiments and aspects disclosed herein, wherein the barrel comprises Borosilicate glass.

Another aspect is a method, alone or in any combination with the previous embodiments and aspects disclosed herein, wherein the barrel of the prefilled syringe has an inner diameter in the range from about 6 mm to about 10 mm.

Another aspect is a method, alone or in any combination with the previous embodiments and aspects disclosed herein, wherein the stopper comprises ethylene tetrafluoroethylene.

Another aspect is a method, alone or in any combination with the previous embodiments and aspects disclosed herein, wherein the injection spring is a spring selected from the group of: a variable force spring, a constant force spring, a helical spring, a conical spring, a torsion spring, a gas spring, a hydraulic spring, and combinations thereof.

Another aspect is a method, alone or in any combination with the previous embodiments and aspects disclosed herein, wherein the injection spring is a spring selected from the group consisting of: a variable force spring, a constant force spring, a helical spring, a conical spring, a torsion spring, a gas spring, a hydraulic spring, and combinations thereof.

Another aspect is an auto injector for actuating a prefilled syringe containing a dosage of a therapeutic fluid, alone or in any combination with the previous embodiments and aspects disclosed herein, wherein the therapeutic fluid comprising fremanezumab, and the auto injector made by a process comprising: any combination of the actions recited above; selecting a spring having the selected spring constant; and assembling the auto injector with the selected spring.

Another aspect is an auto injector, alone or in any combination with the previous embodiments and aspects disclosed herein, the auto injector arrangement comprising: a prefilled syringe including a barrel extending along a longitudinal axis between a distal end and a proximal end, an inner diameter of the barrel being about 8.65 mm, a needle disposed at the distal end of the barrel, the needle having an inner diameter of about 0.21 mm and a length of about 20 mm or less, a therapeutic fluid held within the barrel, a viscosity of the therapeutic fluid being in the range of about 14 cSt or less at 22° C., and a stopper disposed within the barrel to retain the fluid within the barrel, the barrel defining a path of travel for the stopper, the path of travel having a first position for the stopper and a second position for the stopper, the therapeutic fluid comprising fremanezumab; and an auto injector holding the prefilled syringe, the auto injector comprising a plunger and an injection spring, the plunger engaging the stopper, and the injection spring biasing the plunger towards the stopper, the injection spring having a spring force of at least about 20 N when the stopper is positioned at the first position.

Another aspect is an auto injector, alone or in any combination with the previous embodiments and aspects disclosed herein, the auto injector arrangement comprising: a prefilled syringe including a barrel extending along a longitudinal axis between a distal end and a proximal end, an inner diameter of the barrel being of about 8.65 mm, a needle disposed at the distal end of the barrel, the needle having an inner diameter of about 0.27 mm and a length of about 19.5 mm or less, a volume in the range from about 1.51 mL to about 1.66 mL of therapeutic fluid held within the barrel, the therapeutic fluid comprising fremanezumab, a viscosity of the therapeutic fluid being about 8.8 cSt at 22° C., and a stopper disposed within the barrel to retain the therapeutic fluid within the barrel, the barrel defining a path of travel for the stopper, the path of travel having a first initial position for the stopper and a second final position for the stopper, the first position being an initial position of the stopper before delivery of the therapeutic fluid, the second position being a final position of the stopper upon delivery of a full dose of the therapeutic fluid; and an auto injector holding the prefilled syringe, the auto injector comprising an injection spring arranged to apply a dispensing force to the stopper by driving a piston rod toward the stopper, wherein, when the auto injector is actuated, the injection spring is configured to provide an initial dispensing force to the stopper of at least about 20 N when the stopper is positioned at the first initial position and a final dispensing force of about 12 N or greater to the stopper when the stopper is positioned at the second final position, the dispensing force being at least a portion of a spring force for the injection spring.

Another aspect is an auto injector, alone or in any combination with the previous embodiments and aspect disclosed herein, wherein the injection spring is configured to provide a final dispensing force of at least 12.5 N to the stopper when the stopper is positioned at the second final position.

Another aspect is an auto injector, alone or in any combination with the previous embodiments and aspect disclosed herein, wherein the injection spring is configured to provide a final dispensing force of at least 14 N to the stopper when the stopper is positioned at the second final position.

Another aspect is an auto injector, alone or in any combination with the previous embodiments and aspect disclosed herein, wherein the injection spring is configured to provide a final dispensing force of at least 12 N to the stopper when the stopper is positioned at the second final position and the prefilled syringe has an accelerated age of about 24 months.

Another aspect is an auto injector, alone or in any combination with the previous embodiments and aspects disclosed herein, wherein the injection spring has a spring force in the range from about 20 N to about 30 N when the stopper is positioned at the first initial position.

Another aspect is an auto injector, alone or in any combination with the previous embodiments and aspects disclosed herein, wherein the injection spring is configured to provide a final dispensing force in the range from about 12 N to about 20 N when the stopper is positioned at the second final position.

Another aspect is an auto injector, alone or in any combination with the previous embodiments and aspects disclosed herein, wherein the injection spring is configured to provide a final dispensing force in the range from about 12.5 N to about 20 N when the stopper is positioned at the second final position.

Another aspect is an auto injector, alone or in any combination with the previous embodiments and aspects disclosed herein, when the stopper is at the first initial position, an actual stored spring energy of the injection spring is at least about 25% greater than a minimum stored spring energy required to move the stopper from the first position to the second position without stalling an unaged prefilled syringe.

Another aspect is an auto injector, alone or in any combination with the previous embodiments and aspects disclosed herein, wherein the injection spring has a stored energy in the range from about 0.9 J to about 2 J when the injection spring is in the first position.

Another aspect is an auto injector, alone or in any combination with the previous embodiments and aspects disclosed herein, wherein the injection spring has a spring constant in the range from about 0.2 N/mm to about 0.4 N/mm and a compressed length when in the first initial position in the range from about 50 mm to about 100 mm.

Another aspect is an auto injector, alone or in any combination with the previous embodiments and aspects disclosed herein, wherein the injection spring has a spring constant in the range from about 0.28 N/mm to about 0.32 N/mm and compressed length when in the first initial position in the range from about 75 mm to about 95 mm.

Another aspect is an auto injector, alone or in any combination with the previous embodiments and aspects disclosed herein, wherein the injection spring has a force sufficient to move the stopper along the path of travel from the first position to the second position within about 5 seconds to about 25 seconds.

Another aspect is an auto injector, alone or in any combination with the previous embodiments and aspects disclosed herein, wherein: the barrel of the prefilled syringe comprises glass and defines an inner surface; and the prefilled syringe further comprises between about 0.4 mg and about 1.1 mg of silicone oil on the inner surface before the prefilled syringe is aged.

Another aspect is an auto injector, alone or in any combination with the previous embodiments and aspects disclosed herein, wherein the injection spring is configured to move the stopper along the path of travel from the first position to the second position within the range from about 5 seconds to about 19 seconds.

Another aspect is an auto injector, alone or in any combination with the previous embodiments and aspects disclosed herein, wherein the silicone oil has a viscosity between about 500 cSt and about 1500 cSt at 25° C. before the prefilled syringe is aged.

Another aspect is an auto injector, alone or in any combination with the previous embodiments and aspects disclosed herein, wherein the silicone oil has a viscosity of about 1000 cSt at 25° C. before the prefilled syringe ages.

Another aspect is an auto injector, alone or in any combination with the previous embodiments and aspects disclosed herein, wherein the stopper has a length in the range from about 7.3 mm to about 8.1 mm.

Another aspect is an auto injector, alone or in any combination with the previous embodiments and aspects disclosed herein, wherein the stopper has a compressed state and an uncompressed state, and the stopper comprises: a main body, the main body being substantially cylindrical and having a diameter in the uncompressed state in the range from about 8.85 mm to about 9.05 mm; and at least one annular rib, the annular rib extending radially from the main body, the annular rib having an outer diameter in the uncompressed state in the range from about 9.25 mm to about 9.45 mm.

Another aspect is an auto injector, alone or in any combination with the previous embodiments and aspects disclosed herein, wherein a portion of the stopper is coated with ethylene tetrafluoroethylene, and a portion of the stopper is coated with silicone.

Another aspect is an auto injector, alone or in any combination with the previous embodiments and aspects disclosed herein, wherein a distance between the first position for the stopper and the second position for the stopper is in the range from about 25.7 mm to about 30 mm.

Another aspect is an auto injector, alone or in any combination with the previous embodiments and aspects disclosed herein, wherein the prefilled syringe has a volume selected from the group of about 1 mL and about 2.25 mL.

Another aspect is an auto injector, alone or in any combination with the previous embodiments and aspects disclosed herein, wherein the prefilled syringe has a volume selected from the group consisting of about 1 mL and about 2.25 mL.

Another aspect is an auto injector, alone or in any combination with the previous embodiments and aspects disclosed herein, wherein the therapeutic fluid has a viscosity in the range from about 4 cSt to about 10 cSt at 22° C.

Another aspect is an auto injector, alone or in any combination with the previous embodiments and aspects disclosed herein, wherein the injection spring is determined according to the actions recited in claim 1.

Another aspect is an auto injector, alone or in any combination with the previous embodiments and aspects disclosed herein, the auto injector arrangement comprising: a prefilled syringe; the prefilled syringe comprising a barrel formed at least in part by glass, a needle in fluid communication with the barrel, and a stopper positioned in the barrel, the barrel defining an inner surface, the barrel having an inner diameter, the barrel being about 8.65 mm and a volume of about 2.25 mL, the barrel defining a path of travel for the stopper, the path of travel having a first position for the stopper and a second position for the stopper, the needle having an inner diameter of about 0.21 mm and a length of about 20 mm or less, a therapeutic fluid held within the barrel, a viscosity of the therapeutic fluid being in the range of about 10 cP or less at 22° C., the therapeutic fluid comprising fremanezumab; about 0.35 mg to about 1.1 mg of silicone oil lubricating the inner surface of the barrel, the silicone oil having a viscosity between about 500 cSt and about 1500 cSt at 25° C. before the prefilled syringe is aged; and an auto injector holding the prefilled syringe, the auto injector comprising a plunger and an injection spring, the plunger engaging the stopper, and the injection spring biasing the plunger towards the stopper, the injection spring when in the first position: has a force determined according to the actions recited in claim 1; is in the range from about 20 N to about 30 N; is about 25% greater than spring force required to move the stopper from the first position to the second position without stalling before the prefilled syringe is aged; and has a force sufficient to move the stopper along the path of travel from the first position to the second position within about 5 seconds to about 25 seconds.

Another aspect is an auto injector apparatus for actuating a prefilled syringe containing a dosage of a therapeutic fluid, alone or in any combination with the previous embodiments and aspects disclosed herein, the therapeutic fluid comprising an immunoglobulin G2 (IgG2) humanized monoclonal antibody, the auto injector made by a process comprising the operations of: aging the prefilled syringe to form an aged prefilled syringe; moving the stopper within the barrel of the aged prefilled syringe at a predetermined speed from at least a first position along the path of travel to at least a second position along the path of travel; measuring a plurality of exertion forces exerted on the stopper as the stopper moves within the barrel along the path of travel; determining at least first and second resistive forces opposing movement of the stopper along the path of travel, the first and second resistive forces corresponding to the plurality of exertion forces; selecting a spring constant for the injection spring, the act of selecting the spring constant comprising selecting the spring constant to correspond to at least one of the first and second resistive forces; selecting a spring having the selected spring constant; and assembling the auto injector with the selected spring.

Another aspect is an auto injector apparatus configured to move a stopper within a barrel of a syringe to effect delivery of a fluid from the syringe, alone or in any combination with the previous embodiments and aspects disclosed herein, the auto injector apparatus comprising: a syringe barrel, the syringe barrel having an empty state and a filled state, the empty state occurring before the filled state, the syringe holding a dose of therapeutic fluid when in the filled state, the therapeutic fluid comprising an immunoglobulin $G_2$ (IgG2) humanized monoclonal antibody; a stopper positioned in the syringe barrel, the stopper having a path of travel between a first position and a second position, the dose of therapeutic fluid being substantially positioned between the first and second positions; and an injection spring having a spring constant, the spring constant providing the injection spring with a first spring force that is at least 25% greater than a second spring force, the first spring force corresponding to the minimum spring force required to move the stopper from the first position to the second position when the barrel is in the filled state, and the second spring force corresponding to the minimum spring force required to move the stopper from the first position to the second position when the barrel is in the empty state.

Another aspect is an auto injector apparatus configured to move a stopper within a barrel of a syringe to effect delivery of a fluid from the syringe, alone or in any combination with the previous embodiments and aspects disclosed herein, the auto injector apparatus comprising: a prefilled syringe, the prefilled syringe having an unaged state and an aged state, the prefilled syringe holding a dose of therapeutic fluid when in the filled state, the therapeutic fluid comprising an immunoglobulin $G_2$ (IgG2) humanized monoclonal antibody; a stopper positioned in the prefilled syringe, the stopper having a path of travel between a first position and a second position, the dose of therapeutic fluid being substantially positioned between the first and second positions; and an injection spring having a spring constant, the spring constant providing the injection spring with a first spring force that is at least 25% greater than a second spring force, the first spring force corresponding to the minimum spring force required to move the stopper from the first position to the second position when the prefilled syringe is in the aged state, and the second spring force corresponding to the minimum spring force required to move the stopper from the first position to the second position when the prefilled syringe is in the unaged state.

Another aspect is a prefilled syringe combination, alone or in any combination with the previous embodiments and aspects disclosed herein, for use as a medicament to treat or prevent migraine headaches Another aspect is a prefilled syringe containing fremanezumab, alone or in any combination with the previous embodiments and aspects disclosed herein, for use as a medicament to treat or prevent migraine headaches.

Another aspect is a prefilled syringe containing a therapeutic fluid comprising fremanezumab, alone or in any combination with the previous embodiments and aspects disclosed herein, for use as a medicament to treat or prevent migraine headaches.

Another aspect is a prefilled syringe containing a therapeutic fluid comprising fremanezumab and formulated at 150 mg/mL nominal concentration in 16 mM histidine, 6.6% sucrose, 0.136 mg/mL EDTA, 1.2 mg/mL P580, pH 5.5, alone or in any combination with the previous embodiments and aspects disclosed herein, for use as a medicament to treat or prevent migraine headaches.

Another aspect is a prefilled syringe containing fremanezumab in any combination with an auto injector, alone or in any combination with the previous embodiments and aspects disclosed herein, for use as a medicament to treat or prevent migraine headaches, the prefilled syringe filled with a therapeutic fluid formulated at 150 mg/mL nominal concentration in 16 mM histidine, 6.6% sucrose, 0.136 mg/mL EDTA, 1.2 mg/mL P580, pH 5.5.

Another aspect is a prefilled syringe containing fremanezumab for use as a medicament to treat or prevent migraine headaches, according to a continuous schedule of no more than once every two months, either alone or in any combination with the previous embodiments and aspects.

Another aspect is a prefilled syringe containing fremanezumab for use as a medicament to treat or prevent migraine headaches, according to a continuous schedule of no more than once every three months, either alone or in any combination with the previous embodiments and aspects.

Another aspect is a prefilled syringe containing fremanezumab for use as a medicament to treat or prevent migraine headaches, according to a continuous schedule of no more than once every four months, either alone or in any combination with the previous embodiments and aspects.

Another aspect is an auto injector, either alone or in any combination with any of the previous embodiments and aspects, the auto injector comprising: a prefilled syringe comprising a stopper and a therapeutic fluid including fremanezumab; and an auto injector having an injection spring and a piston rod arranged to move the stopper from a first position to a second position with a force of about 30 N or less and in about 19 seconds or less, the distance between the first and second positions corresponding to one dose of the therapeutic fluid.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims. It is intended that any such modifications and equivalents be included in the scope of the claims.

The invention claimed is:

1. An auto injector apparatus comprising:
   a prefilled syringe including:
      a barrel having a proximal end and a distal end and that extends along a longitudinal axis between the proximal end and the distal end, the barrel having an inner diameter of about 8.65 mm;
      a needle disposed at the distal end of the barrel, the needle having an inner diameter of about 0.27 mm and a length of about 19.5 mm or less;
      a therapeutic fluid held within the barrel, the therapeutic fluid comprising fremanezumab, the therapeutic fluid having a volume of between about 1.51 mL and about 1.66 mL and a viscosity of about 8.8 cSt at 22° C.; and
      a stopper disposed within the barrel, the stopper being configured to move axially within the barrel along a path of travel between a first position and a second position to expel at least some of the volume of the therapeutic fluid from the prefilled syringe, the first position being an initial position of the stopper before a delivery of the therapeutic fluid, and the second position being a final position of the stopper at the end of the delivery of the therapeutic fluid; and
   an auto injector that holds the prefilled syringe, the auto injector comprising:
      a piston rod configured to abut the stopper; and
      an injection spring configured drive the piston rod into abutment with the stopper to apply a dispensing force to the stopper,
   wherein, upon an actuation of the auto injector, the injection spring is configured to provide, via the piston rod, an initial dispensing force of between 20 N and 40 N to the stopper when the stopper is positioned at the first position and is configured to provide, via the piston rod, a final dispensing force of between 12 N and 20 N to the stopper to move the stopper to the second position,
   wherein the initial dispensing force is greater than the final dispensing force, and
   wherein the dispensing force is at least a portion of a spring force for the injection spring.

2. The auto injector apparatus of claim 1, wherein the final dispensing force is at least 12.5 N.

3. The auto injector apparatus of claim 2, wherein the final dispensing force is at least 14 N.

4. The auto injector apparatus of claim 1, wherein the prefilled syringe has an accelerated age of about 24 months.

5. The auto injector apparatus of claim 1, wherein the initial dispensing force is between about 20 N and about 30 N.

6. The auto injector apparatus of claim 1, wherein the final dispensing force is between about 15 N and about 18 N.

7. The auto injector apparatus of claim 1, wherein the prefilled syringe is unaged, and
   wherein, when the stopper is at the first position, an actual stored spring energy of the injection spring is at least 25% greater than a minimum stored spring energy required to move the stopper from the first position to the second position without stalling the prefilled syringe.

8. The auto injector apparatus of claim 1, wherein the injection spring has a stored energy of between about 0.9 J and about 2 J when the stopper is positioned in the first position.

9. The auto injector apparatus of claim 8, wherein, when the stopper is positioned in the first position, the injection spring has a spring constant of between about 0.2 N/mm and about 0.4 N/mm and a compressed length of between about 50 mm and about 100 mm.

10. The auto injector apparatus of claim 9, wherein the spring constant is between about 0.28 N/mm and about 0.32 N/mm and the compressed length is between about 75 mm and about 95 mm.

11. The auto injector apparatus of claim 10, wherein the injection spring is configured to move the stopper, via the piston rod, along the path of travel from the first position to the second position within a period of between about 5 seconds and about 19 seconds.

12. The auto injector apparatus of claim 1, wherein:
the prefilled syringe is unaged,
the barrel of the prefilled syringe comprises glass and defines an inner surface, and
the prefilled syringe further comprises between about 0.4 mg and about 1.1 mg of silicone oil on the inner surface.

13. The auto injector apparatus of claim 12, wherein the silicone oil has a viscosity of about 1000 cSt at 25° C.

14. The auto injector apparatus of claim 1, wherein the stopper has a length of between about 7.3 mm and about 8.1 mm.

15. The auto injector apparatus of claim 14, wherein the stopper is configured to compress to a compressed state and relax to an uncompressed state, and the stopper comprises:
a main body being substantially cylindrical and having a diameter in the uncompressed state of between about 8.85 mm and about 9.05 mm; and
at least one annular rib extending radially from the main body, the annular rib having an outer diameter in the uncompressed state of between about 9.25 mm and about 9.45 mm.

16. The auto injector apparatus of claim 14, wherein a portion of the stopper is coated with ethylene tetrafluoroethylene, and another portion of the stopper is coated with silicone.

17. The auto injector apparatus of claim 1, wherein a distance between the first position and the second position is between about 25.7 mm and about 30 mm.

18. The auto injector apparatus of claim 1, wherein the initial dispensing force and the final dispensing force provided by the injection spring are each greater than measured exertion forces at corresponding measured stopper reference positions, the measured exertion forces and the corresponding measured stopper reference positions are measured as a reference stopper moves along a reference path of travel from at least a first reference position to at least a second reference position within a reference barrel of an accelerated aged syringe prefilled with the therapeutic fluid.

19. An auto injector apparatus comprising:
a prefilled syringe comprising a stopper and a therapeutic fluid including fremanezumab; and
an auto injector comprising an injection spring and a piston rod, the piston rod being configured to move the stopper from a first position to a second position with in about 19 seconds or less,
wherein, upon an actuation of the auto injector, the injection spring is configured to provide, via the piston rod, an initial dispensing force between 20 N and 40 N to the stopper when the stopper is positioned at the first position and is configured to provide, via the piston rod, a final dispensing force of between 12 N and 20 N to the stopper to move the stopper to the second position, the initial dispensing force is greater than the final dispensing force, and
wherein a distance between the first and second positions corresponds to one dose of the therapeutic fluid.

* * * * *